US012016553B2

(12) United States Patent
Dalessandro et al.

(10) Patent No.: US 12,016,553 B2
(45) Date of Patent: Jun. 25, 2024

(54) BRAIDED BARBED SUTURES HAVING BARBED MONOFILAMENT INSERTS WITH CONCAVE CORE PROFILES

(71) Applicant: Ethicon, Inc., Somerville, NJ (US)

(72) Inventors: Victoria Dalessandro, Scotch Plains, NJ (US); Jason T. Perkins, Easton, PA (US); Robert C. Scogna, Rocky Hill, NJ (US)

(73) Assignee: Ethicon, Inc., Raritan, NJ (US)

( * ) Notice: Subject to any disclaimer, the term of this patent is extended or adjusted under 35 U.S.C. 154(b) by 269 days.

(21) Appl. No.: 17/336,692

(22) Filed: Jun. 2, 2021

(65) Prior Publication Data

US 2021/0386423 A1    Dec. 16, 2021

Related U.S. Application Data

(60) Provisional application No. 63/039,656, filed on Jun. 16, 2020.

(51) Int. Cl.
*A61B 17/06* (2006.01)
*A61L 17/10* (2006.01)

(52) U.S. Cl.
CPC ...... *A61B 17/06166* (2013.01); *A61L 17/105* (2013.01); *A61B 2017/06176* (2013.01)

(58) Field of Classification Search
CPC .............. A61B 2017/06176; A61L 17/105
See application file for complete search history.

(56) References Cited

U.S. PATENT DOCUMENTS

| 4,546,769 A | 10/1985 | Planck et al. |
| 4,946,467 A | 8/1990 | Ohi et al. |
| 5,931,855 A | 8/1999 | Buncke |

(Continued)

FOREIGN PATENT DOCUMENTS

| EP | 2895081 | 4/2019 |
| EP | 3533399 | 9/2019 |
| EP | 3180040 | 5/2020 |

OTHER PUBLICATIONS

International Search Report issued in corresponding International Application No. PCT/IB2021/055170, mailed on Sep. 3, 2021, 6 pages.

(Continued)

*Primary Examiner* — Alexander J Orkin

(57) ABSTRACT

A braided barbed suture includes a barbed monofilament insert including an elongated core having a thickness and a plurality of barbs projecting outwardly from opposite sides of the elongated core. The braided barbed suture includes a braided sheath surrounding the elongated core to form a composite core of the braided barbed suture. The composite core has a thickness and the elongated core is located in a center of the composite core. The elongated core thickness is about 6-8 mil and the composite core thickness is about 13-18 mil. A ratio of the elongated core thickness relative to the composite core thickness is between about 0.16 to 0.91. The elongated core has transition zones that form a concave profile. The braided barbed suture has a single breaking point for both the braided sheath and the barbed monofilament insert. The barbed monofilament insert has a PDS monofilament core, and the braided sheath is a VICRYL multifilament yarn braided sheath.

29 Claims, 29 Drawing Sheets

(56) References Cited

U.S. PATENT DOCUMENTS

| | | | |
|---|---|---|---|
| 6,162,537 A * | 12/2000 | Martin | D01F 8/12 |
| | | | 606/228 |
| 8,210,085 B2 | 7/2012 | Lindh, Sr. et al. | |
| 8,216,497 B2 | 7/2012 | Lindh, Sr. et al. | |
| 8,353,931 B2 | 1/2013 | Stopek et al. | |
| 8,663,277 B2 | 3/2014 | Collier et al. | |
| 8,715,320 B2 | 5/2014 | Lindh, Sr. | |
| 8,733,223 B2 | 5/2014 | Lindh, Sr. et al. | |
| 9,044,225 B1 | 6/2015 | Goraltchouk et al. | |
| 9,206,535 B2 | 12/2015 | Lindh, Sr. et al. | |
| 2004/0199208 A1 | 10/2004 | Foerster | |
| 2005/0203576 A1 * | 9/2005 | Sulamanidze | A61B 17/06166 |
| | | | 606/228 |
| 2005/0267531 A1 * | 12/2005 | Ruff | A61B 17/06166 |
| | | | 606/228 |
| 2005/0267532 A1 * | 12/2005 | Wu | A61B 17/06166 |
| | | | 606/228 |
| 2007/0005110 A1 * | 1/2007 | Collier | A61F 2/2409 |
| | | | 606/228 |
| 2007/0257395 A1 | 11/2007 | Lindh et al. | |
| 2008/0312688 A1 * | 12/2008 | Nawrocki | A61B 17/06166 |
| | | | 606/228 |
| 2009/0099597 A1 * | 4/2009 | Isse | A61B 17/06166 |
| | | | 606/228 |
| 2010/0298872 A1 * | 11/2010 | Berndt | A61B 17/06166 |
| | | | 87/8 |
| 2011/0251640 A1 * | 10/2011 | Lauria | A61B 17/06166 |
| | | | 606/228 |
| 2012/0136388 A1 * | 5/2012 | Odermatt | D01D 10/00 |
| | | | 606/228 |
| 2013/0079815 A1 * | 3/2013 | Hasan | A61B 17/06166 |
| | | | 606/228 |
| 2013/0204295 A1 * | 8/2013 | Hunter | A61B 17/0401 |
| | | | 606/228 |
| 2013/0226233 A1 | 8/2013 | D'Agostino et al. | |
| 2013/0226234 A1 | 8/2013 | Avelar et al. | |
| 2015/0032155 A1 | 1/2015 | Dreyfuss et al. | |
| 2015/0073474 A1 * | 3/2015 | Hodgkinson | A61B 17/06166 |
| | | | 606/228 |
| 2017/0224338 A1 | 8/2017 | Sung | |

OTHER PUBLICATIONS

Written Opinion of the International Searching authority issued in corresponding International Application No. PCT/IB2021/055170, mailed on Sep. 3, 2021, 6 pages.

* cited by examiner

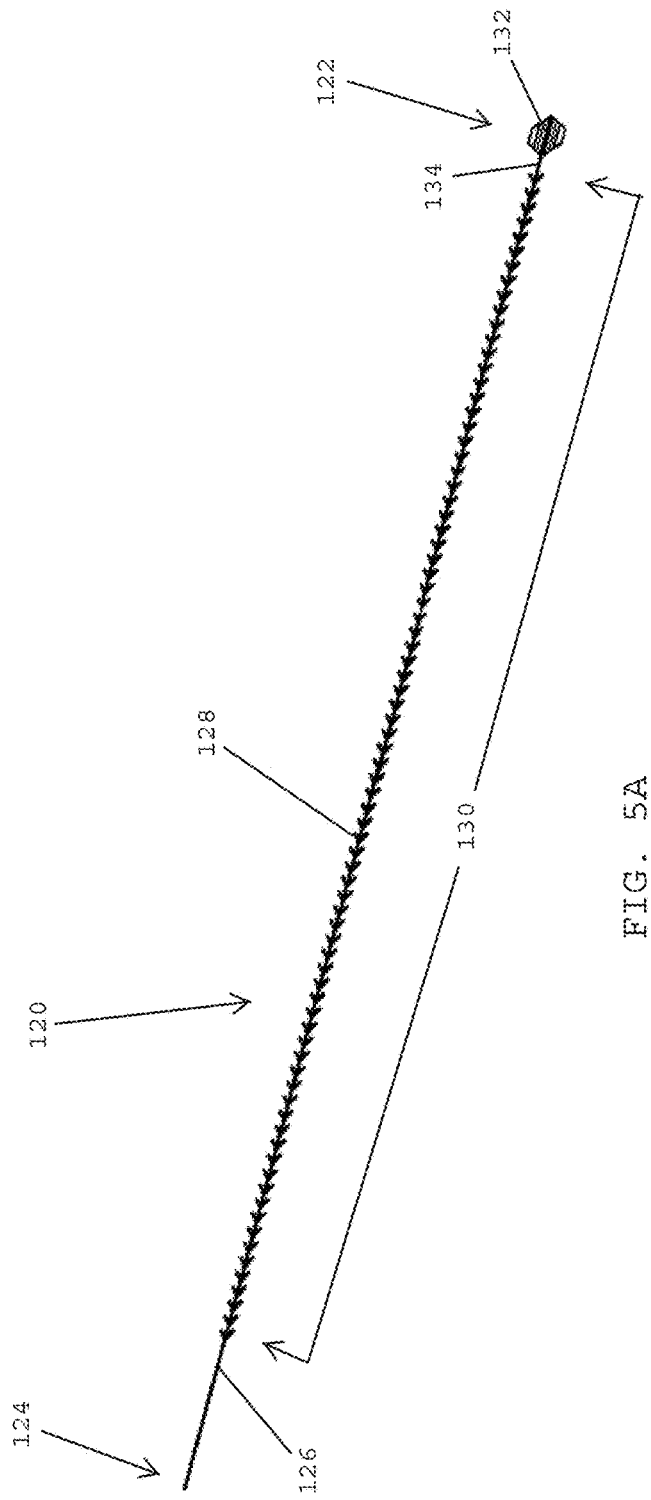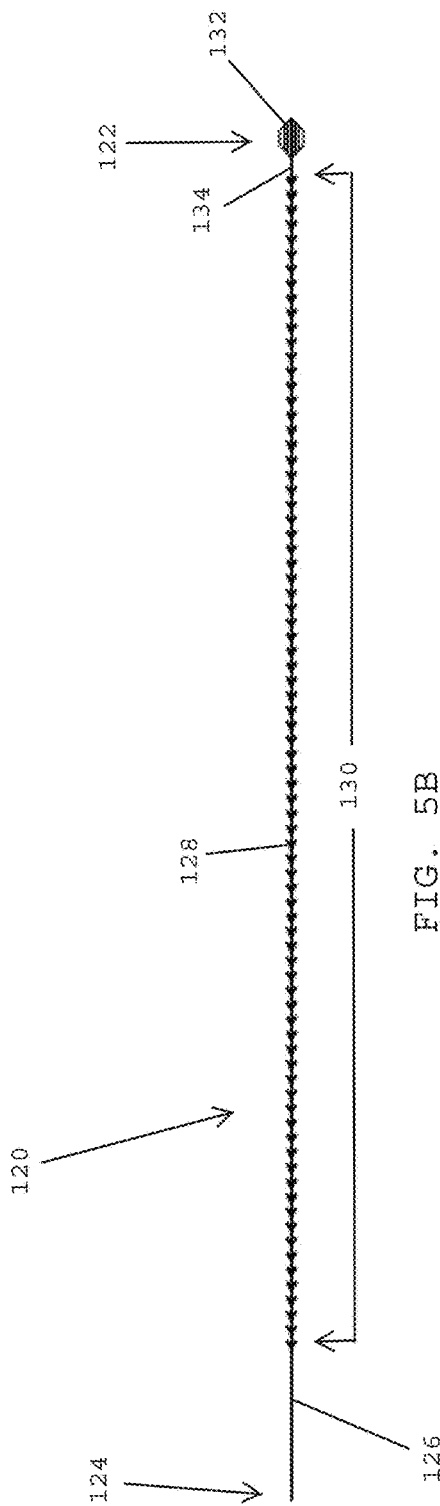
FIG. 5A
FIG. 5B

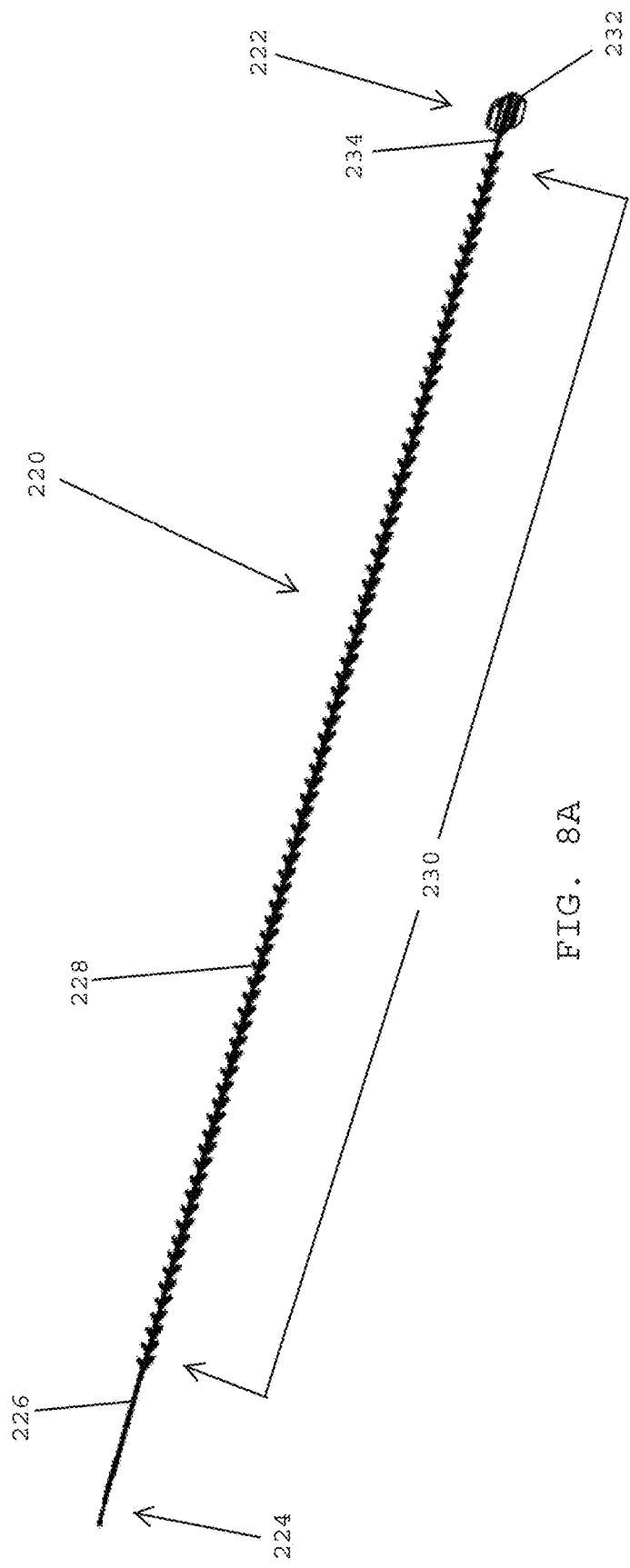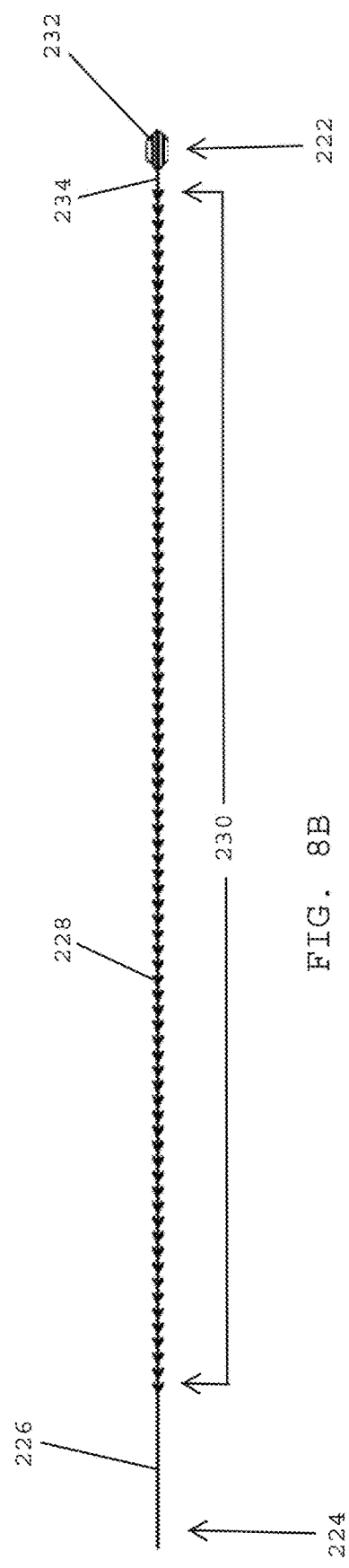

FIG. 25

| | Core Dimensions | Optimized Overbraiding Parameters | | | Notable Ratios |
|---|---|---|---|---|---|
| Size | Distance Between Barb Pairs (in) (DBBP) | Braiding Config. | Picks per Inch (PPI) | Inch per Pick (IPP) *Note: This is the inverse of PPI* | DBBP/IPP |
| 3-0 | 0.075 | 28D, 16C | 55 | 0.0182 | 4.13 |
| 2-0 | 0.075 | 56D, 12C | 50 | 0.0200 | 3.75 |
| 0 | 0.075 | 56D, 16C | 48 | 0.0208 | 3.60 |
| 1 | 0.075 | 80D, 16C | 41 | 0.0244 | 3.08 |

BRAIDED BARBED SUTURES HAVING BARBED MONOFILAMENT INSERTS WITH CONCAVE CORE PROFILES

CROSS-REFERENCE TO RELATED APPLICATIONS

The present patent application claims benefit of U.S. Provisional Application Ser. No. 63/039,656, filed on Jun. 16, 2020, the disclosure of which is hereby incorporated by reference herein. The present patent application is related to commonly assigned, U.S. patent application Ser. No. 17/336,680, filed on even date herewith, which claims benefit of U.S. Provisional Application Ser. No. 63/039,649, filed on Jun. 16, 2020, the disclosures of which are hereby incorporated by reference herein.

BACKGROUND OF THE INVENTION

Field of the Invention

The present patent application is generally related to medical devices, and is more particularly related to surgical sutures used for closing wounds.

Description of the Related Art

Surgical sutures are used to close wounds and surgical incisions, and to repair damaged muscles, vessels, and tissue. Typically, a needle is attached to one end of a surgical suture, and the needle is drawn through tissue to form one or more loops holding the tissue together. For conventional sutures, the suture is subsequently tied off in one or more knots so that the tissue will remain drawn together.

There have been a number of attempts directed to improving sutures. For example, U.S. Pat. No. 4,546,769 to Planck et al. discloses a suture including a jacket made of a tubular braided structure, such as non-crimped yarns, and a core located within the jacket containing crimped fibers. The jacket is formed by braiding the non-crimped yarns around the core, which provides a suture that is easier to bend and handle, and that makes better knots.

Although sutures are very effective for closing wounds, there are a number of challenges associated with using conventional sutures. Many of these challenges are directly related to the knots used to secure sutures in place. If the knots are not tied properly, defects may arise including slippage, knot breakage, and re-opening of the wound. In addition, using knots to secure sutures may distort tissue, restrict blood flow, increase the formation of scars, impede wound healing, and result in infection.

In response to the above-noted deficiencies associated with conventional sutures, sutures having barbs have been developed. Unlike conventional sutures, barbed sutures have projecting barbs that allow the suture to be used to close wounds, approximate tissue, tighten tissue, and attach prosthetic devices without using knots.

For example, U.S. Pat. No. 8,216,497, assigned to Ethicon, Inc., the disclosure of which is hereby incorporated by reference herein, teaches methods of creating a barbed suture. Referring to FIGS. 1 and 2, in one embodiment, a pre-formed ribbon of polymeric material having a cross-sectional profile is punched to form a barbed suture 50 having a core 52 that extends along the length of the barbed suture 50 and a plurality of barbs 54 that extend outwardly from opposite lateral sides of the core 52. The core 52 provides strength and flexibility to the barbed suture 50.

One problem associated with barbed sutures is that the barbs may delaminate or separate from the core, which leads to device failure. In response, braided barbed sutures having more durable barbs have been developed. U.S. Pat. No. 8,663,277 to Collier et al., assigned to Ethicon, Inc., the disclosure of which is hereby incorporated by reference herein, teaches a braided barbed suture that provides a 96% improvement in holding strength compared to a barbed suture that is not braided.

Traditionally, braided barbed sutures have been made by manually delivering a barbed insert into a braiding filament assembly. An operator must adhere to a complex series of steps including running a braider to form a first length of unbarbed suture, turning the braider off, positioning an end of the barbed insert at the braider eyelet where the filaments converge at the braid point, and then turning the braider back on and allowing the filaments to draw the barbed insert into the braid.

When using the above-described manual delivery method, an uneven braided sheath will typically form around the elongated core of the barbed suture insert due to vibration imparted from the braiding apparatus to the elongated core of the barbed suture insert. The vibration generated by the braiding equipment can result in the barbed suture insert whipping, twisting, getting caught in the filaments, or accumulating undesired rotation as it is drawn into the braider eyelet.

In order to overcome the above-noted problems resulting from vibration and in order to improve the quality of braided barbed sutures, there have been some efforts directed to improving control over the orientation of barbed suture inserts during braiding procedures. For example, U.S. Pat. Nos. 8,210,085, 8,733,223, and 9,206,535, assigned to Ethicon, Inc., the disclosures of which are hereby incorporated by reference herein, teach an automated system for making braided barbed sutures including a braiding filament assembly, and a guide assembly (e.g., a delivery cartridge) having a barbed suture insert dispenser opening defining a passageway for orienting a barbed suture insert. Referring to FIG. 3, the automated system is adapted to dispense a barbed suture insert 60 having barbs 62 from the dispenser opening of the guide assembly and into the braiding filament assembly for braiding a plurality of filaments 64 around the barbed suture insert for making a braided barbed suture 66. The passageway of the dispenser opening allows longitudinal movement of the barbed suture insert 60 relative to the passageway while simultaneously preventing twisting movement of the barbed suture insert relative to the passageway. The passageway includes an elongated slit having a greater width than height for accommodating the barbs 62 of the barbed suture insert 60.

A conventional braided barbed suture includes a combination of a barbed suture component and a braided sheath component. The barbed suture component includes an elongated core and barbs that project outwardly from the elongated core. The braided sheath component is formed around the elongated core of the barbed suture so that the barbs project outwardly beyond the braided sheath for engaging tissue. The composite core structure of the elongated core and the braided sheath formed around the elongated core forms the backbone of the braided barbed suture.

In the conventional braided barbed suture, the elongated core typically has a convex shaped cross-section that has a thickness or diameter that is about equal to or greater than the thicknesses of the respective barbs that project outwardly from the elongated core. When filaments are braided over the elongated core, the resultant combination of the elongated core and the braided sheath typically defines an outer diameter that is greater than the thicknesses of the respective barbs, which causes the backbone of the braided barbed suture to become stiff and wire-like, thereby reducing flexibility.

At present, braided barbed sutures have two different tensile strength breaking points, a first breaking point for the braided component that is wound around the core and a second breaking point for the core section of the barbed suture. If only one of the braided component or the core component breaks, the braided barbed suture may appear to an observer to remain intact in spite of the fact that the overall tensile strength of the device has been compromised.

In view of the above-noted deficiencies, there remains a need for improved braided barbed sutures that maintain flexibility.

There also remains a need for improved braided barbed sutures with cores having a reduced outer dimensions (e.g., reduced width, reduced height, reduced cross-sectional area) for allowing a greater proportion of the composite core to be comprised of the braided sheath (i.e., a high braided sheath to core ratio), allowing for a suture construction that has the benefits of a braided suture (e.g., handling, flexibility, compatibility with surgical instrumentation), while not being stiff and maintaining flexibility.

There is also a need for improved braided barbed sutures in which the primary source of the tensile strength and the handling properties for the suture are provided by the braided sheath portion rather than the core, whereby the core primarily serves as the anchor point for the barbs, but does not provide substantial strength for the braided barbed suture.

Moreover, there remains a need for improved braided barbed sutures that have a single breaking point for both the elongated core section and the braided section of the device.

Furthermore, there remains a need for improved braided barbed sutures that can be used for closing wounds in a robotic surgery environment in which robotic graspers, limited tactile feedback, and limited visualization all contribute to frustrations associated with the premature breakage of barbed sutures.

There also remains a need for improved braided barbed sutures having good flexibility and a single breaking point for use in the limited space that is present in a minimally invasive surgery (MIS) environment.

SUMMARY OF THE INVENTION

In one embodiment, a braided barbed suture preferably includes two components that are joined together, namely, a barbed monofilament insert and a braided sheath. In one embodiment, the barbed monofilament insert may include an elongated core (e.g., a monofilament), a plurality of barbs projecting outwardly from the elongated core, and an end effector (e.g., a knot-replacement feature) secured to a proximal end of the elongated core. The end effector may be a tab, a stop, or a loop. In one embodiment, the braided sheath may be wound around the elongated core of the barbed monofilament insert using an automated braiding machine, such as disclosed in commonly assigned U.S. Pat. Nos. 8,210,085; 8,733,223; and 9,206,535, the disclosures of which are hereby incorporated by reference herein.

In one embodiment, the elongated core of the barbed monofilament insert preferably has a reduced thickness, reduced diameter, and/or a reduced outer dimension relative to the thicknesses of the respective barbs that project outwardly from the elongated core. The thickness of the elongated core is desirably less than that found in conventional barbed monofilament inserts. The relatively smaller thickness of the elongated core desirably minimizes the cross-sectional dimension of the elongated core within the overbraided composite, which, after being enveloped by the braided sheath, maintains the flexibility of the braided barbed suture while the tensile strength for the braided barbed suture is provided primarily by the braided sheath.

In one embodiment, the braided sheath envelopes the elongated core and preferably extends along the majority of the length of the elongated core. In one embodiment, the combination of the elongated core and the braided sheath forms a flexible composite core of the braided barbed suture. Controlling the ratio of the thickness, diameter, and/or outer dimension of the elongated core relative to the thickness, diameter, and/or outer dimension of the braided sheath preferably provides the composite core of the braided barbed suture with greater tensile strength, and improved flexibility and handling characteristics than can be attained when using barbed suture inserts having elongated cores with normal thicknesses.

In one embodiment, when the backbone (i.e., the overbraided section) of the braided barbed suture is viewed in cross-section, the ratio of the thickness (e.g., the diameter) of the elongated core relative to the thickness (e.g., the diameter) of the composite core (i.e., the core to braided sheath ratio) is preferably less than one. Thus, the braided sheath portion of the braided barbed suture preferably comprises a larger cross-sectional area of the backbone of the braided barbed suture than does the elongated core, which enhances the tensile strength of the braided barbed suture via the braided sheath and improves flexibility due to the thinner than normal elongated core.

In one embodiment, when the braided sheath envelopes the elongated core to form the composite core of a braided barbed suture, the ratio of the thickness (e.g., diameter) of the elongated core relative to the aggregate thickness (e.g., aggregate diameter) of the composite core is between about 0.16 and 0.85, and more preferably between about 0.4 and 0.5.

In one embodiment, the reduced thickness of the elongated core enables a greater proportion of the composite core (i.e., the backbone of the braided barbed suture formed by winding the braided sheath around the elongated core) to be comprised of the braided sheath component, allowing for a braided barbed suture construction that has the benefits of a conventional braided suture such as handling, flexibility, and compatibility with surgical instruments.

In one embodiment, the elongated core of the barbed monofilament insert functions primarily as an anchor point for the barbs and the barbed monofilament insert is not the primary component that provides tensile strength for the braided barbed suture. Rather, the primary source of the tensile strength and the handling properties of the braided barbed suture are desirably provided by the braided sheath that is wound around the elongated core.

In one embodiment, the braided sheath component preferably improves the overall tensile strength of the braided barbed suture. At the same time, the reduced thickness of the elongated core of the barbed monofilament insert desirably minimizes the bulk of the elongated core and braided sheath combination along the backbone (i.e., spine) of the braided barbed suture, which preserves the flexible nature of the braided sheath and enhances the overall flexibility of the braided barbed suture. Thus, the braided barbed suture construction disclosed herein provides a balance between two features sought by surgeons, namely, tensile strength and flexibility. Moreover, the presence of barbs projecting outwardly from the elongated core and through the braided sheath allows surgeons to suture tissue without having to tie knots and without requiring a surgical assistant to maintain tension on the suture line.

In one embodiment, the barbed monofilament insert preferably includes a PDS monofilament core having a thickness or diameter ranging from 5 to 20 mil, and more preferably between 6 to 8 mil.

In one embodiment, the braided sheath preferably includes a VICRYL multifilament yarn. In one embodiment, after the braided sheath has been wound around the elongated core to form the composite core of a braided barbed suture, the composite core preferably has a thickness or outer diameter ranging from about 13 to 30 mil, and more preferably between about 13 to 18 mil.

In one embodiment, the braided barbed suture disclosed in the present patent application provides improved tensile strength and handling characteristics, which are highly desirable for suturing tissue in tightly confined spaces such as in minimally invasive surgery (MIS) environments. Historically, surgeons have had to make tradeoffs that forced them to use different suture products having different benefits and features. The braided barbed sutures disclosed herein provide the benefits of optimized strength, efficiency, handling, and flexibility in a single suture device.

In one embodiment, a braided barbed suture preferably includes a barbed monofilament insert including an elongated core and a plurality of barbs projecting outwardly from opposite sides of the elongated core, and a braided sheath surrounding the elongated core. The composite, over-braided sheath has a thickness (e.g., a diameter), whereby a ratio of the thickness or diameter of the elongated core relative to the thickness or diameter of the composite core is between about 0.16 to 091.

In one embodiment, the ratio of the thickness or diameter of the elongated core relative to the thickness or diameter of the composite core is between about 0.24 to 073.

In one embodiment, the barbed monofilament insert preferably includes the elongated core having a first thickness, and a first barb projecting outwardly from the elongated core, the first barb including an inner end having a second thickness that is greater than the first thickness of the elongated core and an outer end having a third thickness that is less than the second thickness of the inner end of the first barb. In one embodiment, the barbed monofilament insert preferably includes a transition zone that extends between the elongated core and the inner end of the first barb for connecting the inner end of the first barb with the elongated core.

In one embodiment, the transition zone is thinner adjacent the elongated core and is thicker adjacent the inner end of the first barb. In one embodiment, the transition zone widens from the elongated core to the inner end of the first barb.

In one embodiment, first and second transition zones may be located on opposite sides of an elongated core of a barbed monofilament insert. The first and second transition zones and a top surface of the elongated core may define a first concave profile that is located at a top side of the barbed monofilament insert, and the first and second transition zones and a bottom surface of the elongated core may define a second concave profile that is located at a bottom side of the barbed monofilament insert.

In one embodiment, the braided sheath preferably includes fibers that are wound around both the elongated core and the transition zones of the barbed monofilament insert to form the composite core of the braided barbed suture.

In one embodiment, after the braided sheath is wound around the elongated core, the barbs project outwardly beyond an outer perimeter of the braided sheath.

In one embodiment, a braided barbed suture preferably has a single breaking point for both the braided sheath component and the barbed monofilament insert component.

In one embodiment, the elongated core has a convexly curved top surface and a convexly curved bottom surface.

In one embodiment, the elongated core has a substantially flat top surface and a substantially flat bottom surface.

In one embodiment, the plurality of barbs on a braided barbed suture preferably include pairs of barbs that extend along the length of the device. In one embodiment, each pair of barbs preferably defines a barb tip-to-tip distance (BTTD). In one embodiment, the composite core has a composite core diameter (CCD), and a ratio of the barb tip-to-tip distance (BTTD) to said composite core diameter (CCD) is between about 1.92-4.5.

In one embodiment, the ratio of the barb tip-to-tip distance (BTTD) to the composite core diameter (CCD) is between about 2.5-3.8.

In one embodiment, a braided barbed suture preferably includes a barbed monofilament insert including an elongated core having a thickness or diameter and a plurality of barbs projecting outwardly from opposite sides of the elongated core, and a braided sheath surrounding the elongated core, The combination of the elongated core and the braided sheath preferably form a composite core of the braided barbed suture, whereby the elongated core is located in a center of the composite core and the braided sheath surrounds the elongated core. The aggregate thickness of the composite core, which is a combination of the elongated core and the braided sheath enveloping the elongated core, is preferably greater than the thickness of the elongated core. In one embodiment, a ratio of a thickness or diameter of the elongated core relative to a thickness or diameter of the composite core is between about 0.16 to 0.91, and more preferably between about 0.40 to 0.50.

In one embodiment, the elongated core has a concave profile, and the elongated core is thinner than inner ends of the barbs that project outwardly from opposite sides of the elongated core.

In one embodiment, a braided barbed suture may include a first transition zone located between a first lateral side of the elongated core and an inner end of a first barb, whereby the first transition zone widens from the first lateral side of the elongated core to the inner end of the first barb, and a second transition zone located between a second lateral side of the elongated core and an inner end of a second barb, whereby the second transition zone widens from the second lateral side of the elongated core to the inner end of the second barb.

In one embodiment, the braided barbed suture preferably includes an end effector coupled with the elongated core. In one embodiment, the elongated core desirably extends through the end effector.

In one embodiment, the end effector preferably includes a first wing that extends laterally from a first lateral side of the elongated core and a second wind that extends laterally from a second lateral side of the elongated core. The first and second wings are preferably thicker than the elongated core.

In one embodiment, a braided barbed suture preferably includes a barbed monofilament insert including an elongated core having a concave profile and a plurality of barbs projecting outwardly from opposite sides of the elongated core, whereby the barbs have inner ends that are thicker than the elongated core. In one embodiment, the barbed monofilament insert preferably includes at least one transition zone located between the elongated core and the inner ends of at least some of the barbs. In one embodiment, a braided sheath is wound around the elongated core and the at least one transition zone to form a composite core of a braided barbed suture, whereby a ratio of the thickness or diameter of the elongated core relative to the thickness or diameter of the composite core is between about 0.16 to 0.91, and more preferably about 0.24 to 0.73.

In one embodiment, the barbed monofilament insert including the elongated core and the barbs may be formed from a barbed suture blank, such as a ribbon of polymeric material. In one embodiment, the barbed suture blank preferably has a cross sectional shape having an elongated core (e.g., a concave core, a core with flat or rounded top and bottom surfaces) and first and second lateral wing sections that are located on opposite sides of the elongated core. In one embodiment, the first and second lateral wing sections may be punched and/or cut (e.g., using a die) to form barbs that project outwardly from the elongated core and an end effector that is secured to a proximal end of the elongated core. In one embodiment, the elongated core preferably has a thickness that is less than the thicknesses of the first and second lateral wing sections that are punched in the barbed suture blank to form the barbs and the end effector.

In one embodiment, a braided barbed suture preferably includes an elongated core having a proximal end, a distal end, and a non-round cross-section. In one embodiment, the non-round cross-section of the elongated core preferably has a first thickness located in a center of the elongated core, a first lateral side with a first lateral side thickness, a second lateral side with a second lateral side thickness. The central section having the first thickness is located between the first and second lateral sides of the core. In one embodiment, the center of the elongated core is thicker than the first and second lateral sides of the elongated core.

In one embodiment, the elongated core has flat top and bottom surfaces with a constant thickness at a center region and at first and second lateral sides of the elongated core that bound the center region.

In one embodiment, the barbed monofilament insert that is used to make the braided barbed suture preferably includes a transition zone that is located between the thinner elongated core and the thicker barbs, which allows for over-braiding to a full core width and height without substantially extending into the barbs, thereby providing for a more flexible backbone (i.e., the composite of the elongated core and the braided sheath) while enhancing tensile strength via the braided sheath that surrounds the elongated core. In one embodiment, the transition zone widens and/or becomes thicker between a lateral side of the elongated core and the inner ends of the barbs to provide a smooth transition surface between the thinner elongated core and the thicker barbs.

In one embodiment, the transition zone provides a relief area between the elongated core and the barbs that accommodates a multifilament braided sheath that is wound around the elongated core, whereby the fibers of the multifilament braided sheath do not encapsulate and/or bury the barbs, which would limit their functionality.

In one embodiment, the elongated core, having a reduced thickness, diameter, and/or cross-sectional area, is preferably over-braided with the braided sheath for producing a braided barbed suture that predominantly exhibits the mechanical properties of a multifilament suture.

In one embodiment, the braided barbed suture is constructed to control the ratio of the multifilament sheath material relative to the monofilament core material In one embodiment, making braided barbed sutures having a predetermined elongated core to braided sheath ratio allows for the braided barbed suture device to make full use of the uniaxial tensile strength provided by the braided sheath without having the strength of the braided barbed suture reduced by tying a knot.

In one embodiment, making braided barbed sutures having an appropriate elongated core to braided sheath ratio enables the composite braided barbed suture device to closely replicate the bending stiffness of a traditional multifilament suture to provide handling characteristics that provide benefits in a minimally invasive surgical environment where space and visualization are limited (e.g., robotic surgery).

In one embodiment, a braided barbed suture preferably includes a composite structure including a barbed monofilament insert with an elongated core having a first tensile strength and a braided sheath that envelopes the elongated core having a second tensile strength. In one embodiment, the combined tensile strengths are equal to or greater than either the first tensile strength of the elongated core and the second tensile strength of the braided sheath.

In one embodiment, the braided barbed suture preferably includes both a braided sheath component and a barbed monofilament insert component having an elongated core whereby the two components have a combined breaking strength value that is greater than either of the components individually and where the point of tensile failure of the composite braided barbed suture and of each of the components in the composite structure is substantially the same. Providing a braided barbed suture having a single breaking point for both the braided sheath component and the elongated core of the barbed monofilament insert component preferably minimizes the sensation of two separate failure points when the suturing device is under tension.

Multifilament sutures offer high strength, good damage resistance, and desirable handling characteristics, but do not inherently lend themselves to being processed as a monofilament or to having barbed suture features due to the nature of the polymeric materials that are typically used. Monofilament sutures can be made with barbs, however, monofilament sutures are susceptible to damage if not properly handled with surgical instrumentation.

The braided barbed suture disclosed herein provides a suture construction that has the benefits of a braided, multifilament suture (e.g., handling, flexibility, damage resistance, compatibility with surgical instrumentation) balanced with the strength of a monofilament suture, while avoiding the sensation of two separate tensile failure points. The composite braided barbed suture preferably has a braided sheath and an elongated core that fail in tension at essentially the same time, which minimizes the sensation of two separate points of tensile failure.

In one embodiment, the elongated core component of the braided barbed suture functions primarily as the anchor point for the barbs. In one embodiment, the braided sheath component of the braided barbed suture, rather than the elongated core component, functions as the primary source of the tensile strength and the handling properties for the braided barbed suture.

When comparing monofilament sutures to multifilament sutures, the multifilament sutures tend to have greater straight tensile strength due to the braid construction that is present in the multifilament sutures, which allows for load distribution and uniaxial elongation of the device. However, in clinical applications, the tensile strengths of traditional multifilament and monofilament sutures are inherently reduced to the strength of the knots that can be tied. In comparison, barbed sutures eliminate the need for knot tying and can therefore leverage the straight tensile strength as the relevant wound holding value.

BRIEF DESCRIPTION OF THE DRAWINGS

FIG. 5A is a perspective view of a barbed monofilament insert that is formed from the barbed suture blank shown in FIGS. 4A-4E, the barbed monofilament insert including an elongated core, a plurality of barbs, and an end effector, in accordance with one embodiment of the present patent application.

FIG. 5B is a top view of the barbed monofilament insert shown in FIG. 5A.

FIG. 5C-1 is a perspective view of the midsection of the barbed monofilament insert shown in FIG. 5C.

FIG. 5D-1 is a perspective view of the proximal end of the barbed monofilament insert shown in FIGS. 5A, 5B and 5D.

FIG. 8A is a perspective view of a barbed monofilament insert made from the barbed suture blank shown in FIGS. 7A-7E, in accordance with one embodiment of the present patent application.

FIG. 8B is a top view of the barbed monofilament insert shown in FIG. 8A.

FIG. 8C-1 is a perspective view of the midsection of the barbed monofilament insert shown in FIG. 8C.

FIG. 8D-1 is a perspective view of the proximal end of the barbed monofilament insert shown in FIG. 8D.

FIG. 25 is a chart showing optimized over-braiding parameters to be used with the automated braiding system of FIG. 18 controlling the number of picks in a braided sheath of a braided barbed suture, in accordance with one embodiment of the present patent application.

DETAILED DESCRIPTION OF PREFERRED EMBODIMENTS

Definitions

Figure 1:
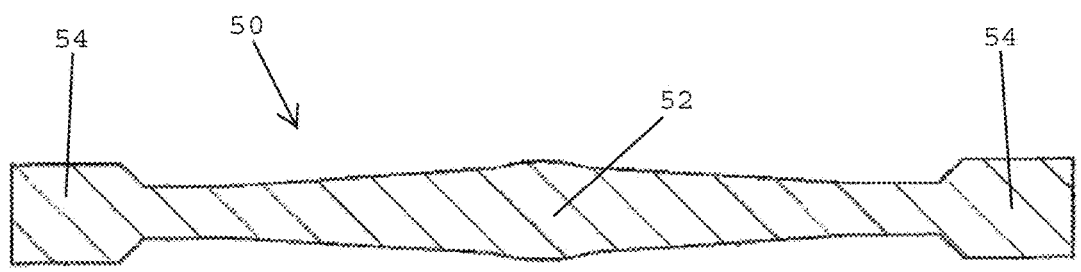
FIG. 1 is a cross-sectional view of a prior art barbed suture insert having an elongated core and barbs that project outwardly from opposite lateral sides of the elongated core.
Figure 2:
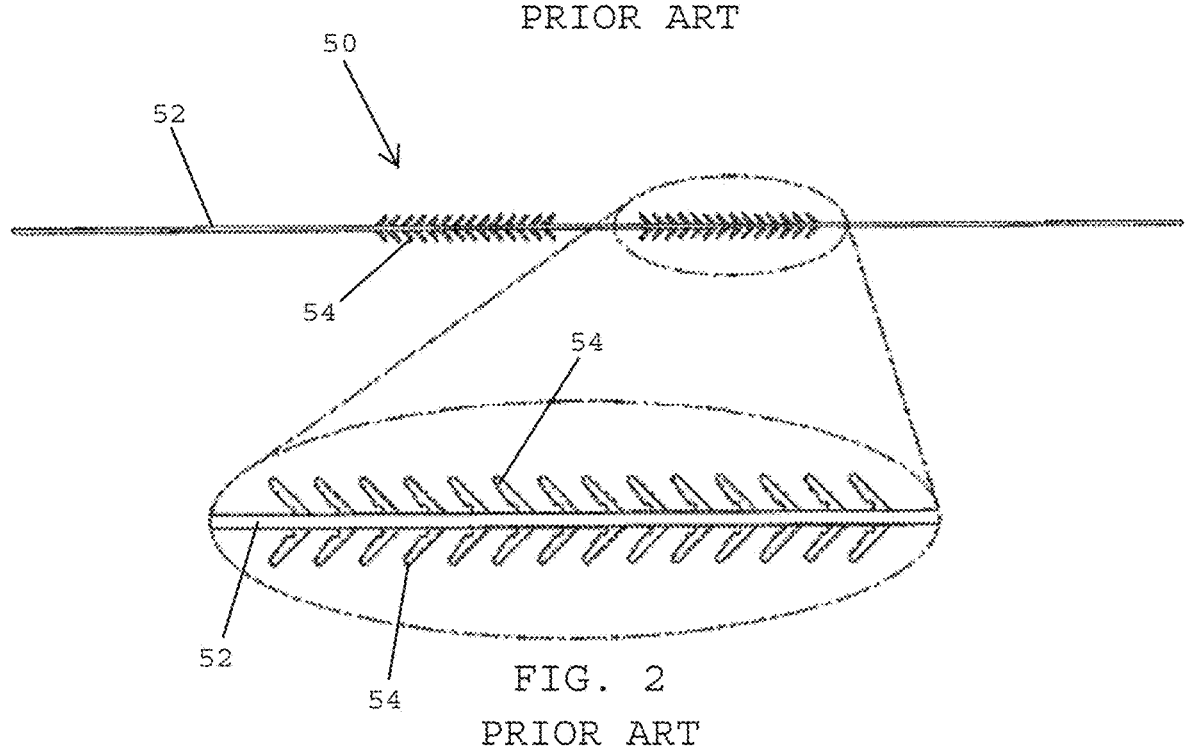
FIG. 2 is a top view of the prior art barbed suture insert shown in FIG. 1, the barbed suture insert having an elongated core, a first set of barbs that extend toward a first end of the elongated core, and a second set of barbs that extend in an opposite direction toward a second end of the elongated core.

Barbed Monofilament Insert. A first component of a braided barbed suture. The barbed monofilament insert includes an elongated core having a proximal end and a distal end. The distal end of the elongated core may also be referred to as a leader end, which is the end of the elongated core that is attached to a needle. The barbed monofilament insert has a plurality of barbs that project outwardly from opposite sides of the elongated core to define a barbed section of the barbed monofilament insert. An end effector is secured to the proximal end of the elongated core, and a connector section of the elongated core is located between the end effector and the barbed section.

Composite Core. A section of a braided barbed suture that includes the elongated core of the barbed monofilament insert with barbs projecting outwardly from opposite lateral sides of the elongated core, and a braided sheath surrounding the elongated core. The composite core is the combination of the elongated core and the braided sheath that envelopes the elongated core. The composite core has a thickness that is greater than the thickness of the elongated core.

Denier. A Denier (D) is a unit of measure for the linear mass density of fibers. It is the mass in grams per 9,000 meters of the fiber. The Denier unit of measure is based on a natural reference, namely, a single strand of silk is approximately one denier, or a 9,000 meter long strand of silk weighs about one gram. The Denier unit is calculated as follows, 1 Denier=1 g/9,000 m=0.11 mg/m.

Lateral Width. The distance between a first line parallel to the central axis of the elongated core, which is adjacent the closest outer lateral edge of a barb extending from a first side of the elongated core and a second line parallel to the central axis of the elongated core, which is adjacent the closet outer lateral edge of a barb extending from a second side of the elongated core.

Leader End. A non-barbed zone of an elongated core of a barbed monofilament insert. The leader end forms the distal end or needle attachment end of the elongated core of the barbed monofilament insert. Filaments may be wound around the leader end of the elongated core to form a section of the composite core.

Elongated Core Thickness. The barbs of a barbed monofilament insert project outwardly from opposite sides of the elongated core. The barbs lie within a first plane. A thickness measurement of the elongated core that is taken along an axis that lies within a second plane that is perpendicular to the first plane defined by the barbs. In one embodiment, the elongated core thickness is an average of three separate thickness measurements made at the leader end of the barbed monofilament insert. A gauge may be used to record the thickness measurements of the elongated core. The elongated core thickness may also be referred to as the elongated core diameter.

Composite Core Diameter. The composite core diameter is a measurement of an outer diameter of a braided sheath that envelopes an elongated core of a barbed monofilament insert. The composite core diameter is measured within a plane that is perpendicular to the longitudinal axis of the elongated core.

Composite Core Thickness. A thickness measurement of the composite core that is taken along the axis that lies within the second plane that is perpendicular to the first plane defined by the barbs. In one embodiment, the composite core thickness is an average of three separate thickness measurements made at the leader end of the braided barbed suture. A gauge may be used to record the thickness measurements of the composite core. The composite core thickness may also be referred to as the composite core diameter.

Thickness Ratio. The thickness ratio of a braided barbed suture is a ratio of the elongated core thickness relative to the composite core thickness.

Figure 4A:
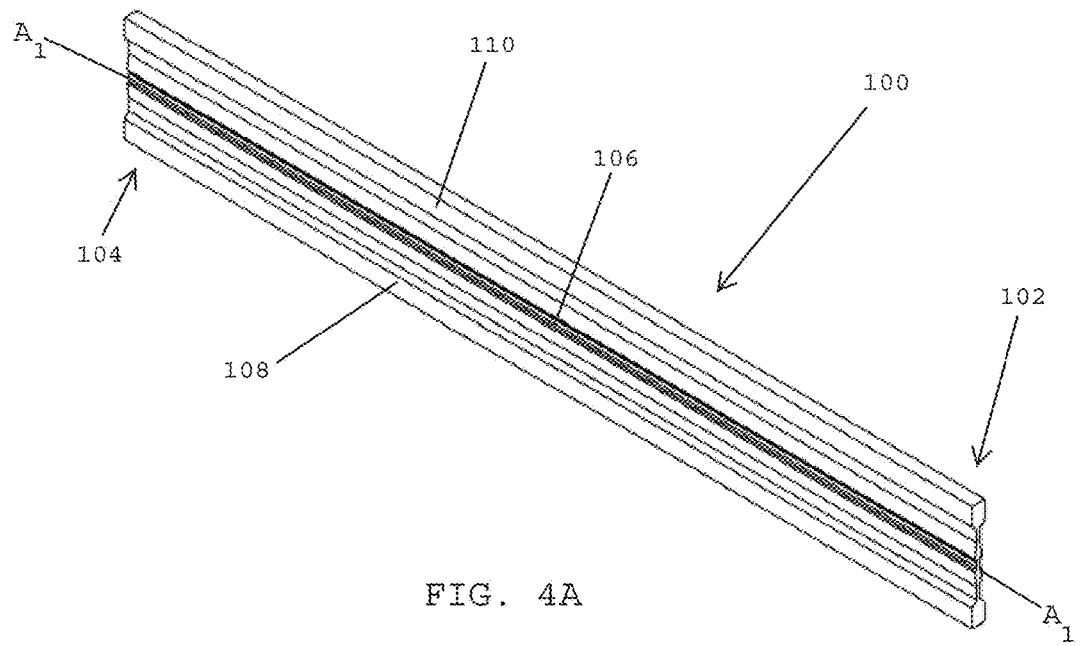
FIG. 4A is a perspective view of a barbed suture blank that is used to make a barbed monofilament insert, in accordance with one embodiment of the present patent application.
Figure 4B:
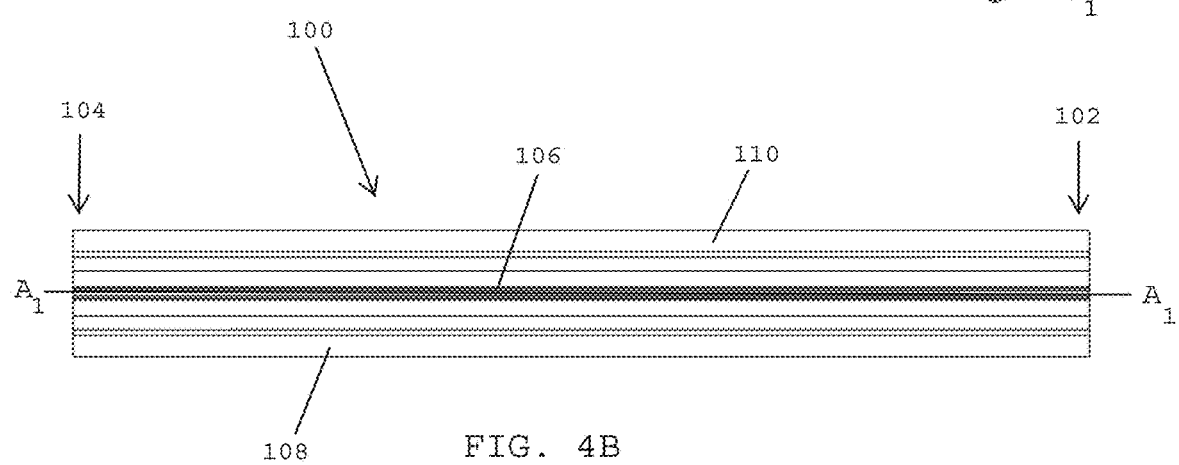
FIG. 4B is a top view of the barbed suture blank shown in FIG. 4A.
Figure 4C:
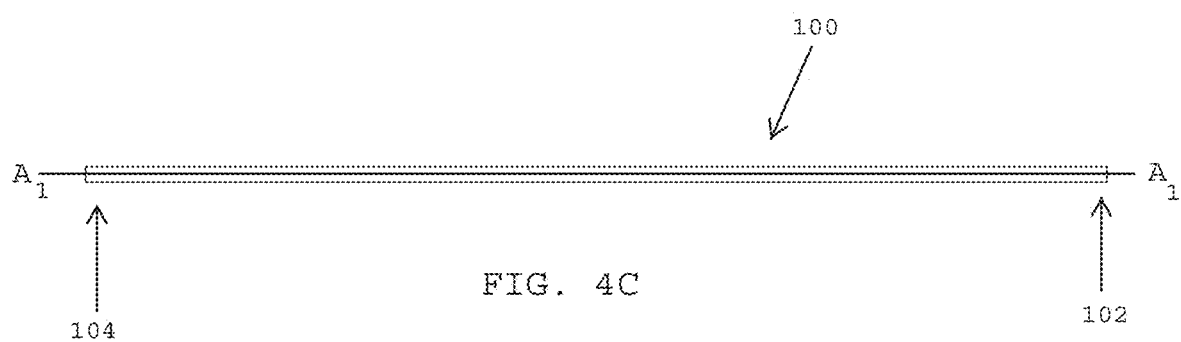
FIG. 4C is a side view of the barbed suture blank shown in FIGS. 4A and 4B.

Referring to FIGS. 4A-4C, in one embodiment, a barbed suture blank 100, such as a ribbon of a polymeric material, may be used to form a barbed monofilament insert having an elongated core and a plurality of barbs that project laterally from opposite sides of the elongated core. In one embodiment, the barbed suture blank 100 preferably includes a proximal end 102, a distal end 104, and a longitudinal axis $A_1$ that extends along the length of the barbed suture blank and between the proximal and distal ends 102, 104 thereof.

In one embodiment, the barbed suture blank 100 preferably includes an elongated core 106 that extends along the longitudinal axis $A_1$, a first lateral section 108 that extends along a first lateral side of the elongated core 106, and a second lateral section 110 that extends along a second lateral side of the elongated core 106. The first and second lateral sections 108, 110 may be punched out or cut during the forming of barbs and/or an end effector.

Figure 4D:
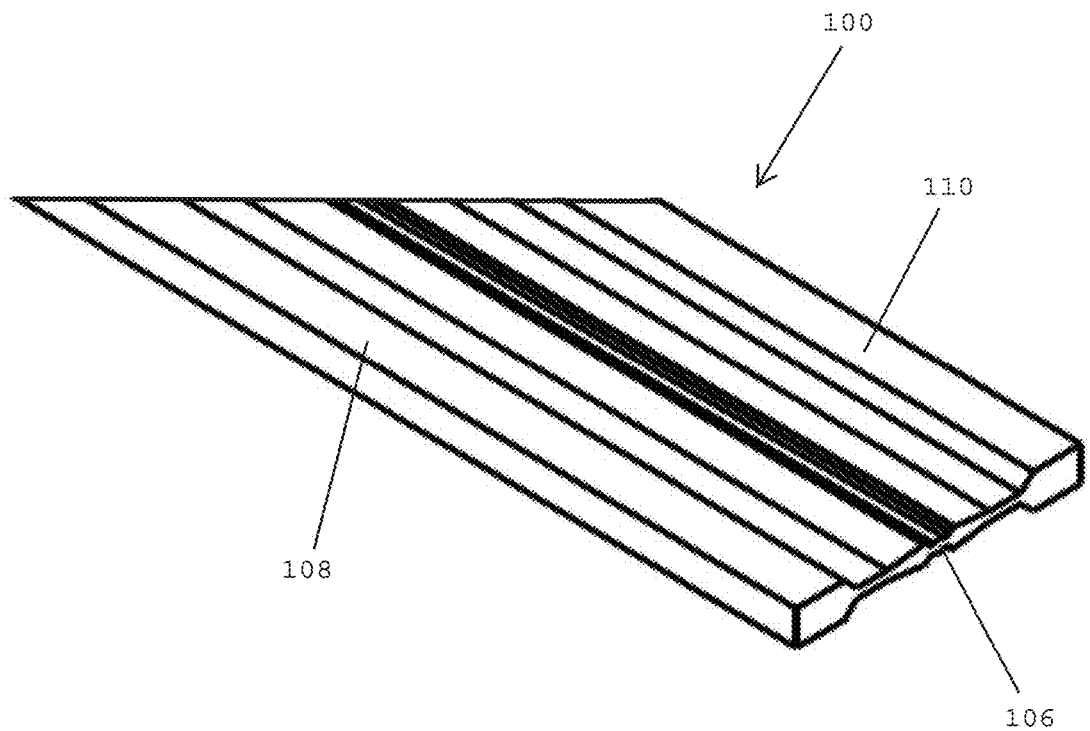
FIG. 4D is a perspective view of a proximal end of the barbed suture blank shown in FIGS. 4A-4C.
Figure 4E:
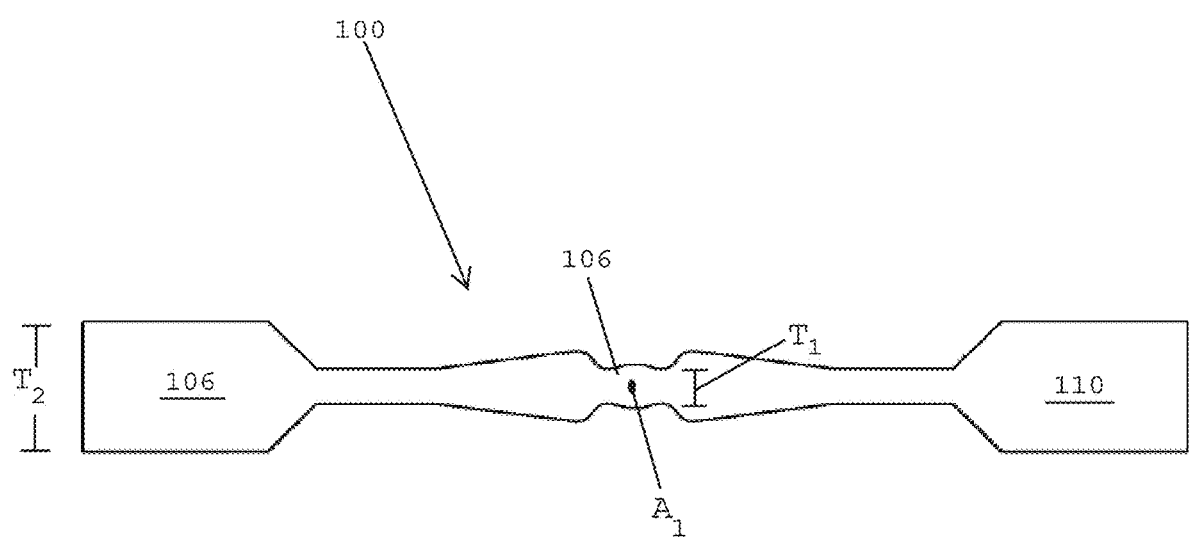
FIG. 4E is a cross-sectional view of the barbed suture blank shown in FIG. 4B.

Referring to FIGS. 4D and 4E, in one embodiment, the barbed suture blank 100 preferably has a pre-formed cross-sectional shape, which desirably includes the elongated core 106 and the first and second lateral sections 108, 110 that are located on opposite sides of the elongated core 106. In one embodiment, the elongated core 106 is preferably located in the center of the barbed suture blank 100 and extends along the longitudinal axis $A_1$ of the barbed suture blank 100. Referring to FIG. 4E, in one embodiment, the elongated core 106 has a first thickness $T_1$ that is less than the second thicknesses $T_2$ of the respective first and second lateral sections 108, 110 of the barbed suture blank 100.

In one embodiment, the barbed suture blank 100 may be placed into a die or punch for forming a barbed monofilament insert including an elongated core, a plurality of barbs projecting outwardly from the elongated core, and an end effector (e.g., a stop) connected with a proximal end of the elongated core. In one embodiment, the elongated core is integrally connected with the barbs and the end effector.

Referring to FIGS. 5A and 5B, in one embodiment, the barbed suture blank 100 (FIGS. 4A-4E) is desirably punched or cut to form a barbed monofilament insert 120 having a proximal end 122 and a distal end 124. In one embodiment, the barbed monofilament insert 120 desirably includes an elongated core 126 (e.g., a monofilament) that extends along the length of the barbed suture. The barbed monofilament insert 120 desirably includes a plurality of barbs 128 that extend outwardly from opposite sides of the elongated core 126 to define a barbed midsection 130 of the barbed monofilament insert 120. The barbed monofilament insert 120 desirably includes an end effector 132 (e.g., a stop) that is secured to a proximal end of the elongated core 126, and which is located at the proximal end 122 of the barbed monofilament insert 120. In one embodiment, the elongated core 126 of the barbed monofilament insert 120 desirably includes a connector section 134 that secures the end effector 132 with the proximal end of the elongated core 126. In one embodiment, the elongated core 126 and the connector section 134 are integrally formed with one another.

In one embodiment, the elongated core 126 of the barbed monofilament insert 120 preferably has a cross-sectional shape that is similar to the shape of the elongated core 106 of the barbed suture blank 100 that is shown and described above in FIG. 4E. In one embodiment, the elongated core 126 preferably has a thickness that is less than or equal to the thicknesses of the respective barbs 128 that project outwardly from opposite sides of the elongated core 126.

Figure 5C:
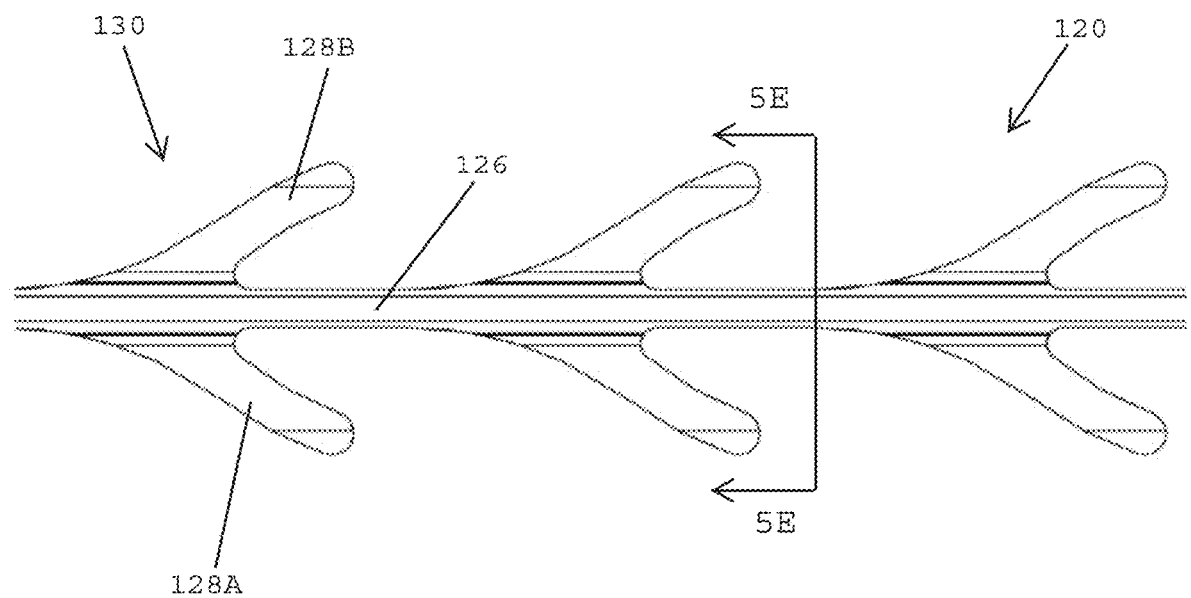
FIG. 5C is a magnified view of a midsection of the barbed monofilament insert shown in FIGS. 5A and 5B.
Figures 1, 5C:
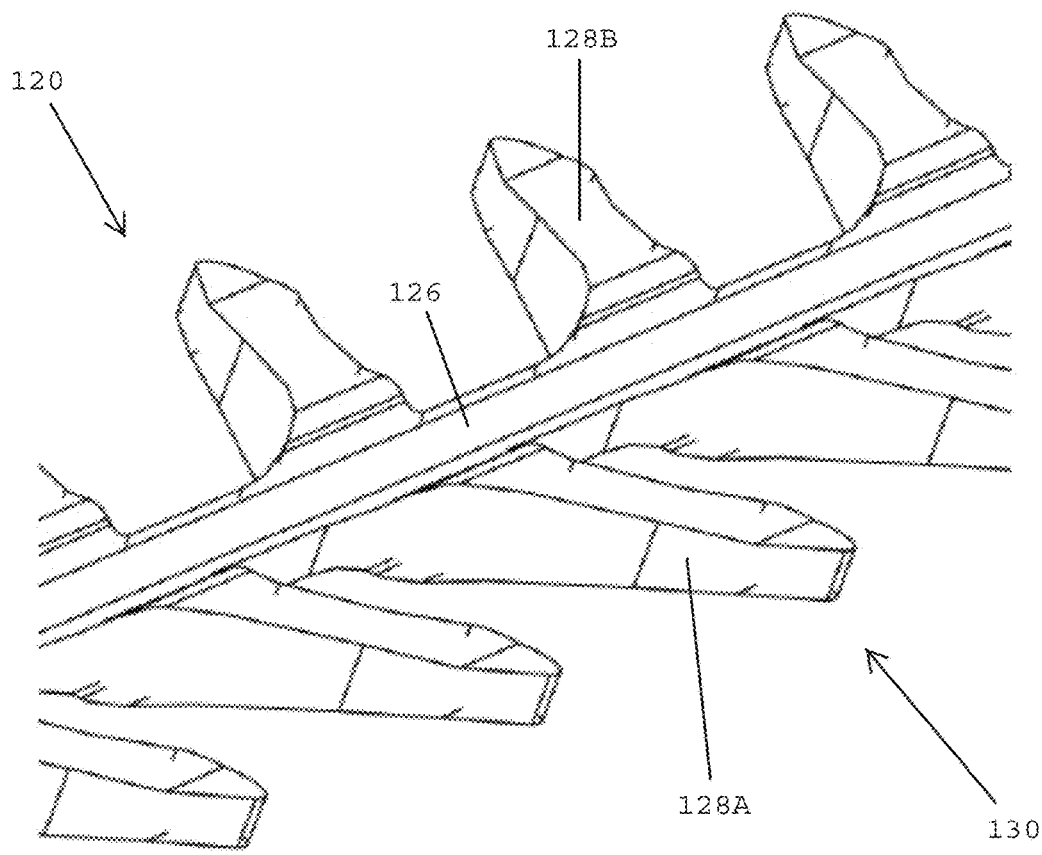

Referring to FIGS. 5O and 5C-1, in one embodiment, the barbed monofilament insert 120 desirably includes first barbs 128A that project outwardly from a first lateral side of the elongated core 126, and second barbs 128B that project outwardly from a second lateral side of the elongated core 126. As will be described in more detail herein, the elongated core 126 of the barbed monofilament insert 120 has a thickness that is preferably less than or equal to the thicknesses of the respective first and second barbs 128A, 128B that project outwardly from opposite lateral sides of the elongated core 126. Providing a barbed monofilament insert 120 having an elongated core 126 with a thickness that is less than or equal to the thicknesses of the respective 128A, 128B barbs will preferably reduce the overall dimension of a braided barbed suture comprised of the elongated core and a braided sheath that surrounds the elongated core, thereby maintaining the flexibility of a braided barbed suture 120 after the braided sheath has been formed around the elongated core 126.

Figure 5D:
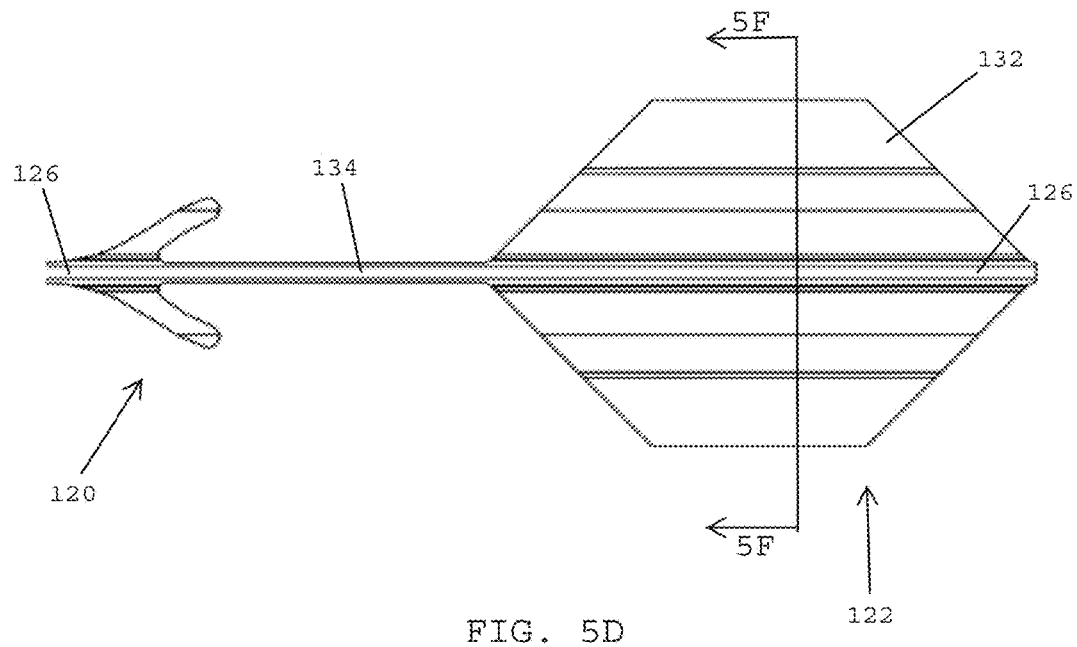
FIG. 5D is a magnified view of the proximal end of the barbed monofilament insert shown in FIGS. 5A and 5B.
Figures 1, 5D:
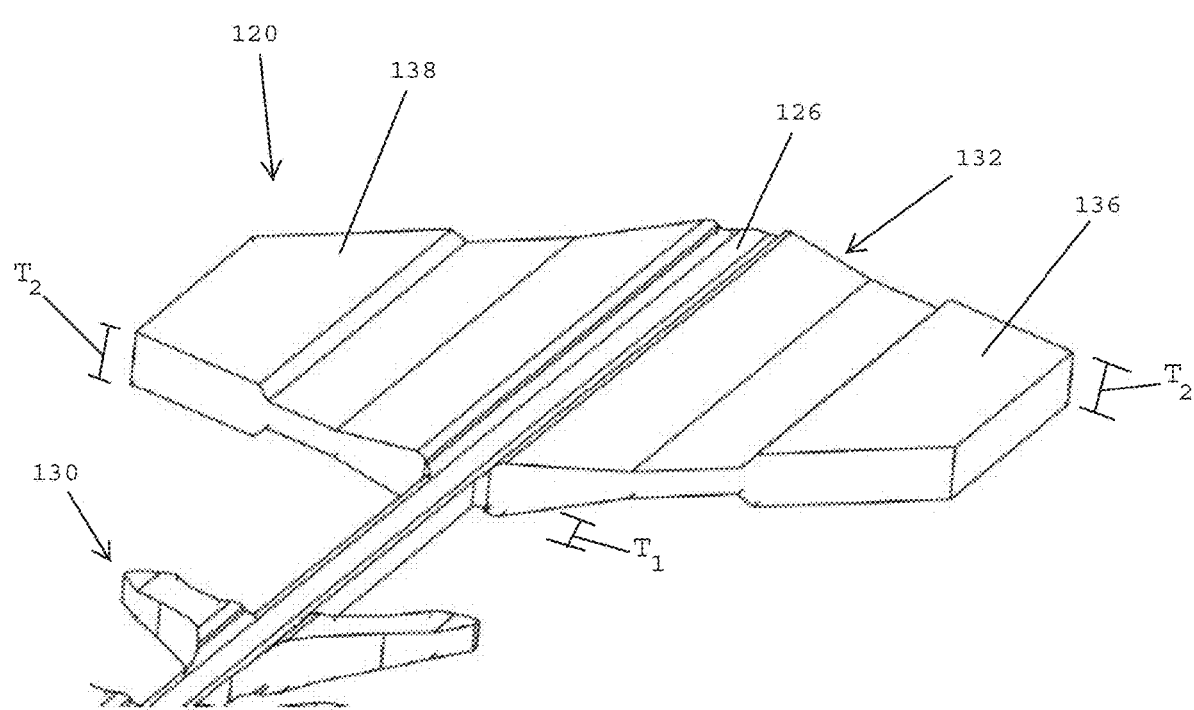

Referring to FIGS. 5D and 5D-1, in one embodiment, the barbed monofilament insert 120 preferably includes the end effector 132 (e.g., a stop) that is secured to a proximal end of the elongated core 126 at the proximal end 122 of the barbed monofilament insert 120. In one embodiment, the barbed monofilament insert 120 preferably includes a connector section 134 of the elongated core 126 that enables the barbed midsection 130 (FIG. 5A) of the barbed monofilament insert 120 to pass through a first track of a guide cartridge, the end effector 132 to pass through a second track of a guide cartridge, and the connector section 134 to pass through a slot that interconnects the first and second tracks of the guide cartridge as disclosed in commonly assigned, U.S. patent application Ser. No. 17/336,680, filed on even date herewith, which claims benefit of U.S. Provisional Application Ser. No. 63/039,649, filed on Jun. 16, 2020, the disclosure of which is hereby incorporated by reference herein.

In one embodiment, the elongated core 126 preferably extends through the barbed section 130 of the barbed monofilament insert 120, as well as through the end effector 132 that is located at the proximal end 122 of the barbed monofilament insert 120. As shown in FIG. 5D-1, the elongated core 126 has a thickness $T_1$ that is less than the respective thicknesses $T_2$ of first and second lateral wings 136, 138 of the end effector 132.

Figure 5E:
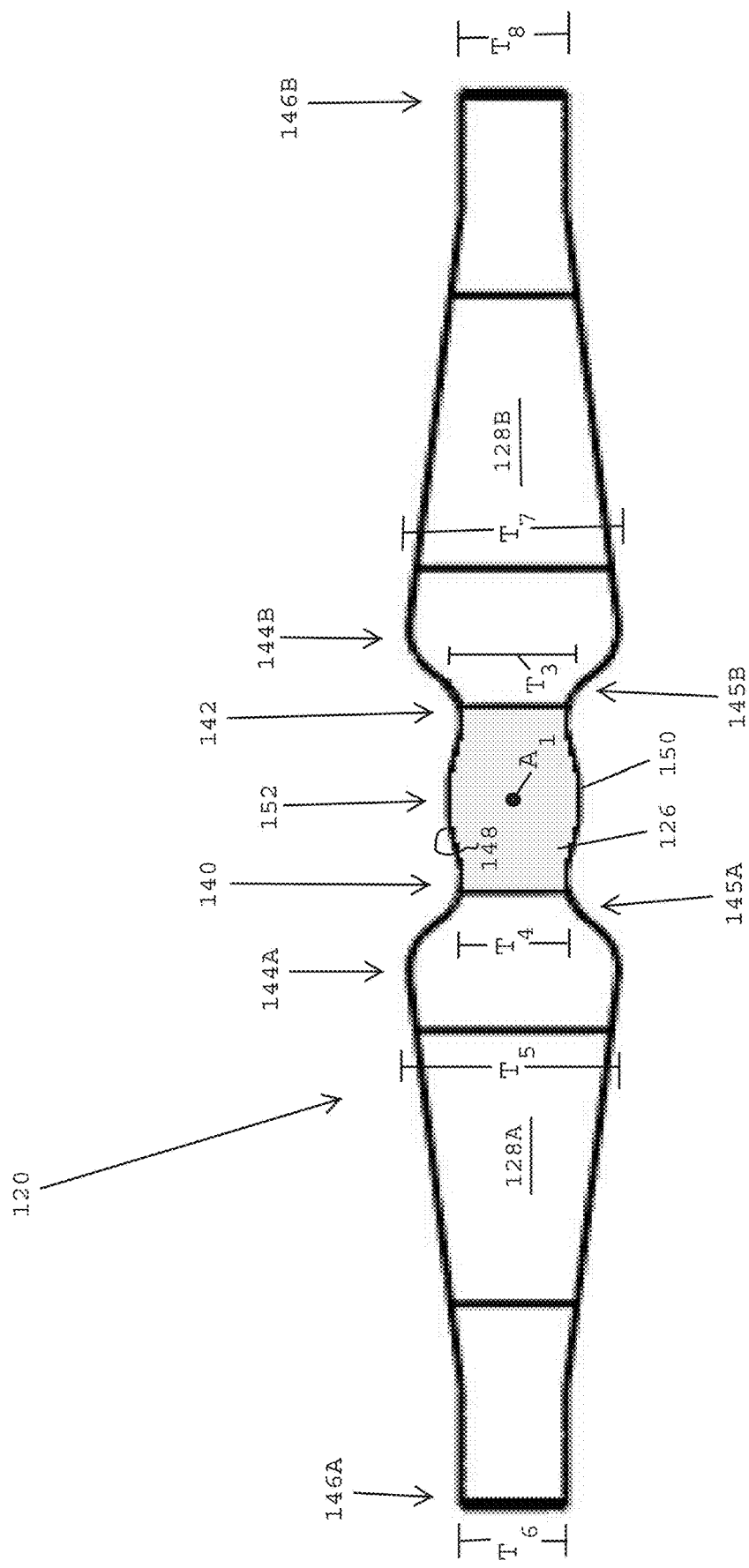
FIG. 5E is a cross-sectional view of the barbed monofilament insert shown in FIG. 5C.

Referring to FIG. 5E, in one embodiment, the barbed monofilament insert 120 preferably includes first barbs 128A that project outwardly from a first lateral side 140 of the elongated core 126 and second barbs 128B that project outwardly from a second lateral side 142 of the elongated core 126. In one embodiment, the elongated core 126 is preferably located at the center of the barbed monofilament insert 120 and extends along the longitudinal axis $A_1$ of the barbed suture. In one embodiment, the elongated core 126 preferably forms a flexible backbone that provides flexibility to the barbed monofilament insert during a suturing operation.

In one embodiment, the first barb 128A preferably has an inner end 144A that is connected with the first lateral side 140 of the elongated core 126 via a first transition zone 145A, and an outer end 146A that defines a free end of the first barb. The first transition zone 145A is located between the first lateral side 140 of the elongated core 126 and the inner end 144A of the first barb 128A. In one embodiment, the first transition zone 145A widens out or becomes thicker between the first lateral side 140 of the elongated core 126 and the inner end 144A of the first barb 128A.

The second barb 128B preferably has an inner end 144B that is connected with the second lateral side 142 of the elongated core 126 via a second transition zone 145B, and an outer end 146B that defines a free end of the second barb. The second transition zone 145B is preferably located between the second lateral side 142 of the elongated core 126 and the inner end 144B of the second barb 128B. In one embodiment, the second transition zone 145B widens out or becomes thicker between the second lateral side 140 of the elongated core 126 and the inner end 144B of the second barb 128B.

In one embodiment, the elongated core 126 preferably has a convex top surface 148 that is located on a top side of the barbed monofilament insert 120 and a convex bottom surface 150 that is located on a bottom side of the barbed suture. In one embodiment, a central region 152 of the elongated core 126 defines a thickness $T_3$ that is greater than the thicknesses $T_4$ at the respective first and second lateral sides 140, 142 of the elongated core 126.

In one embodiment, the top surface 148 of the elongated core and the first and second transition zones 145A, 145B preferably define a first concave profile that is located on a top side of the barbed monofilament inert 120, and the bottom surface 150 of the elongated core 126 and the first and second transition zones 145A, 145B preferably define a second concave profile that is located on a bottom side of the barbed monofilament insert.

In one embodiment, the first barb 128A has an inner end 144A defining a thickness $T_5$ and an outer free end 146A defining a thickness $T_6$ that is less than the thickness $T_5$, thereof. As a result, the inner end 144A of the first barb 128A is thicker than the outer end 146A of the first barb 128A. In one embodiment, the thickness $T_3$ at the central region 152 of the elongated core 126 and the thicknesses $T_4$ at the respective first and second lateral sides 140, 142 of the elongated core 126 are less than the thickness $T_5$ at the inner end 144A of the first barb 128A, and less than or equal to the thickness $T_6$ at the outer end 146A of the first barb 128A. The first transition zone 145A widens and/or becomes thicker between the thinner first lateral side 140 of the elongated core 126 and the inner end 144A of the first barb 128A.

In one embodiment, the second barb 128B is preferably thicker at the inner end 144B thereof and thinner at the outer free end 146B thereof. In one embodiment, the inner end 144B of the second barb 128B has a thickness $T_7$ and the outer end 146B of the second barb 128B has a thickness $T_8$ that is less than the thickness $T_7$ of the inner end 144B. In one embodiment, the thickness $T_3$ at the central region 152 of the elongated core 126 and the thicknesses $T_4$ at the first and second lateral sides 140, 142 of the elongated core 126 are less than the thickness $T_7$ at the inner end 144B of the second barb 128B and less than or equal to the thickness $T_8$ at the outer end 146B of the second barb 128B. The second transition zone 145B widens and/or becomes thicker between the second lateral side 142 of the elongated core 126 and the inner end 144B of the second barb 128B.

Figure 5F:
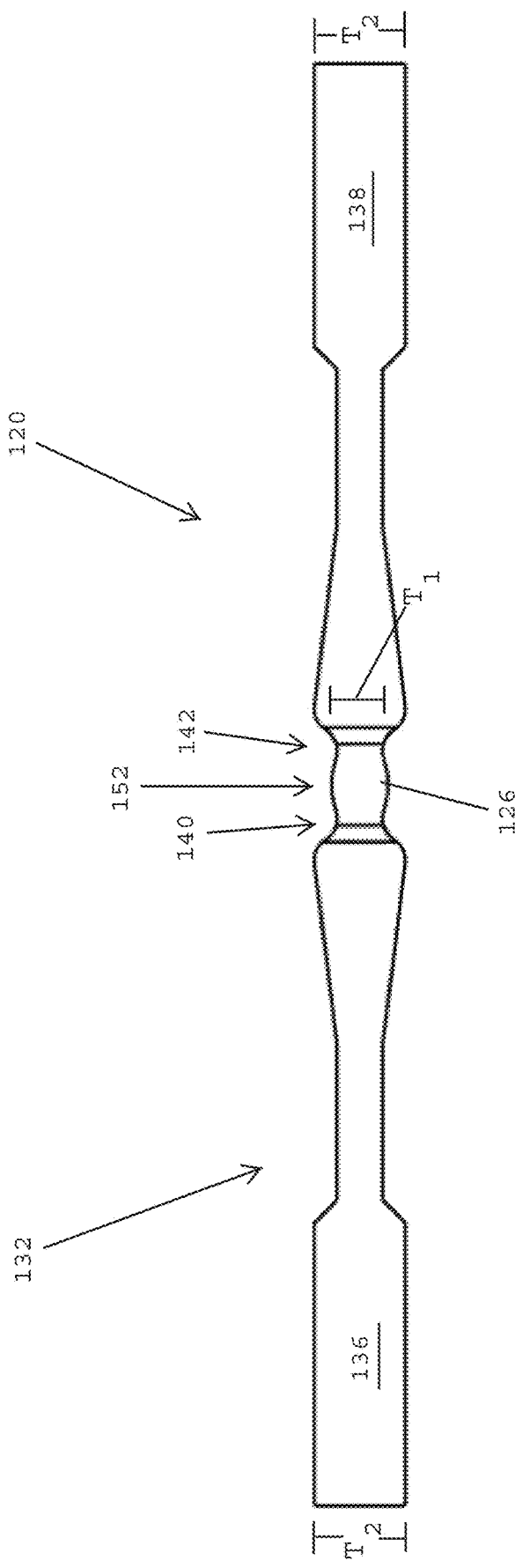
FIG. 5F is a cross-sectional view of the barbed monofilament insert shown in FIG. 5D.

Referring to FIG. 5F in one embodiment, the end effector 132 of the barbed monofilament insert 120 preferably includes the first lateral wing 136 that extends outwardly from the first lateral side 140 of the elongated core 126 and the second lateral wing 138 that extends outwardly from the second lateral side 142 of the elongated core 126. The end effector 132 preferably includes the first transition zone 145A that is located between the first lateral side 140 of the elongated core 126 and the inner end of the first lateral wing 136, and the second transition zone 145B that is located between the second lateral side 142 of the elongated core 126 and the inner end of the second lateral wing 138. The center region 152 of the elongated core 126 has the thickness $T_1$ that is less than the thicknesses $T_2$ of the respective first and second lateral wings 136, 138 of the end effector 132. In one embodiment, the thickness $T_1$ of the elongated core 126 that extends through the end effector 132 (shown in FIG. 5F) is equal to the thickness $T_3$ of the elongated core 126 that extends through the barbed section 130 of the barbed monofilament insert 120 (shown in FIG. 5D-1).

Figure 6A:
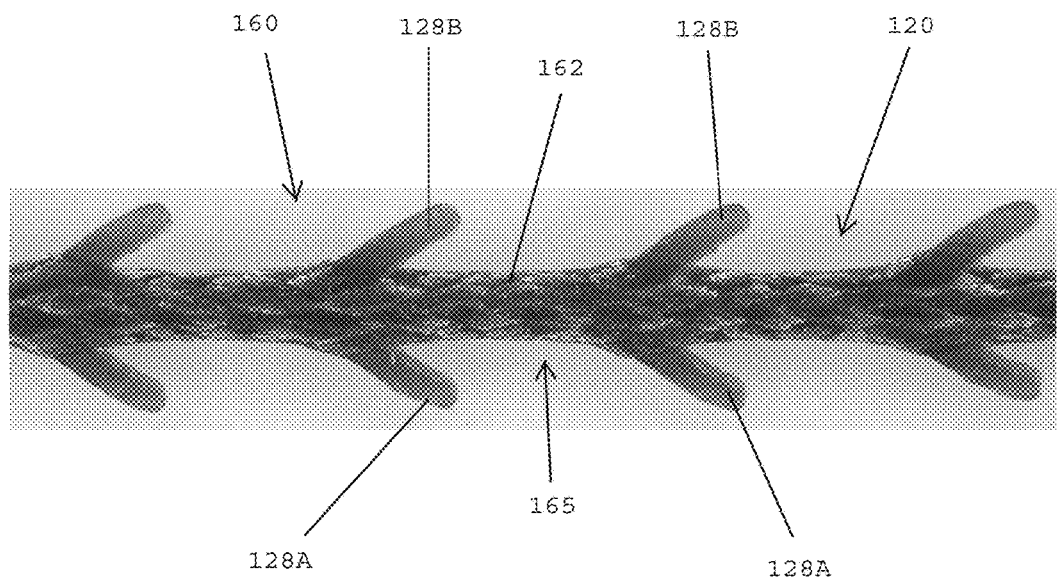
FIG. 6A is a top view of a braided barbed suture including the barbed monofilament insert of FIGS. 5A-5F and a braided sheath wound around the elongated core of the barbed monofilament insert, in accordance with one embodiment of the present patent application.

Referring to FIGS. 6A and 68B, in one embodiment, a braided barbed suture 160 may be formed by winding filaments around the elongated core 126 (FIG. 5E) of the barbed monofilament insert 120 to form a braided sheath 162 that surrounds the elongated core 126 of the barbed monofilament insert 120. A combination of the barbed monofilament insert 120 and the braided sheath 150 preferably form the composite core 165 of the braided barbed suture 160. The first and second barbs 128A, 128B of the barbed monofilament insert 120 preferably extend outwardly beyond the outer perimeter of the braided sheath 162 for engaging tissue.

In one embodiment, the braided barbed suture desirably includes a barbed monofilament insert having an elongated core that has the reduced thickness, diameter, and/or smaller cross-sectional area than what is found in prior art elongated cores, whereby the amount of material that is wound around the elongated core to form the braided sheath will be less bulky to provide a braided barbed suture having lower bending stiffness (i.e., more flexibility). The characteristics of the materials used to make the braided barbed suture (e.g., the size of the core, the degree of over-braiding, the core and braid materials) will directly impact the handling and strength characteristics of the braided barbed suture.

The reduced thickness of the elongated core enables a greater proportion of the composite core 165 (i.e., the combination of the braided sheath and the elongated core) to be comprised of the braided sheath 162, allowing for a braided barbed suture construction that has the benefits of a braided suture (e.g., handling, flexibility, compatibility with surgical instrumentation).

In one embodiment, when the composite core 165 of the braided barbed suture 160 is viewed in cross-section, the ratio of the thickness or diameter of the elongated core 126 relative to the thickness or diameter of the composite core 165 including the braided sheath 162 (i.e., the core to braid ratio) is less than one. Thus, the braided sheath 162 comprises a larger area of the composite core 165 than does the elongated core 126, which enhances the tensile strength of the braided barbed suture 160 via the braided sheath component and improves the overall flexibility of the braided barbed suture 160 due to the thinner than normal elongated core component.

In one embodiment, the barbs 128A, 1289 of the braided barbed suture 160 extend in a first plane P1 and the thickness and/or diameter measurements of the elongated core 126 and the composite core 165 are taken along an axis that lies in a second plane P2, which is perpendicular to the first plane P1.

In one embodiment, the thickness measures may be obtained using a Mitutoyo gauge ID-39 test instrument including a circular foot having a ½ inch diameter. In one embodiment, the gauge may include a presser foot that is configured to be gently lowered until it rests upon the suture at which point the thickness measurement is recorded. The suture is then removed and the height measurement is recorded. In one embodiment, after the presser foot is lowered onto the suture, a time period of approximately 0.5 seconds is allowed to elapse before the thickness measurement is recorded. In one embodiment, thickness measurements are made at the leader ends of the barbed monofilament insert and the braided barbed suture. Three thickness measurements are preferably taken in separate locations along the length of the suture strand. For barbed and braided-barbed sutures, one measurement is taken on the leader end of the suture material, and two measurements are taken on the barbed section.

In one embodiment, when the braided sheath 162 envelopes the elongated core 126 to form the composite core 165 of a braided barbed suture 160, the ratio of the thickness $T_{EC}$ of the elongated core 126 relative to the aggregate thickness $T_{CC}$ of the composite core 165 is between about 0.16 to 0.91, and more preferably between about 0.24 to 0.73.

In one embodiment, due to the use of a thinner elongated core 126 relative to the thicknesses of the barbs 128A, 128B, the braided barbed suture 160 provides an extremely low bending stiffness that is almost equivalent to a multifilament device, while at the same time delivering an equal or greater tensile strength compared with a monofilament barbed device having a similar thickness or outer diameter. Moreover, the smaller elongated core 126 results in the composite core 165 having a smaller thickness or outer dimension (e.g., outer diameter) than is possible with prior art barbed suture inserts having thicker elongated cores.

Figure 7A:
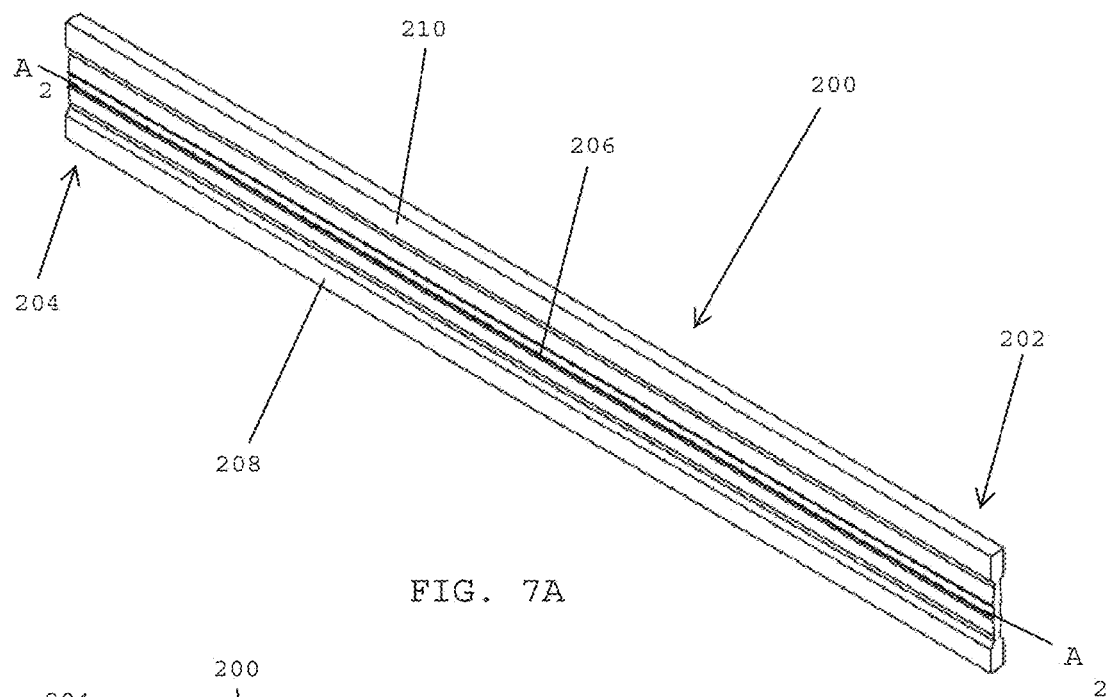
FIG. 7A is a perspective view of a barbed suture blank that is used for making a barbed monofilament insert, in accordance with one embodiment of the present patent application.
Figure 7B:
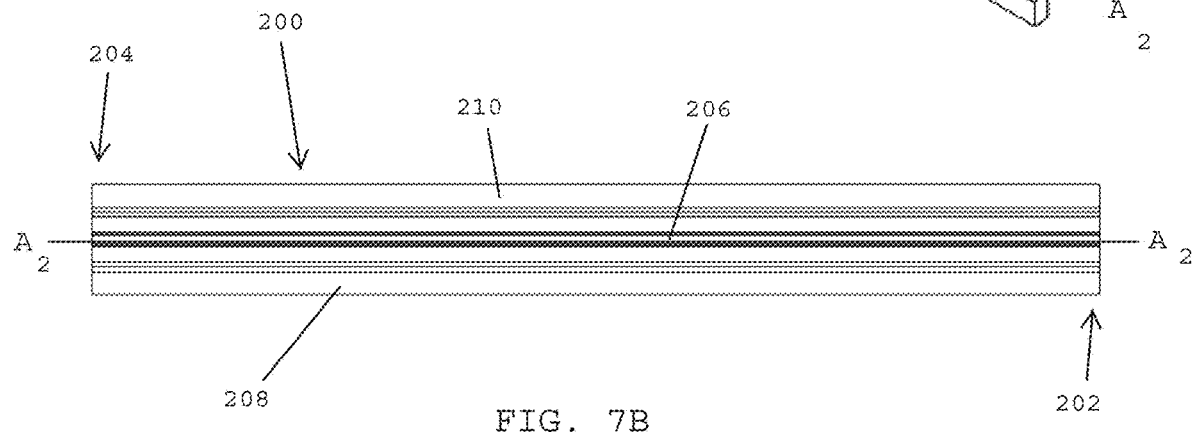
FIG. 7B is a top plan view of the barbed suture blank shown in FIG. 7A.
Figure 7C:
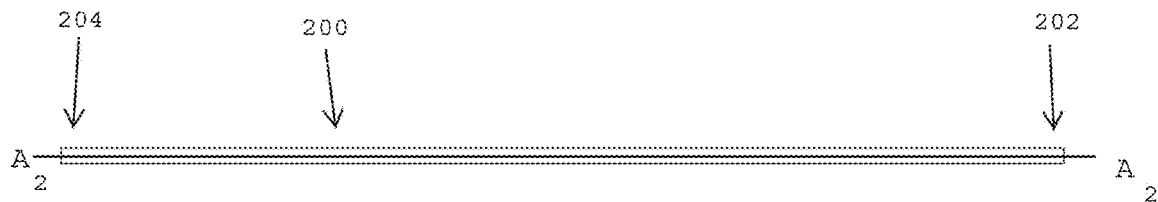
FIG. 7C is a side view of the barbed suture blank shown in FIGS. 7A and 7B.

Referring to FIGS. 7A-7C, in one embodiment, a barbed suture blank 200, such as a ribbon of a polymeric material, is used to form a barbed monofilament insert having an elongated core and a plurality of barbs that project outwardly from opposite lateral sides of the elongated core. In one embodiment, the barbed suture blank 200 preferably includes a proximal end 202, a distal end 204, and a longitudinal axis $A_2$ that extends along the length of the barbed suture blank between the proximal and distal ends 202, 204 thereof. In one embodiment, the barbed suture blank preferably includes an elongated core 206 that extends along the longitudinal axis $A_2$, a first lateral section 208 that extends along a first lateral side of the elongated core 206, and a second lateral section 210 that extends along a second lateral side of the elongated core 206.

Figure 7D:
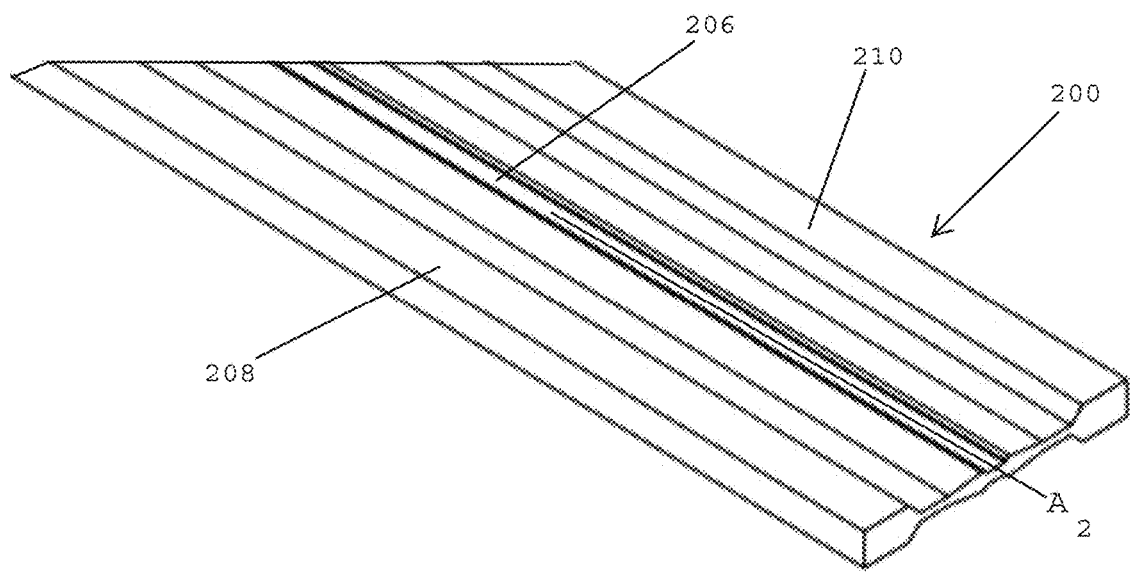
FIG. 7D is a perspective view of a proximal end of the barbed suture blank shown in FIGS. 7A-7C.
Figure 7E:
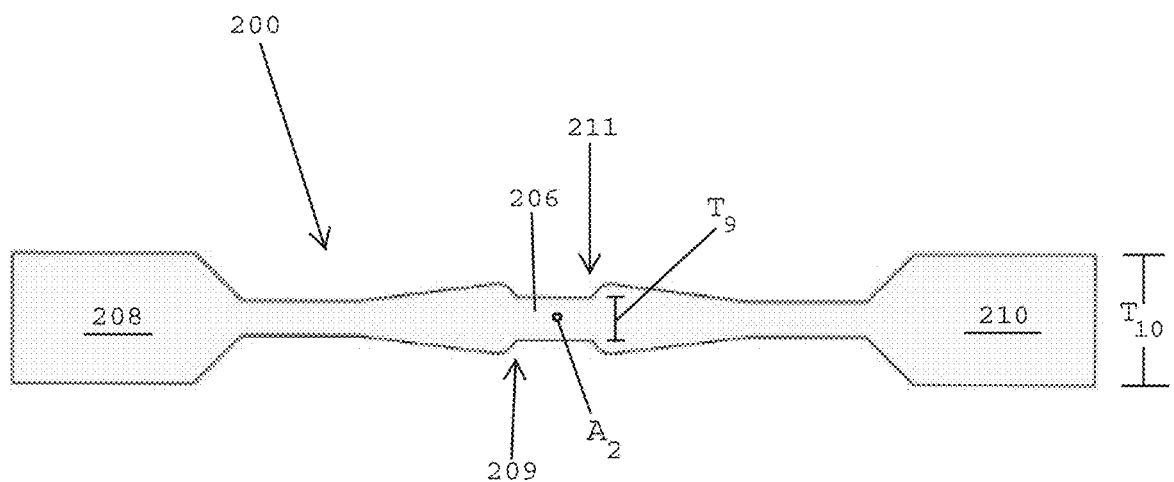
FIG. 7E is a cross-sectional view of the barbed suture blank shown in FIG. 7B.

Referring to FIGS. 7D and 7E, in one embodiment, the barbed suture blank 200 preferably has a pre-formed cross-sectional shape, which includes the elongated core 206 and the first and second lateral sections 208, 210 that are located on opposite sides of the elongated core 206. In one embodiment, the elongated core 206 is preferably located in the center of the barbed suture blank 200 and extends along the longitudinal axis $A_2$ of the barbed suture blank 200. In one embodiment, the elongated core 206 has a thickness $T_9$ that is less than the thicknesses $T_{10}$ of the respective first and second lateral sections 208, 210 of the barbed suture blank 200. The barbed suture blank 200 has a first transition zone 209 that is located between a first lateral side of the elongated core 206 and an inner end of the first lateral section 208, and a second transition zone 211 that is located between a second lateral side of the elongated core 206 and an inner end of the second lateral section 210. In one embodiment, the first and second transition zones 209, 211 widen between the relatively thinner elongated core 206 and the relatively thicker inner ends of the first and second lateral sections 208, 210.

In one embodiment, the barbed suture blank 200 may be placed into a die or punch for forming a barbed monofilament insert including an elongated core, a plurality of barbs projecting outwardly from the elongated core, and an end effector connected with an end of the elongated core.

Referring to FIGS. 8A and 8B, in one embodiment, the barbed suture blank 200 (FIGS. 7A-7E) is desirably punched or cut to form a barbed monofilament insert 220 having a proximal end 222 and a distal end 224. In one embodiment, the barbed monofilament insert 220 desirably includes an elongated core 226 that extends along the length of the barbed suture. The barbed monofilament insert 220 desirably includes a plurality of barbs 228 that extend outwardly from opposite sides of the elongated core 226 to define a barbed midsection 230 of the barbed monofilament insert 220. The barbed monofilament insert 220 desirably includes an end effector 232 (e.g., a stop) that is secured to a proximal end of the elongated core 226, which is located at the proximal end 222 of the barbed monofilament insert 220.

In one embodiment, the barbed monofilament insert 220 preferably includes a connector section 234 of the elongated core 226 that enables the barbed midsection 230 (FIG. 9A) of the barbed monofilament insert 220 to pass through a first track of a guide cartridge, the end effector 232 to pass through a second track of a guide cartridge, and the connector section 234 to pass through a slot that interconnects the first and second tracks of the guide cartridge as disclosed in commonly assigned, U.S. patent application Ser. No. 17/336,680 filed on even date herewith, which claims benefit of U.S. Provisional Application Ser. No. 63/039,649, filed on Jun. 16, 2020, the disclosure of which is hereby incorporated by reference herein.

In one embodiment, the elongated core 226 of the barbed monofilament insert 220 preferably has a cross-sectional shape that is similar to the elongated core 206 of the barbed suture blank 200 shown and described above in FIG. 7E. The elongated core 226 preferably defines a section of the barbed suture that has a thickness that is less than or equal to the thicknesses of the respective barbs 228 that project outwardly from opposite sides of the elongated core 226 and the thickness of the first and second wings of the end effector 232.

Figure 8C:
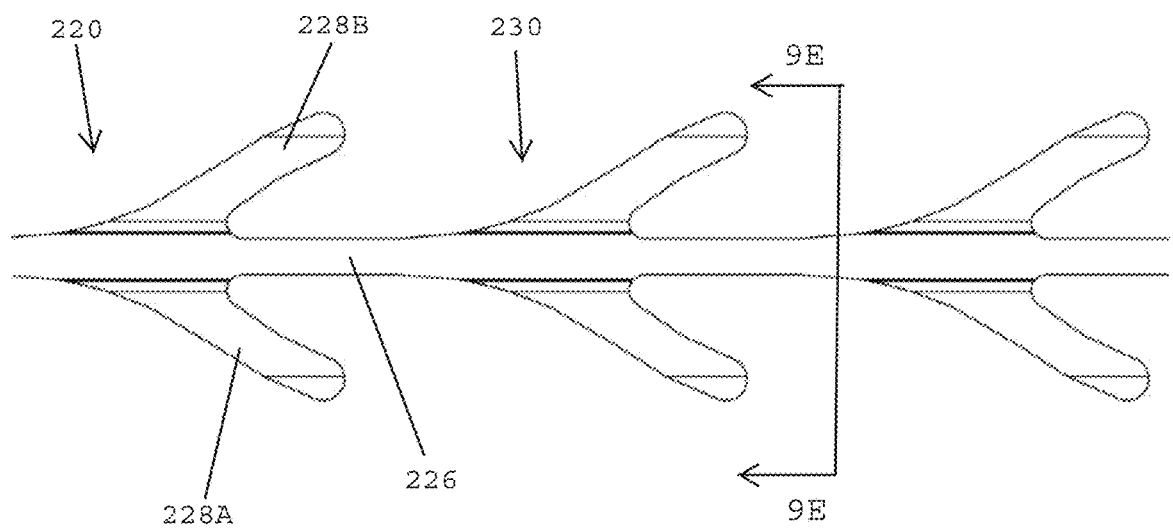
FIG. 8C is a magnified view of a midsection of the barbed monofilament insert shown in FIGS. 8A and 8B.
Figures 1, 8C:
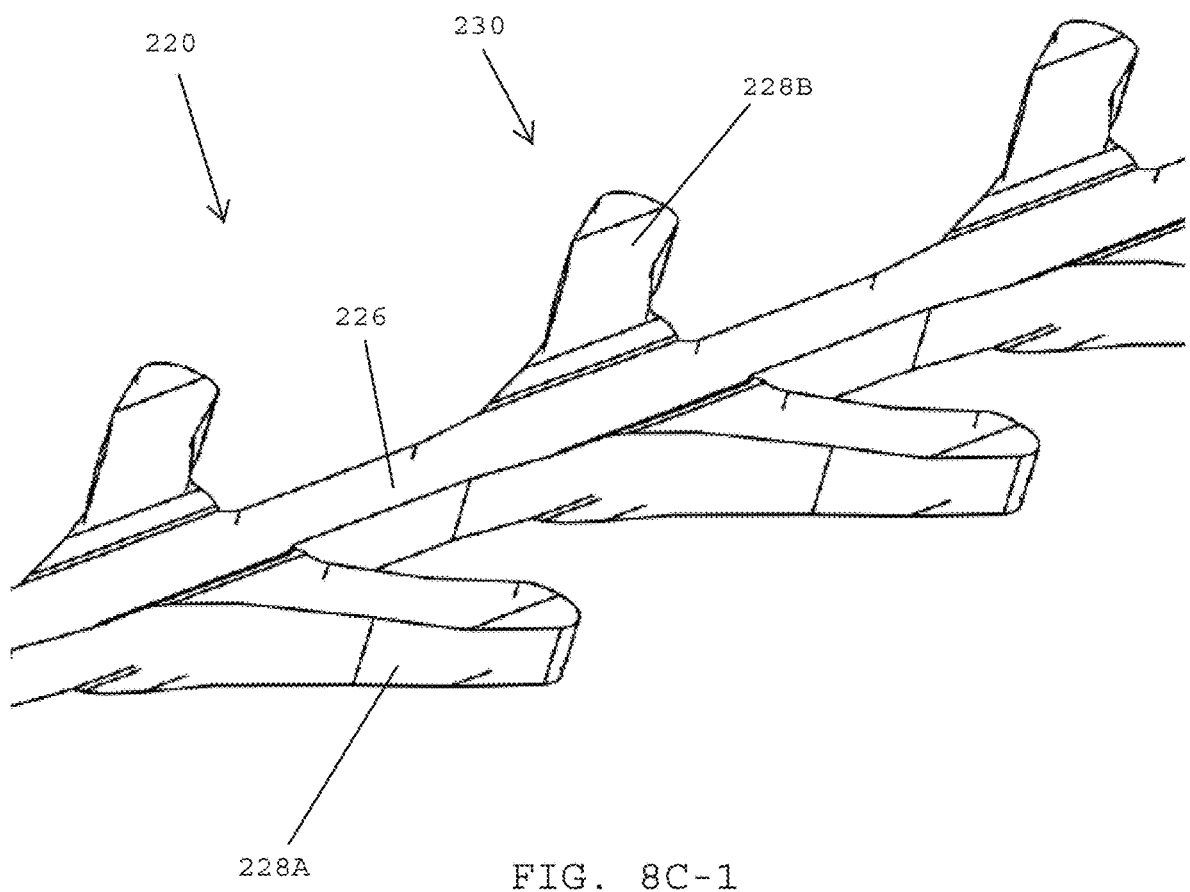

Referring to FIGS. 8O and 8C-1, in one embodiment, the barbed midsection 230 of the barbed monofilament insert 220 preferably includes the elongated core 226 that extends along the length of the barbed monofilament insert 220 from the proximal end 222 to the distal end 224 (FIG. 8A) thereof. The barbed monofilament insert 220 desirably includes first barbs 228A that project outwardly from a first lateral side of the elongated core 226 and second barbs 228B that project outwardly from a second lateral side of the elongated core 226 that is opposite the first lateral side. As will be described in more detail herein, the elongated core 226 of the barbed monofilament insert 220 has a thickness that is less than or equal to the thicknesses of the respective first and second barbs 228A, 228B that project outwardly from opposite lateral sides of the elongated core 226. As previously noted herein, providing a barbed monofilament insert having an elongated core with a reduced thickness will preferably reduce the overall cross-sectional dimension of the composite core (i.e., the combination of the elongated core and the braided sheath) for maintaining the flexibility of the braided barbed suture after the braided sheath has been formed around the elongated core 226.

Figure 8D:
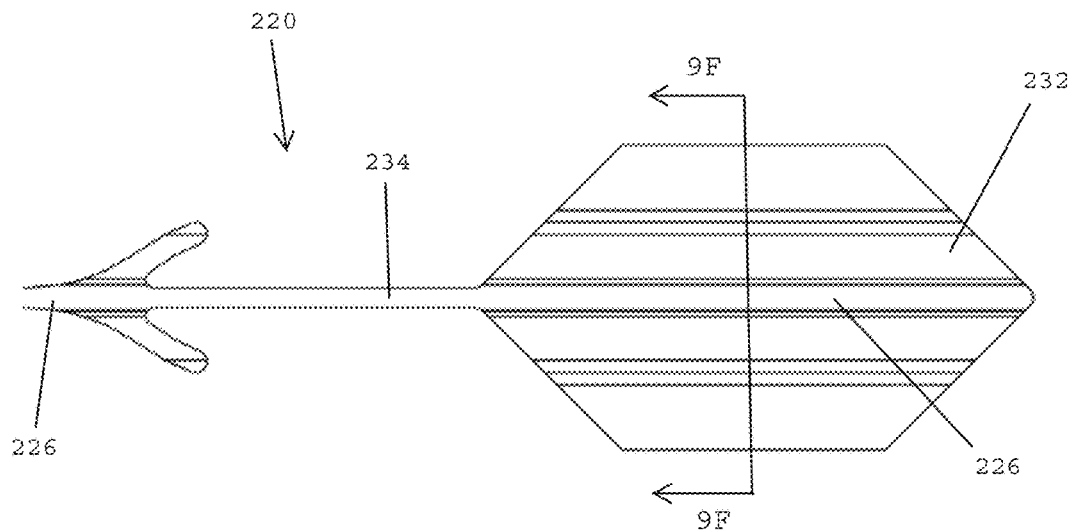
FIG. 8D is a top view of a proximal end of the barbed monofilament insert shown in FIGS. 8A and 8B.
Figures 1, 8D:
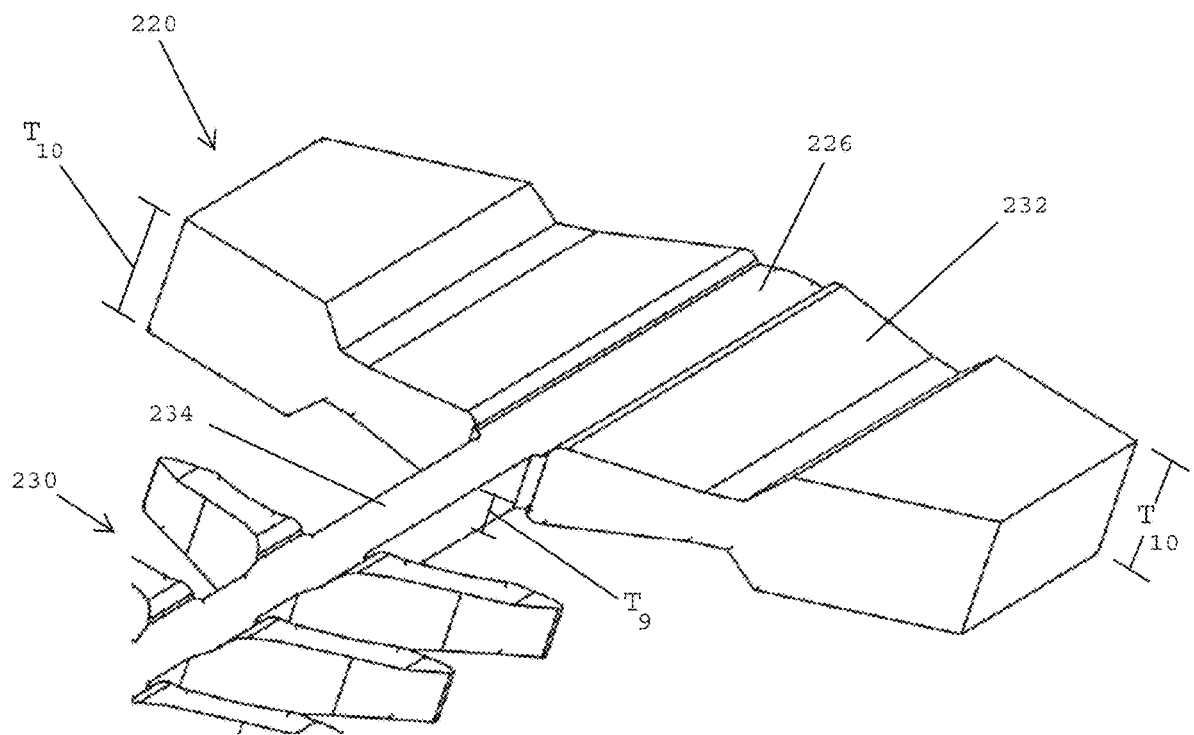

Referring to FIGS. 8D and 8D-1, in one embodiment, the barbed monofilament insert 220 preferably includes the end effector 232 (e.g., a stop) that is secured to a proximal end of the elongated core 226 at the proximal end 222 of the barbed monofilament insert 220. In one embodiment, the barbed monofilament insert 220 preferably includes the connector section 234 of the elongated core 226 that enables the barbed midsection 230 (FIG. 8A) of the barbed monofilament insert 220 to pass through a first track of a guide cartridge, the end effector 232 to pass through a second track of the guide cartridge, and the connector section 234 to pass through a slot that interconnects the first and second tracks, as disclosed in commonly assigned, U.S. patent application Ser. No. 17/336,680, filed on even date herewith, which claims benefit of U.S. Provisional Application Ser. No. 63/039,649, filed on Jun. 16, 2020, the disclosure of which is hereby incorporated by reference herein.

In one embodiment, the elongated core 226 preferably extends through the barbed section 230 of the barbed monofilament insert 220 as well as through the end effector 232 that is located at the proximal end 222 of the barbed monofilament insert 220. As shown in FIG. 9D-1, the elongated core 226 has a thickness $T_9$ that is less than the thicknesses $T_{10}$ of the respective first and second lateral wings 236, 238 of the end effector 232.

Figure 8E:
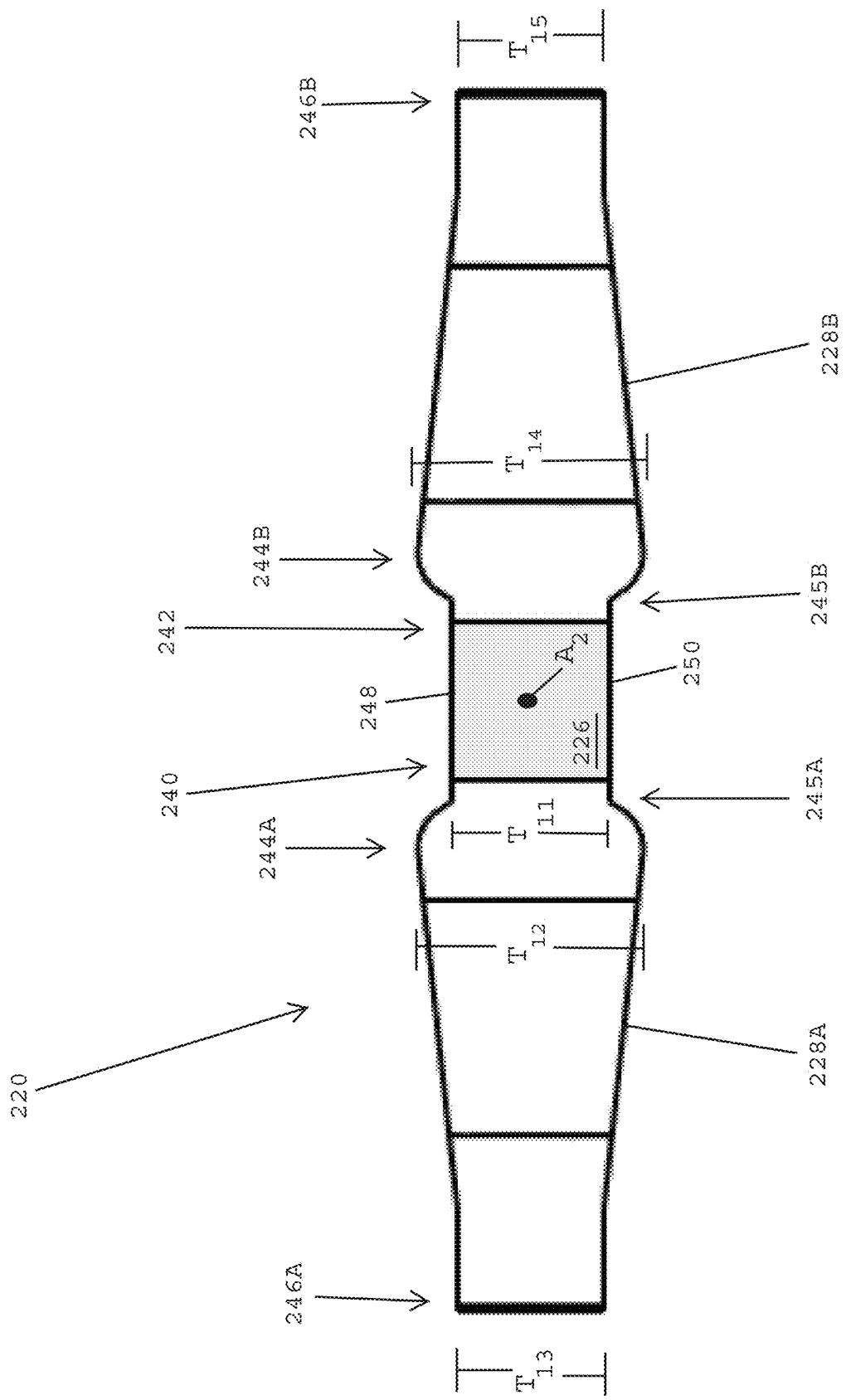
FIG. 8E is a cross-sectional view of the barbed monofilament insert shown in FIG. 8C.

Referring to FIG. 8E, in one embodiment, the barbed monofilament insert 220 preferably includes first barbs 228A that project outwardly from a first lateral side 240 of the elongated core 226 and second barbs 228B that project outwardly from a second lateral side 242 of the elongated core 226. In one embodiment, the elongated core 226 is preferably located at the center of the barbed monofilament insert 220 and extends along the longitudinal axis $A_2$ of the barbed suture. In one embodiment, the elongated core 226 preferably forms a flexible spine or backbone that provides flexibility to the barbed monofilament insert 220 during a suturing operation.

In one embodiment, the first barb 228A preferably has an inner end 244A that is connected with the first lateral side 240 of the elongated core 226 and an outer end 246A that defines a free end of the first barb. The barbed monofilament insert 220 desirably includes a first transition zone 245A that is located between the first lateral side 240 of the elongated core 226 and the inner end 244A of the first barb 228A. The first transition zone 245A widens out or becomes thicker between the first lateral side 240 of the elongated core 226 and the inner end 244A of the first barb 228A.

The second barb 228B preferably has an inner end 244B that is connected with the second lateral side 242 of the elongated core 226 and an outer end 246B that defines a free end of the second barb. The barbed monofilament insert 220 desirably includes a second transition zone 245B that is located between the second lateral side 242 of the elongated core 226 and the inner end 244B of the second barb 228B. The second transition zone 245B widens out or becomes thicker between the second lateral side 240 of the elongated core 226 and the inner end 2449 of the second barb 228B.

In one embodiment, the elongated core 226 preferably has a substantially flat top surface 248 located on a top side of the barbed monofilament insert 220 and substantially flat bottom surface 250 located on a bottom side of the barbed suture. In one embodiment, the substantially flat top and bottom surfaces 248, 250 define a thickness $T_{11}$ of the elongated core 226.

In one embodiment, the first barb 228A is preferably thicker at the inner end 244A thereof and thinner at the outer free end 246A thereof. In one embodiment, the inner end 244A of the first barb 228A has a thickness $T_{12}$ and the outer end 246A of the first barb 228A has a thickness $T_{12}$ that is less than the thickness $T_{12}$ of the inner end 244A. In one embodiment, the thickness $T_{11}$ of the elongated core 226 is less than the thickness $T_{12}$ at the inner end 244A of the first barb 228A. In one embodiment, the thickness $T_{11}$ of the elongated core 226 is less than or equal to the thickness $T_{12}$ at the outer end 246A of the first barb 228A.

In one embodiment, the second barb 2238B is preferably thicker at the inner end 2448 thereof and thinner at the outer free end 246B thereof. In one embodiment, the inner end 244B of the second barb 228B has a thickness $T_{14}$ and the outer end 146B of the second barb 128B has a thickness $T_{15}$ that is less than the thickness $T_{14}$ of the inner end 144B. In one embodiment, the thickness $T_{11}$ of the elongated core 226 is less than the thickness $T_{11}$ at the inner end 246A of the second barb 228B. In one embodiment, the thickness $T_1$ of the elongated core 126 is less than or equal to the thickness $T_{15}$ of the outer end 246B of the second barb 228B.

Figure 3:
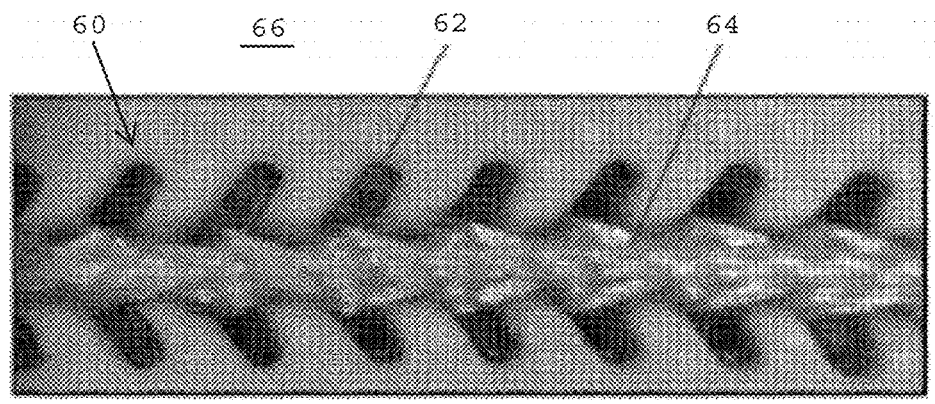
FIG. 3 is a top plan view of a prior art braided barbed suture including a barbed suture insert having an elongated core and barbs, and a braided sheath that is formed over the elongated core of the barbed suture.
Figure 8F:
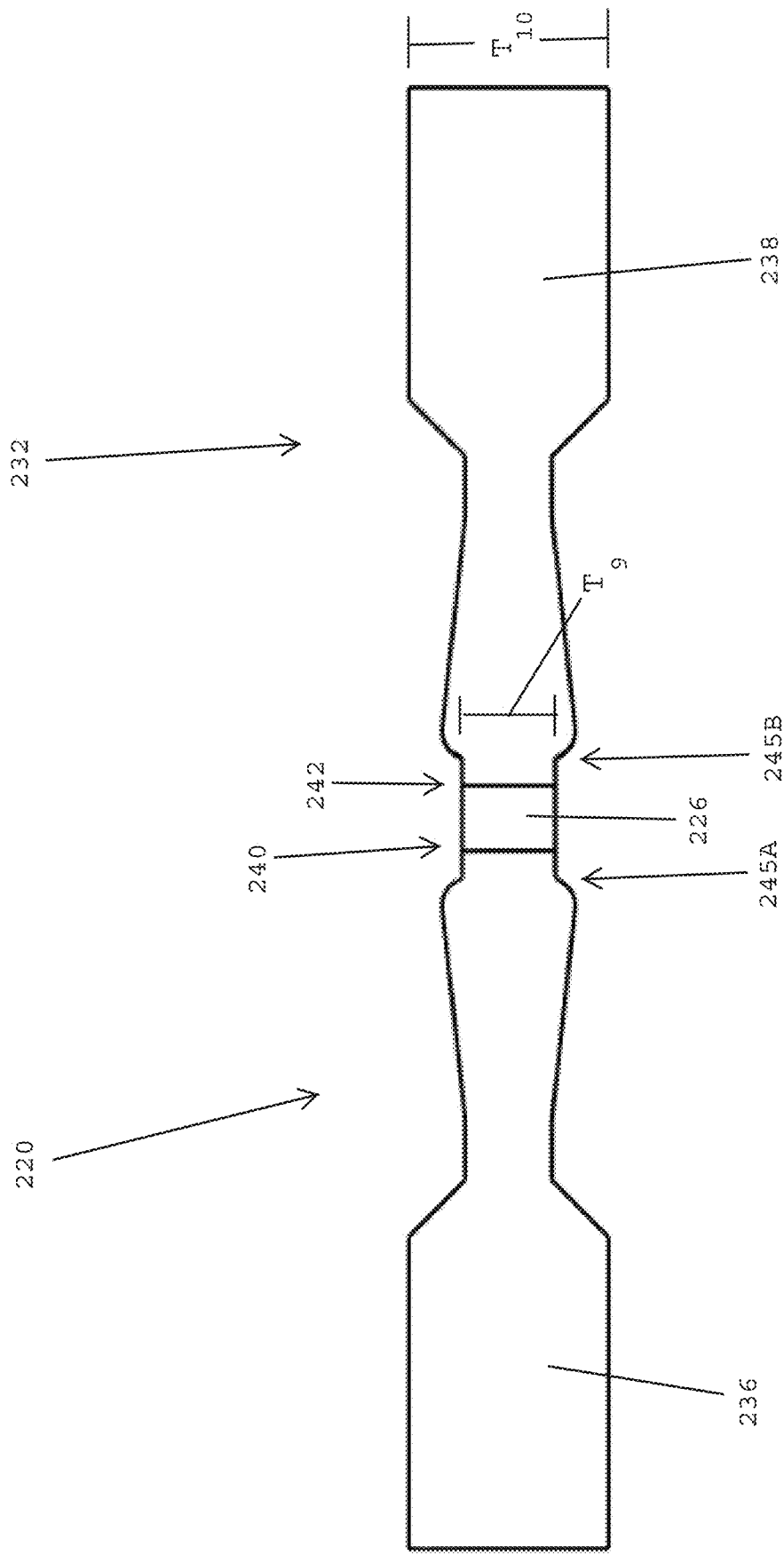
FIG. 8F is a cross-sectional view of the barbed monofilament insert shown in FIG. 8D.

Referring to FIG. 8F in one embodiment, the end effector 232 of the barbed monofilament insert 220 preferably includes the first lateral wing 236 that extends outwardly from the first lateral side 240 of the elongated core 226 and the second lateral wing 238 that extends outwardly from the second lateral side 242 of the elongated core 226. The end effector 232 preferably includes the first transition zone 245A that is located between the first lateral side 240 of the elongated core 226 and the inner end of the first lateral wing 236, and the second transition zone 245B that is located between the second lateral side 242 of the elongated core 226 and the inner end of the second lateral wing 238. The elongated core 226 has a thickness $T_{11}$ that is less than the thicknesses $T_{10}$ of the respective first and second lateral wings 236, 238 of the end effector 232. In one embodiment, the thickness $T_{11}$ of the elongated core 226 that extends through the end effector 232 is equal to the thickness $T_9$ of the elongated core 226 that extends through the barbed section 230 of the barbed monofilament insert 220 (FIG. 3D-1).

In one embodiment, a braided barbed suture may be formed by winding filaments around the elongated core 226 of the barbed monofilament insert 220 to form a braided sheath that surrounds and/or envelopes the elongated core 226 of the barbed monofilament insert 220.

Figures 9, 10:
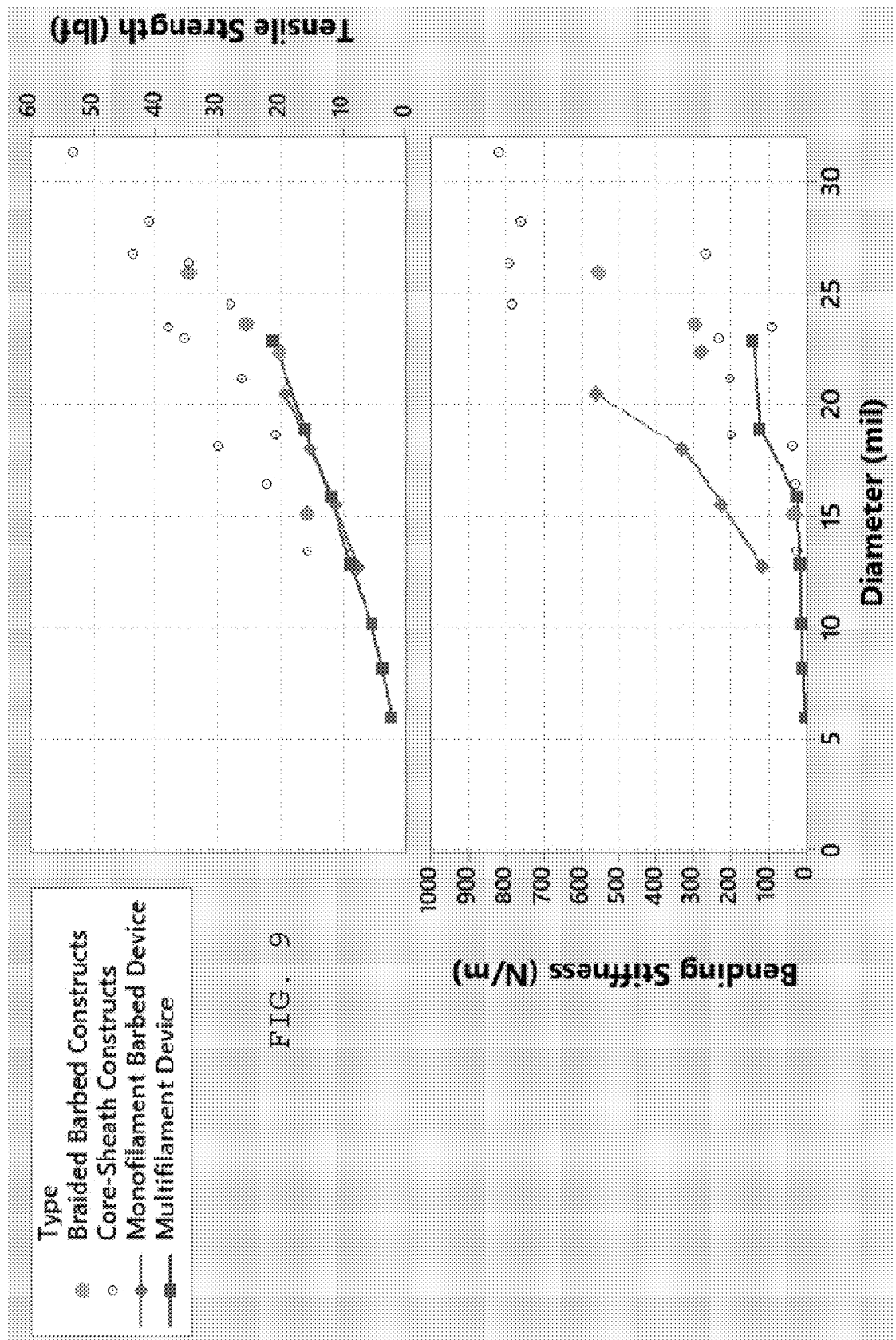
FIG. 9 is a graph that plots the tensile strength characteristics for braided barbed sutures having different constructions.
FIG. 10 is a graph that plots bending stiffness characteristics for braided barbed sutures having different constructions.

Referring to FIG. 9, when constructing braided barbed sutures, the tensile strengths of the braided barbed sutures may be controlled by selecting the types and the dimensions of the materials that are used to make the braided barbed sutures. The graph in FIG. 9 shows that the tensile strength of a braided barbed suture is dependent upon the combination of materials used to make the braided barbed suture.

Example 1. In one embodiment, an elongated core of a barbed monofilament insert has a thickness of 6.39 mil. Filaments are wound around the elongated core to form a braided sheath. The combination of the elongated core and the braided sheath that envelopes the elongated core forms a composite core having a thickness of 23.44 mil. The ratio of the thickness of the elongated core relative to the thickness of the composite core is 0.27 (6.39/23.44=0.27).

Example 2. In one embodiment, an elongated core of a barbed monofilament insert has a thickness of 20.18 mil. Filaments are wound around the elongated core to form a braided sheath. The combination of the elongated core and the braided sheath that envelopes the elongated core forms a composite core having a thickness of 24.47 mil. The ratio of the thickness of the elongated core relative to the thickness of the composite core is 0.82 (20.18/24.47=0.82).

Example 3. In one embodiment, an elongated core of a barbed monofilament insert has a thickness of 6.34 mil. Filaments are wound around the elongated core to form a braided sheath. The combination of the elongated core and the braided sheath that envelopes the elongated core forms a composite core having a thickness of 13.4 mil. The ratio of the thickness of the elongated core relative to the thickness of the composite core is 0.47 (6.34/14.4=0.47).

Referring to FIG. 10, the bending stiffness of braided barbed sutures may be controlled by selecting the types and dimensions of the materials that are used to make braided barbed sutures. The graph in FIG. 10 shows that the bending stiffness of a braided barbed suture is dependent upon the combination of materials used to make the braided barbed suture.

As shown in FIG. 10, in one embodiment, in order to maintain the flexibility of a braided barbed suture, the barbed monofilament insert preferably has a thickness of about 5 to 20 mil, and more preferably about 6 to 8 mil, and the composite core (i.e., a combination of the elongated core and the braided sheath) preferably has a thickness of about 13 to 30 mil, and more preferably about 13 to 18 mil. Within the above-listed ranges (i.e., a barbed monofilament insert thickness of 6-8 mil and a composite core thickness of 13-18 mil), the bending stiffness of the braided barbed suture will match the bending stiffness that can be attained by a multifilament suture device.

In one embodiment, a braided barbed suture having an elongated core thickness of 5-10 mil and a composite core thickness of 11-30 mil is preferred. In one embodiment, a highly preferred braided barbed suture has an elongated core thickness of 6-8 mil and a composite core thickness of 11-25 mil for an elongated core/composite core ratio of about 0.47.

Testing models were formulated and tests were conducted to evaluate and analyze the failure mechanics of braided barbed sutures. In particular, tests were conducted to determine 1) the contributions of the barbed monofilament insert and the braided sheath to the overall tensile strength of the braided barbed suture, and 2) the impact of the mechanical interaction of the barbs of the barbed monofilament insert and the braided sheath on the overall tensile strength of the braided barbed suture.

In order to complete the analysis of the failure mechanics of braided barbed sutures, data was compiled in two discrete stages. A first testing stage included an analysis of the failure mechanics of braided suture specimens (Group I), whereby each Group I specimen included a barb-free monofilament core and a braided sheath overlying the barb-free monofilament core. A second testing stage included an analysis of the failure mechanics of braided barbed suture specimens (Group II), whereby each Group II specimen included a barbed monofilament insert and a braided sheath overlying the elongated core of the barbed monofilament insert.

The Group I specimens were fabricated using barb-free monofilament cores having various sizes (e.g., USP 5-0, 2-0, and 1) with diameters ranging from 5 to 20 mil, and braided sheaths having various densities (e.g., 56 or 80 Denier yarn, 1- or 2-ply, and 16 carriers), resulting is a final composite core with diameters ranging from 13 to 31 mil. The fact that the Group I specimens had no barbs provided a unique opportunity to assess the mechanical coupling of the barb-free monofilament cores and the braided sheaths that envelope the monofilament cores. Moreover, the construction of the Group I specimens enabled the barb-free monofilament core to be removed from the braided sheath, which allowed each component of the braided suture to be mechanically tested independently of one another.

Figure 11:
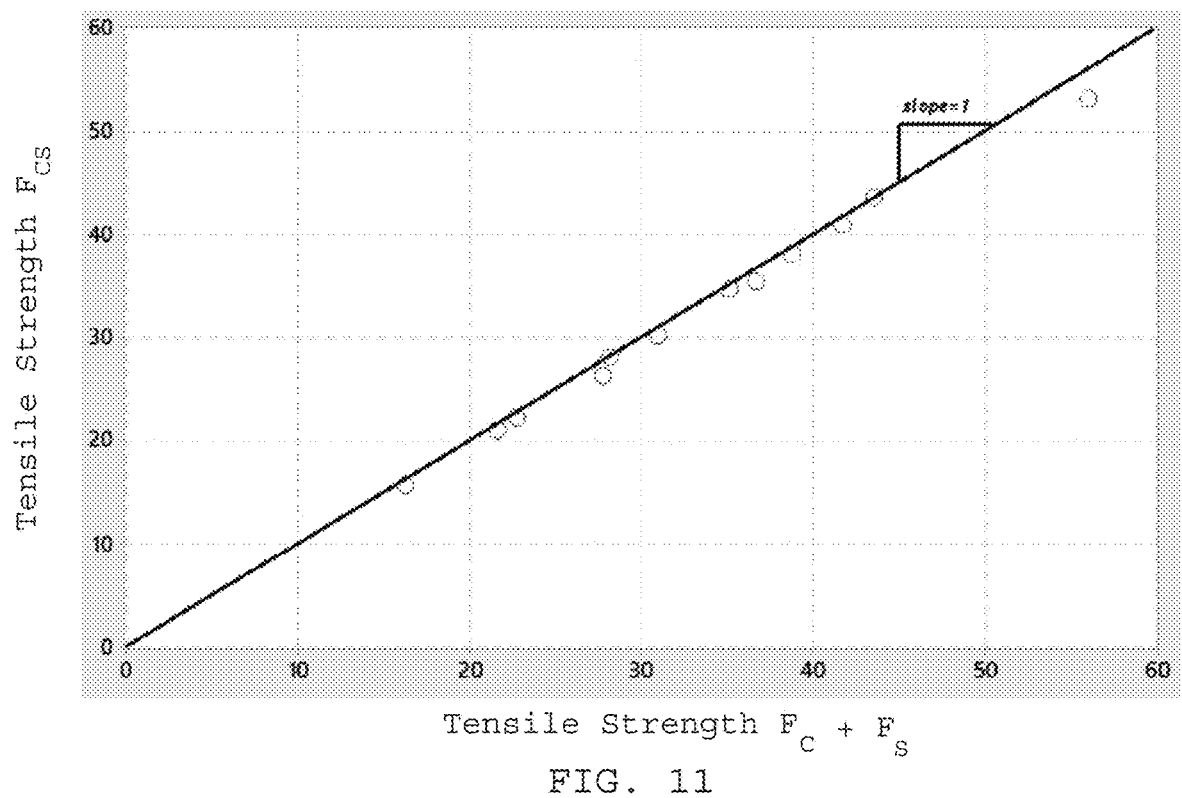
FIG. 11 is a graph of a model equation that predicts the tensile strengths of braided barbed sutures and braided sutures having no barbs.

An equation Fcs=Fc+Fs (Equation 1) was utilized to complete the mechanical failure testing, where $F_{CS}$ is the combined tensile strength of the monofilament core and the braided sheath composite, $F_C$ is the tensile strength of the monofilament core, and $F_S$ is the tensile strength of the braided sheath. FIG. 11 shows a plot for $F_{CS}$ vs. $F_C+F_S$. All of the plotted points are projected to fall on a line of slope equal to one which passes through the origin.

Figure 12:
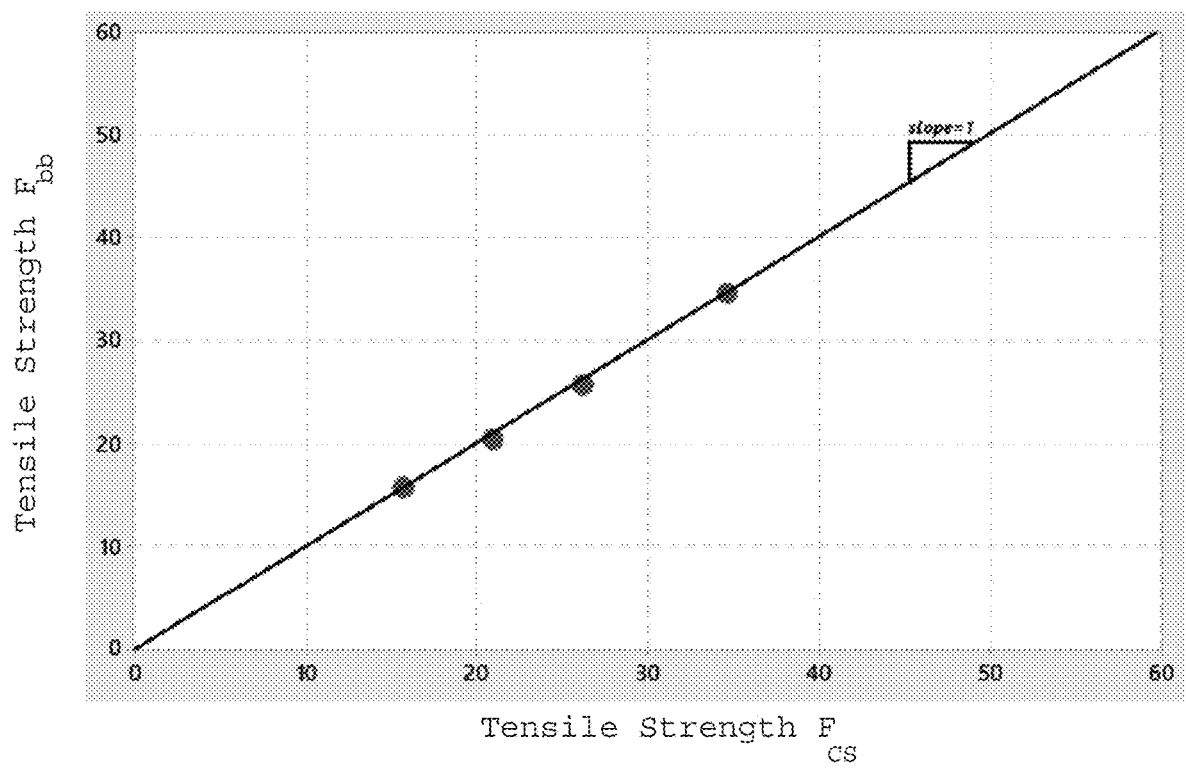
FIG. 12 is a graph of test results indicating that there are no differences in tensile strengths between braided barbed sutures and braided sutures having no barbs that have a similar construction.

Evaluation of the Failure Mechanics of Braided Sutures Having No Barbs (Group I Specimens) versus Braided Barbed Sutures Having Barbs (Group II Specimens). In order to evaluate and compare the failure mechanics of the Group I Specimens versus the Group II Specimens, the Group I and II specimens were made to have approximately matching construction. The respective tensile strengths of the Group I Specimens (i.e., $F_{cs}$) versus the Group II Specimens (i.e., $F_{bb}$) were then experimentally determined. Referring to FIG. 12, a plot of $F_{cs}$ and $F_{bb}$ was built in which a reference line with slope=1 and which passes through the origin (hereinafter referred to as the "reference line") is depicted.

Referring to FIG. 12, after testing the Group I specimens, a plot of the data shows that the results predicted by Equation 1 hold true for all of the specimens that were tested, and confirms that the tensile strength of the Group I specimens is simply the linear addition of the respective tensile strengths of the barb-free monofilament core and the braided sheath that envelopes the core. An analysis of the testing results did not reveal any other significant mechanical interactions such as friction forces between the monofilament cores and the braided sheath components. With Equation 1 being validated, further mechanical failure testing of braided barbed sutures was conducted.

When evaluating the Failure Mechanics of Braided Sutures Having No Barbs (Group I Specimens) versus Braided Barbed Sutures Having Barbs (Group II Specimens), in theory, there are three possible scenarios that may develop: Scenario #1) data tends to lie above the reference line, indicating that the interaction of the barbs and braid actually increases the device tensile strength relative to that predicted by Equation 1: Scenario #2) data tends to lie on the reference line, indicating that the barbs do not have any effect on the tensile strength relative to that predicted by Equation 1; and Scenario #3) data tends to lie below the reference line, indicating that the barbs reduce the device tensile strength, as predicted by Equation 1.

FIG. 12 is a plot of the test results and shows a reference line that is associated with Scenario #2. The test results indicate that the presence of barbs provides no marked effect on the tensile strength of the suture. Thus, the aggregate tensile strength of the braided barbed suture is equal to the combination of the tensile strength of the barbed monofilament insert added with the tensile strength of the braided sheath, which is consistent with Equation 1.

The test results support the following conclusions. First, for a barbed monofilament insert having an elongated core having a predetermined diameter, providing a braided barbed suture having a relatively larger sheath size and a relatively smaller elongated core size (i.e., the sheath to core ratio) is ideal, because the design capitalizes on the inherent strength of the braided sheath portion of the braided barbed suture.

Second, utilization of a large braided sheath to elongated core ratio for a given diameter will provide greater flexibility (i.e., lower bending stiffness), which improves the handling characteristics of the braided barbed suture.

Third, since the braided sheath is exposed and visible to surgical personnel, any damage to the braided sheath is obvious upon examination. Thus, in the unlikely event that the elongated core breaks, the relatively larger amount of braid will result in minimal loss in the tensile strength of the device. This degree of robustness to damage mechanisms cannot be attained for braided sutures having smaller sheath to core ratios.

Fourth, the physical interaction between the barbed monofilament insert and the braided sheath material does not alter the tensile strength of the braided barbed suture. Thus, minor adjustments to barb designs are unlikely to have any significant impact on tensile strength.

Sutures come in different sizes, namely, 10-0, 9-0, 8-0, 7-0, 6-0, 5-0, 4-0, 3-0, 2-0, 0, 1, 2, 3, 4, and 5, with suture size 10-0 being the smallest and suture size 5 being the largest. Suture sizes 3-0 and 2-0 are often used for skin closure. Suture sizes 0 and 1 are larger than sizes 3-0 and 2-0 and are often used for closing fascia layers during abdominal surgery, and in knee and hip surgeries.

Figure 6B:
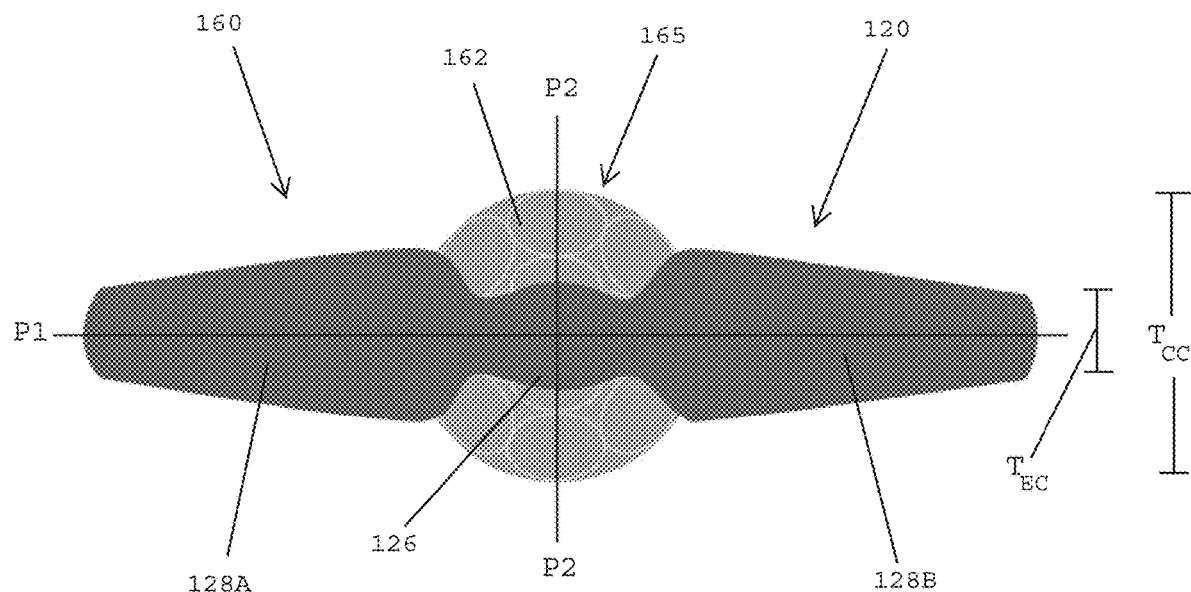
FIG. 6B is a cross-sectional view of the braided barbed suture shown in FIG. 6A.

The braided barbed sutures disclosed herein may include suture sizes 3-0, 2-0, 0, and 1. The outer diameter of the composite core 165 (FIG. 6B) may change depending upon the suture size. In general, a smaller suture size (e.g., size 3-0) will result in the formation of a composite core having a relatively smaller outer diameter and a larger suture size (e.g., size 1) will result in the formation of a composite core having a relatively larger outer diameter.

In one embodiment, it is preferred that the barbs of a braided barbed suture project outwardly beyond the outer diameter of the composite core by a sufficient distance so that the barbs are able to engage tissue for holding the braided barbed suture in place. If the tips of the barbs are embedded within the composite core (and do not extend outside of the composite core) the barbs will be rendered ineffective for holding the braided barbed suture in place.

Figure 13:
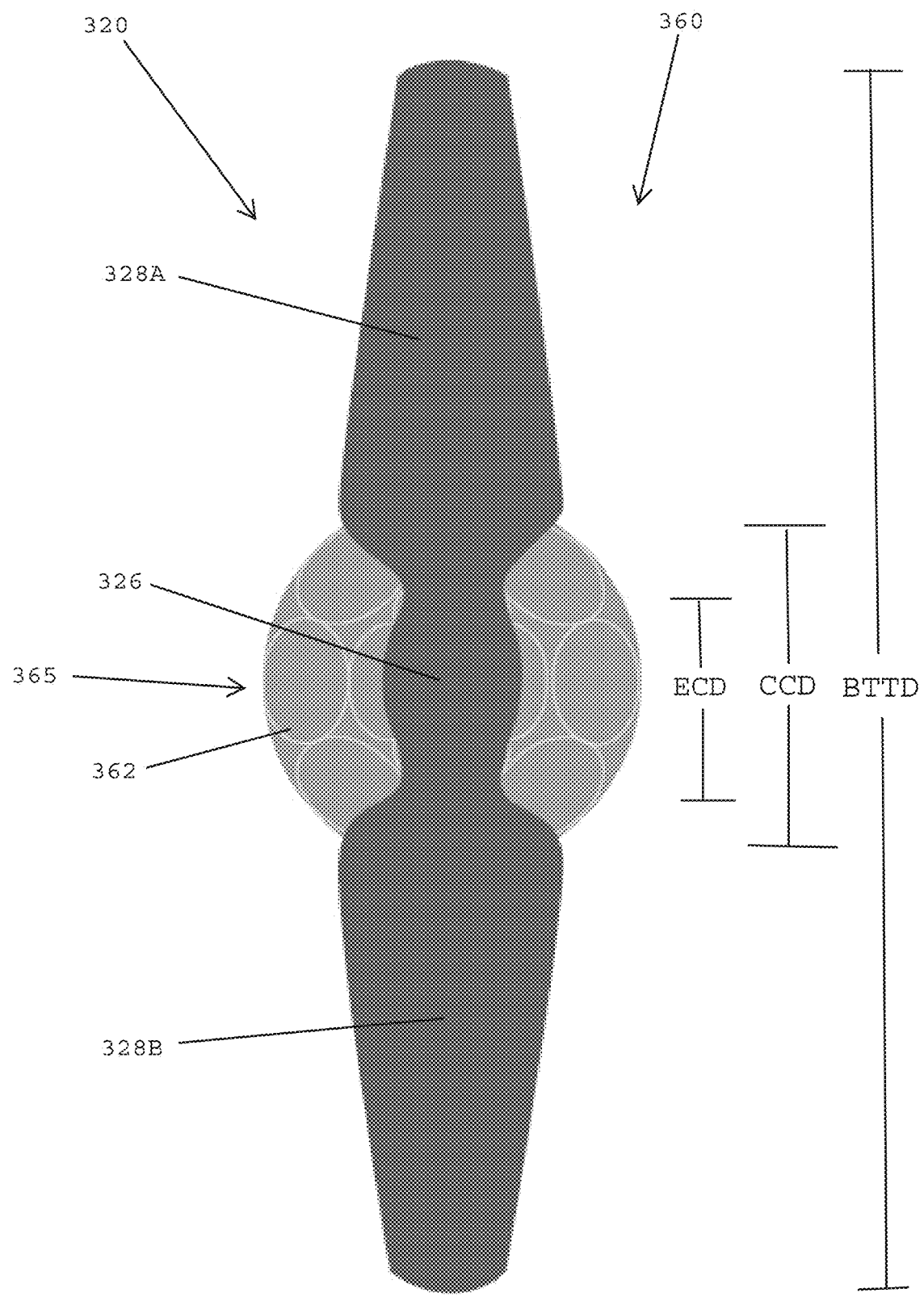
FIG. 13 is a cross-sectional view of a braided barbed suture, in accordance with one embodiment of the present patent application.

Referring to FIG. 13, in one embodiment, a braided barbed suture 360 preferably includes a barbed monofilament insert 320 (i.e., a barbed insert) including an elongated core 326 and first and second barbs 328A, 328B that project outwardly from the elongated core 326. The first and second barbs 328A, 328B define a barb tip-to-tip distance BTTD that extends from the outer surface of the tip of the first barb 328A to the outer surface of the tip of the second barb 328B. In one embodiment, a braided sheath 362 is braided over the elongated core 326 of the barbed monofilament insert 320. The elongated core 326 has a cross-sectional dimension that defines an elongated core diameter, which is designated ECD. A combination of the elongated core 326 and the braided sheath 350 form a composite core 365 having a composite core diameter, which is designated CCD. The barbed monofilament insert 320 preferably includes the first and second barbs 328A, 3285 that extend outwardly beyond the outer diameter of the composite core 365 for engaging tissue to anchor the braided barbed suture 360 in place.

In one embodiment, there are preferred ratios for the barb tip-to-tip distance (BTTD) relative to the outer diameter of the composite core (CCD) to ensure that the barbs will project a sufficient distance from the composite core for effectively engaging tissue for anchoring the braided barbed suture 360 in place. Generally, if the BTTD/CCD ratio is close to 1:1, the barbs 328A, 328B will not be able to properly anchor into the tissue. If the ratio is larger, e.g., between about 1.90:1 to 4.50:1, the barbs will project by a sufficient distance beyond the outer diameter of the composite core so that the barbs can effectively anchor into tissue.

Figure 14A:
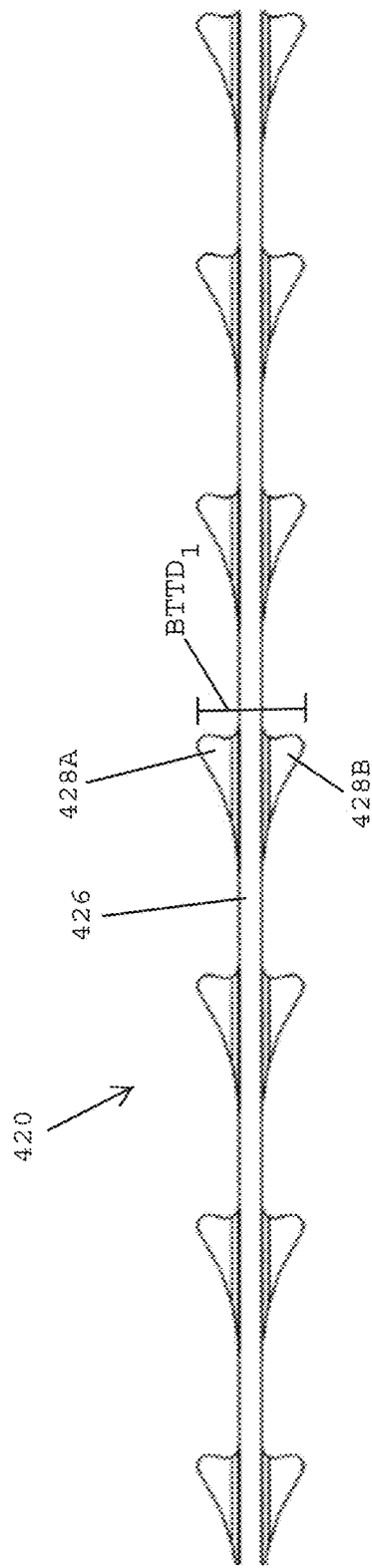
FIG. 14A is a top view of a barbed monofilament insert used for making a braided barbed suture, in accordance with one embodiment of the present patent application.

Referring to FIGS. 14A and 145, in one embodiment, a barbed monofilament insert 420 preferably includes an elongated core 426 and pairs of first and second barbs 428A, 428B that project outwardly from opposite sides of the elongated core 426. The first and second barbs 428A, 4288 define a barb tip-to-tip distance $BTTD_1$ of approximately 33 mils.

Figure 14B:
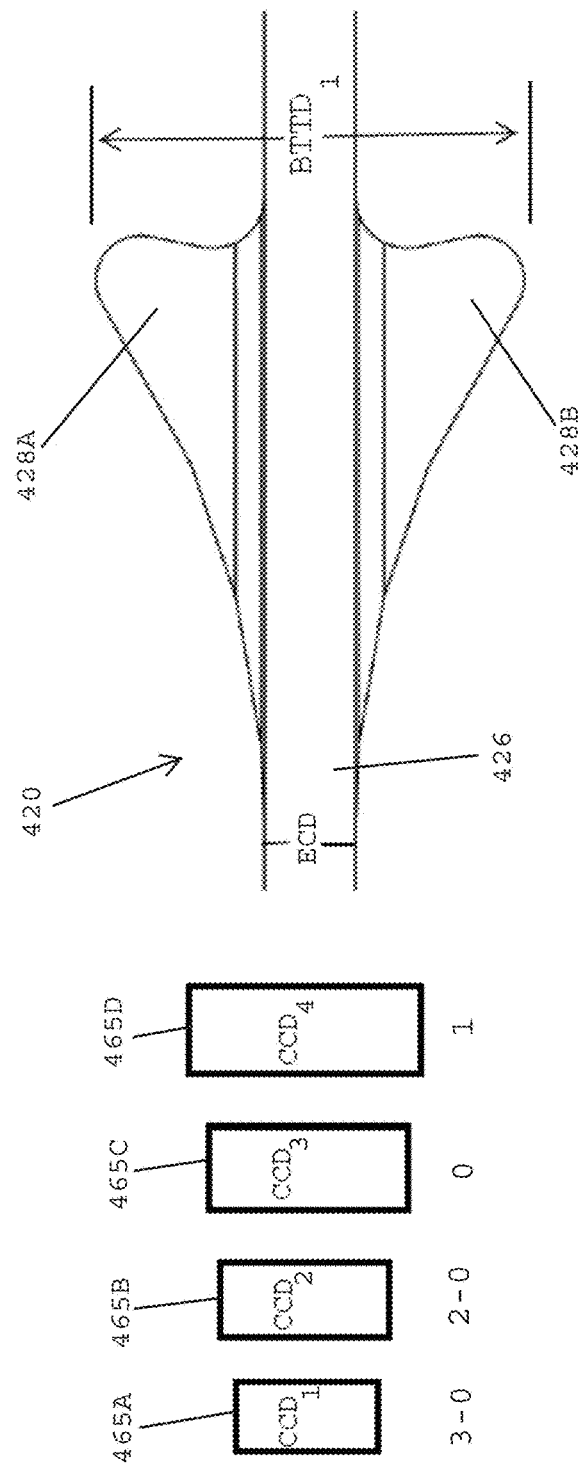
FIG. 14B is a schematic view of the composite core diameters of braided sheaths formed over barbed monofilament inserts having different suture sizes, in accordance with one embodiment of the present patent application.
Figure 17:
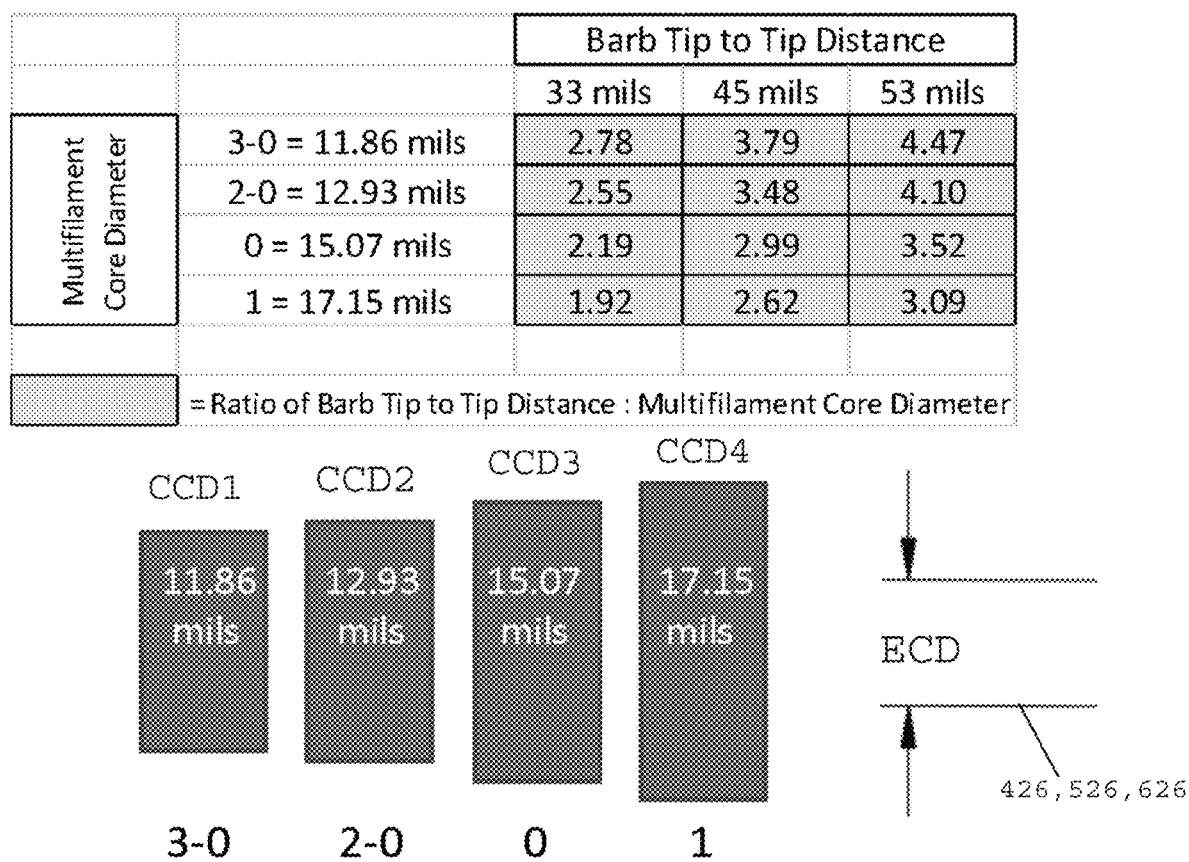
FIG. 17 is a chart showing ratios related to barb tip-to-tip distances (BTTD) and composite core diameters (CCD) for barbed monofilament inserts having different suture sizes, in accordance with one embodiment of the present patent application.

Referring to FIGS. 14B and 17, in one embodiment, the elongated core 426 is suture size 3-0. In one embodiment, a braided sheath wrapped around the elongated core defines a first composite core 465A having a composite core diameter $COD_1$ of 11.86 mils. The ratio of the barb tip-to-tip distance $BTTD_1$ (33 mils) to the composite core diameter $CCD_1$ (11.86 mils) is about 2.78:1.

In one embodiment, the elongated core 426 is suture size 2-0. In one embodiment, a braided sheath wrapped around the elongated core defines a second composite core 465B having a composite core diameter $COD_2$ of 12.93 mils. The ratio of the barb tip-to-tip distance $BTTD_1$ (33 mils) to the composite core diameter $COD_2$ (12.93 mils) is about 2.55:1.

In one embodiment, the elongated core 426 is suture size 0. In one embodiment, a braided sheath wrapped around the elongated core defines a third composite core 4650 having a composite core diameter $COD_3$ of 15.07 mils. The ratio of the barb tip-to-tip distance $BTTD_1$ (33 mils) to the composite core diameter $COD_3$ (15.07 mils) is about 2.19:1.

In one embodiment, the elongated core 426 is suture size 1. In one embodiment, a braided sheath wrapped around the elongated core defines a fourth composite core 465D having a composite core diameter $COD_4$ of 17.15 mils. The ratio of the barb tip-to-tip distance $BTTD_1$ (33 mils) to the composite core diameter $COD_4$ (17.15 mils) is about 1.92:1.

Figure 15A:
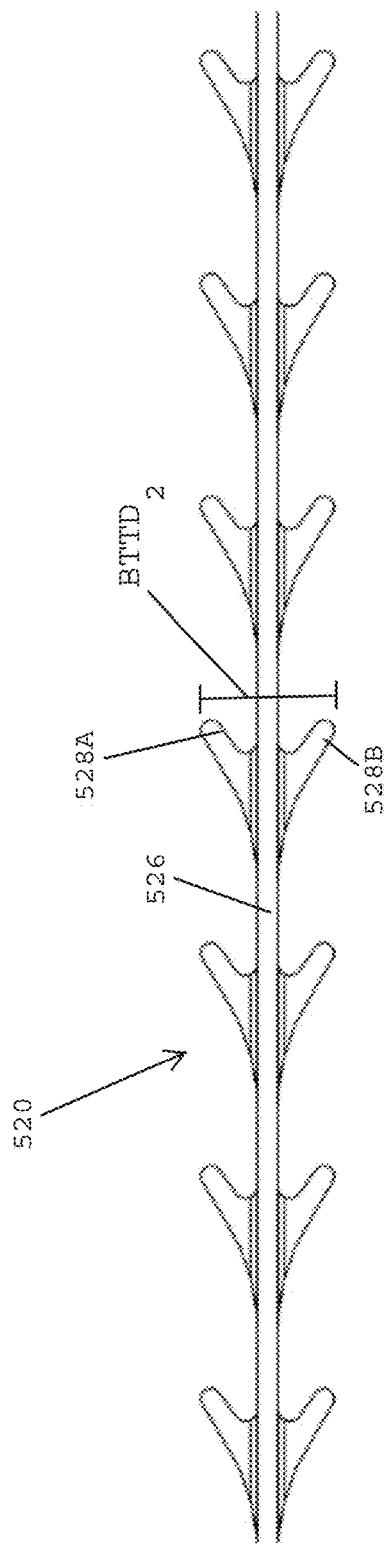
FIG. 15A is a top view of a barbed monofilament insert used for making a braided barbed suture, in accordance with one embodiment of the present patent application.
Figure 15B:
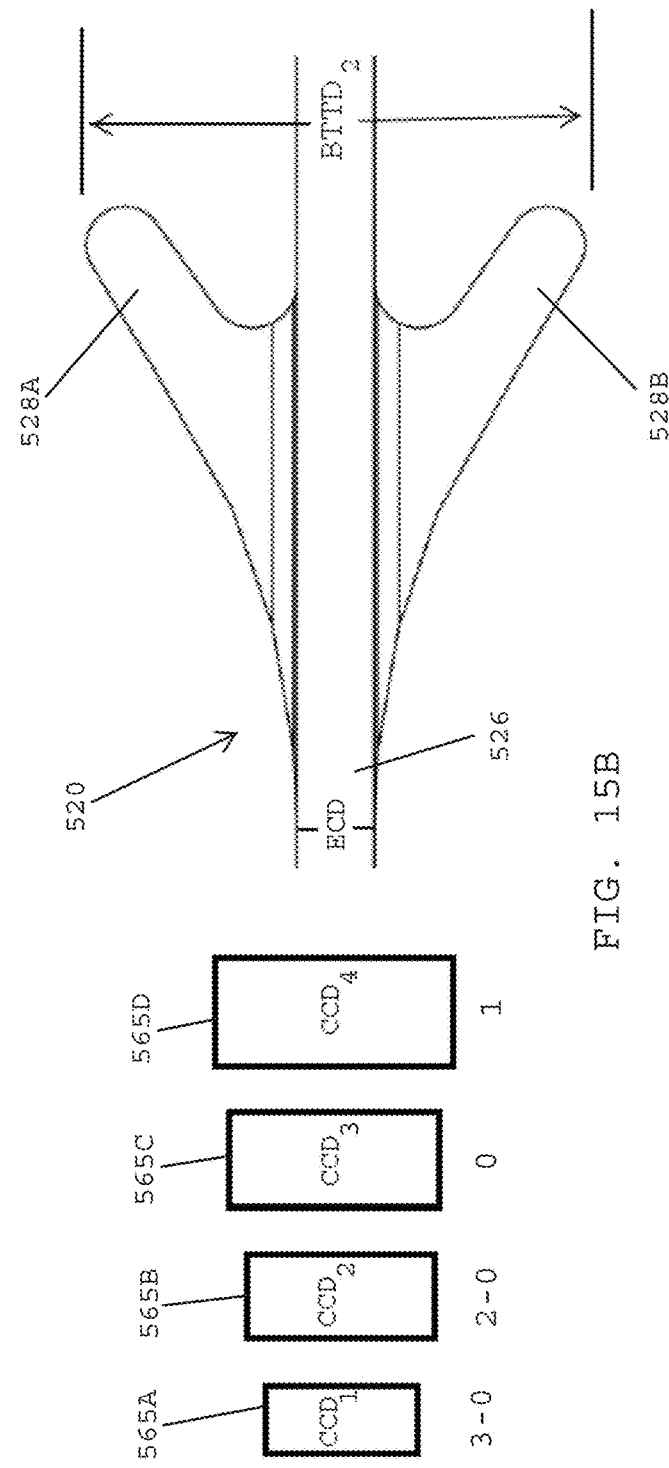
FIG. 15B is a schematic view of the composite core diameters of braided sheaths formed over barbed monofilament inserts having different suture sizes, in accordance with one embodiment of the present patent application.

Referring to FIGS. 15A and 15B, in one embodiment, a barbed monofilament insert 520 includes an elongated core 526 and pairs of first and second barbs 528A, 528B that project outwardly from opposite sides of the elongated core 526. The first and second barbs 528A, 528B define a barb tip-to-tip distance $BTTD_2$ of approximately 45 mils.

Referring to FIGS. 15B and 17, in one embodiment, the elongated core 526 is suture size 3-0. In one embodiment, a braided sheath wrapped around the elongated core defines a first composite core 565A having a composite core diameter $CCD_1$ of 11.86 mils. The ratio of the barb tip-to-tip distance $BTTD_2$ (45 mils) to the composite core diameter $CCD_1$ (11.86 mils) is about 3.79:1.

In one embodiment, the elongated core 526 is suture size 2-0. In one embodiment, a braided sheath wrapped around the elongated core defines a second composite core 565B having a composite core diameter $CCD_2$ of 12.93 mils. The ratio of the barb tip-to-tip distance $BTTD_2$ (45 mils) to the composite core diameter $CCD_2$ (12.93 mils) is about 3.48:1.

In one embodiment, the elongated core 526 is suture size 0. In one embodiment, a braided sheath wrapped around the elongated core defines a third composite core 565C having a composite core diameter $CCD_3$ of 15.07 mils. The ratio of the barb tip-to-tip distance $BTTD_2$ (45 mils) to the composite core diameter $CCD_3$ (15.07 mils) is about 2.99:1.

In one embodiment, the elongated core 526 is suture size 1. In one embodiment, a braided sheath wrapped around the elongated core defines a fourth composite core 565D having a composite core diameter $CCD_3$ of 17.15 mils. The ratio of the barb tip-to-tip distance $BTTD_2$ (45 mils) to the composite core diameter $CCD_4$ (17.15 mils) is about 2.62:1.

Figure 16A:
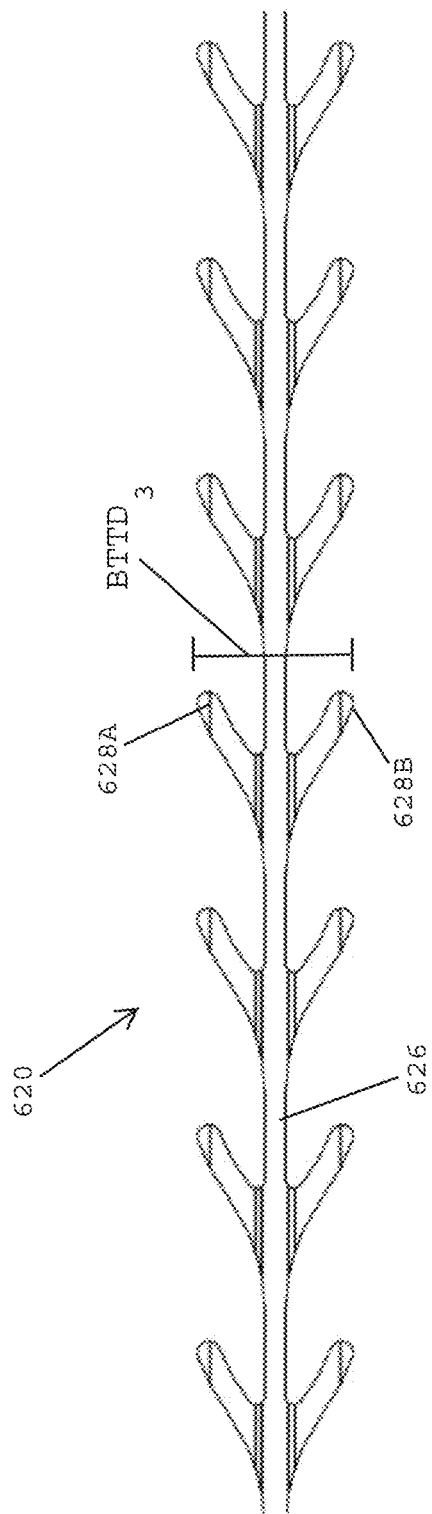
FIG. 16A is a top view of a barbed monofilament insert used for making a braided barbed suture, in accordance with one embodiment of the present patent application.

Referring to FIGS. 16A and 168B, in one embodiment, a barbed monofilament insert 620 includes an elongated core 626 and first and second barbs 628A, 628B that project outwardly from opposite sides of the elongated core 626. The first and second barbs 628A, 6288 define a barb tip-to-tip distance $BTTD_3$ of approximately 53 mils.

Figure 16B:
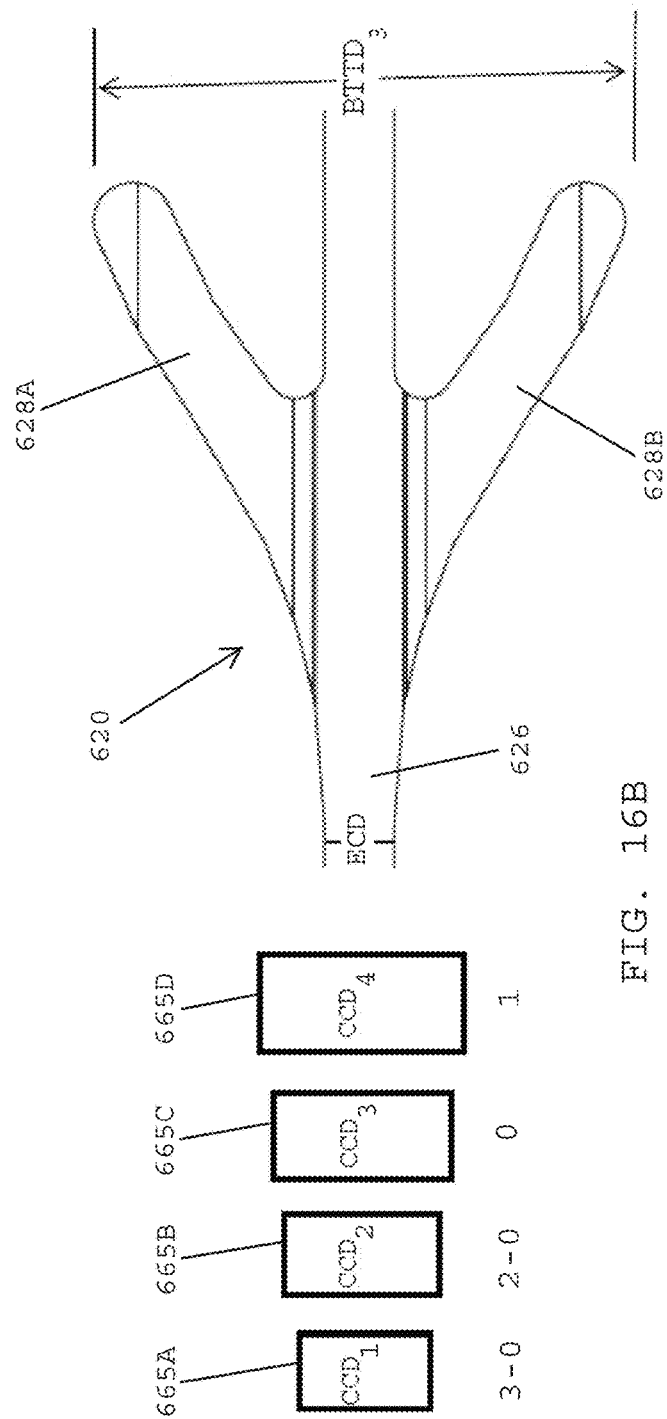
FIG. 16B is a schematic view of the composite core diameters of braided sheaths formed over barbed monofilament inserts having different suture sizes, in accordance with one embodiment of the present patent application.

Referring to FIGS. 16B and 17, in one embodiment, the elongated core 626 is suture size 3-0. In one embodiment, a braided sheath wrapped around the elongated core defines a first composite core 665A having a composite core diameter $CCD_1$ of 11.86 mils. The ratio of the barb tip-to-tip distance $BTTD_3$ (53 mils) to the composite core diameter $CCD_1$ (11.86 mils) is about 4.47:1.

In one embodiment, the elongated core 626 is suture size 2-0. In one embodiment, a braided sheath wrapped around the elongated core defines a second composite core 6658B having a composite core diameter $CCD_2$ of 12.93 mils. The ratio of the barb tip-to-tip distance $BTTD_3$ (53 mils) to the composite core diameter $CCD_2$ (1293 mils) is about 4.10:1.

In one embodiment, the elongated core 626 is suture size 0. In one embodiment, a braided sheath wrapped around the elongated core defines a third composite core 6650 having a composite core diameter $CCD_3$ of 15.07 mils. The ratio of the barb tip-to-tip distance $BTTD_3$ (53 mils) to the composite core diameter $CCD_3$ (15.07 mils) is about 3.52:1.

In one embodiment, the elongated core 626 is suture size 1. In one embodiment, a braided sheath wrapped around the elongated core defines a fourth composite core 665D having a composite core diameter $CCD_3$ of 17.15 mils. The ratio of the barb tip-to-tip distance $BTTD_3$ (53 mils) to the composite core diameter $CCD_4$ (17.15 mils) is about 3.09:1.

Figure 18:
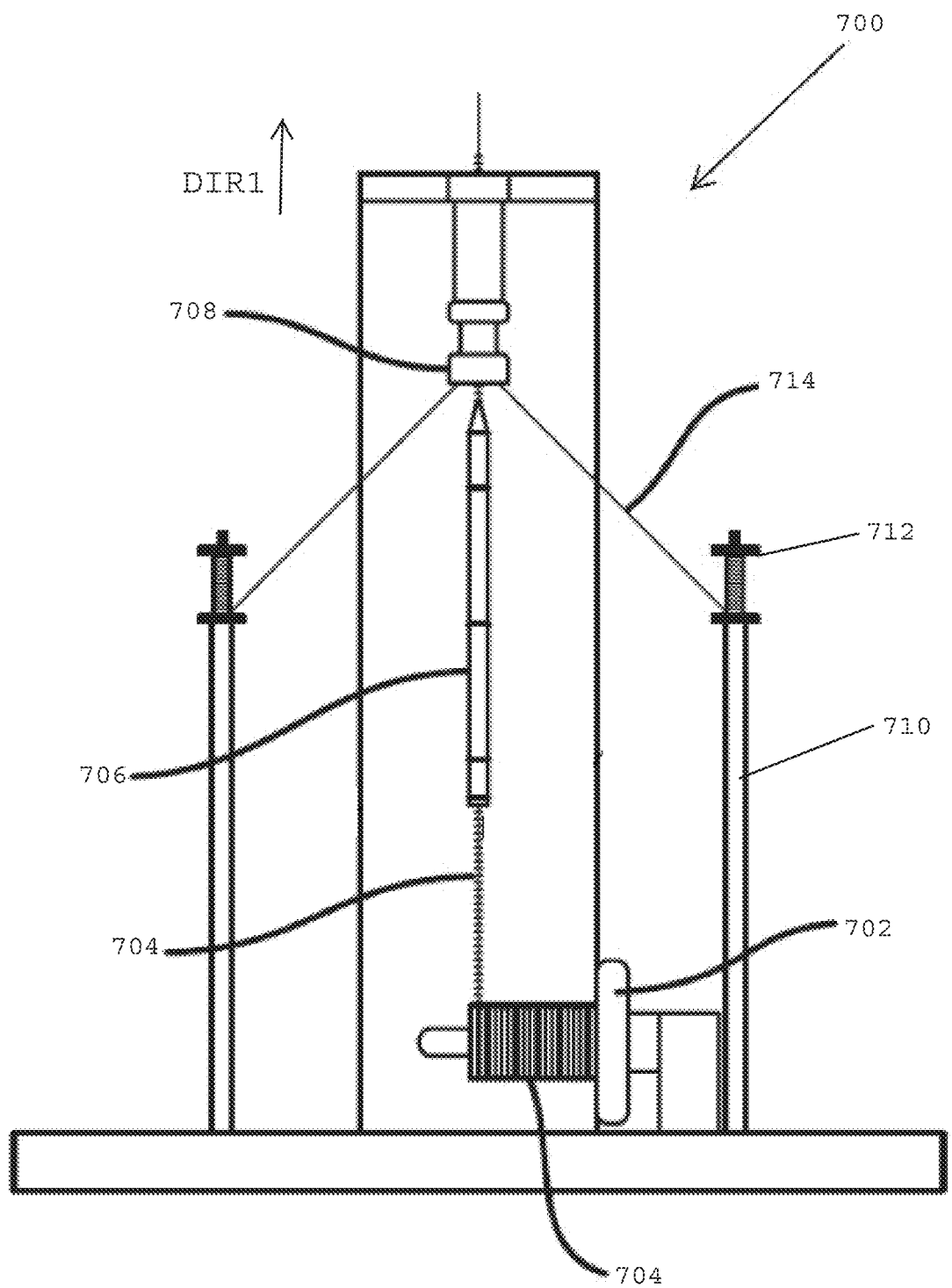
FIG. 18 is a schematic view of an automated braiding system use for making braided barbed sutures, in accordance with one embodiment of the present patent application.

Referring to FIG. 18, in one embodiment, an automated braiding system 700 for making braided barbed sutures preferably includes a spool 702 that holds a continuous roll of barbed monofilament inserts 704. In one embodiment, the barbed monofilament inserts 704 are directed through an elongated body 706 (in the direction DIRT), as disclosed in commonly assigned, U.S. patent application Ser. No. 17/336,680, filed on even date herewith, which claims benefit of U.S. Provisional Application Ser. No. 63/039,649, filed on Jun. 16, 2020, the disclosure of which is hereby incorporated by reference herein. In one embodiment, the elongated body 706 feeds the barbed monofilament inserts 704 into a braider eyelet 708 for over-braiding yarn around the elongated cores of the respective barbed monofilament inserts. The automated braiding system 700 preferably includes a plurality of shuttle carriers 710 that surround the elongated body 706 and the braider eyelet 708. Each shuttle carrier 710 preferably has a bobbin 712 mounted thereon, which holds yarn 714 that is desirably fed into the braider eyelet 708 for being wound around the barbed filament inserts 704 to form braided sheaths that extend along the length of the barbed filament inserts.

In one embodiment, the over-braiding parameters that are used by the automated braiding system 700 may be predetermined and/or modified to control the quality and specification of the braided sheaths that are formed over the barbed monofilament inserts 704. The over-braiding parameters may include the number of bobbins 712 that are used and the Denier of the yarn 714 that is provided on the bobbins.

As used herein, Denier (D) is a unit of measure for the linear mass density of fibers. It is the mass in grams per 9,000 meters of the fiber. The Denier unit of measure is based on a natural reference, namely, a single, 9,000 meter long strand of silk weighs about one gram, or approximately one Denier. The Denier unit is calculated as follows, 1 Denier=1 g/9,000 m=0.11 mg/m.

In one embodiment, the number of bobbins 712 that are used in the automated braiding system 700 may be predetermined and/or modified for controlling the density of the braided sheath that is formed over a barbed suture insert. For example, using more bobbins will result in more yarn being directed into the braider eyelet 708, which will result in a braided sheath having a higher filament density, and using fewer bobbins will result in less yarn being directed into the braider eyelet 708, which will result in a braided sheath having a lower filament density.

In one embodiment, each bobbin 712 contains yarn 714 that is fed into the braider eyelet 708. The Denier of the yarn may be predetermined to control the number of filaments that are directed into the braider eyelet 708. In one embodiment, each filament in the yarn 714 is approximately 2 Denier. Thus, 28 Denier yarn comprises 14 filaments, 56 Denier yarn comprises 28 filaments, and 80 Denier yarn comprises 40 filaments. The Denier of the yarn 714 may be selected to control the density of the braided sheath that is formed over a barbed monofilament insert.

In one embodiment, the braided sheath that is formed over a barbed monofilament insert has distinct picks that may be counted along the length of a braided barbed suture. As used herein, the term "pick" is defined to mean one repeat of the braid measured along the longitudinal axis of the braided sheath. The terminology "picks per inch" (PPI) means the number of picks along the longitudinal axis of the braided barbed suture device.

Figure 19:
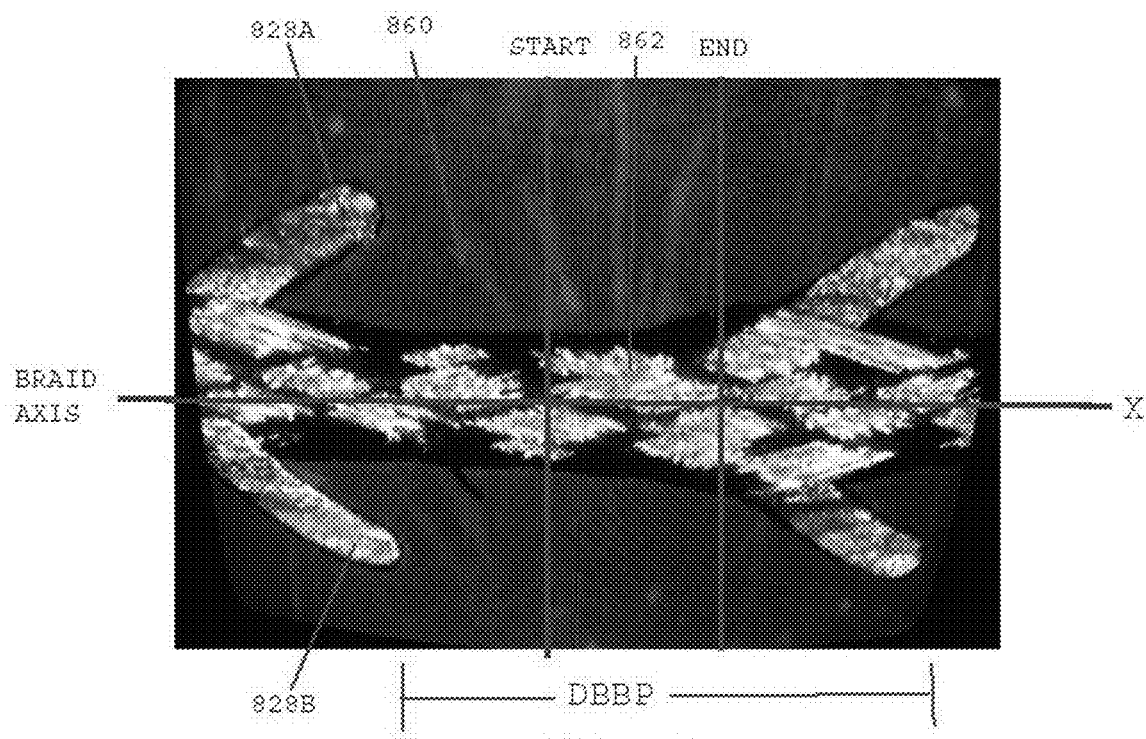
FIG. 19 is a top view of a braided barbed suture having a braided sheath with picks, in accordance with one embodiment of the present patent application.

FIG. 19 shows a braided barbed suture 860 having a braided sheath 862 that extends along a braid axis. The starting and ending points of a single pick is identified in FIG. 19. The distance between barb pairs (DBBP) may be about 0.075 inches.

Figure 20:
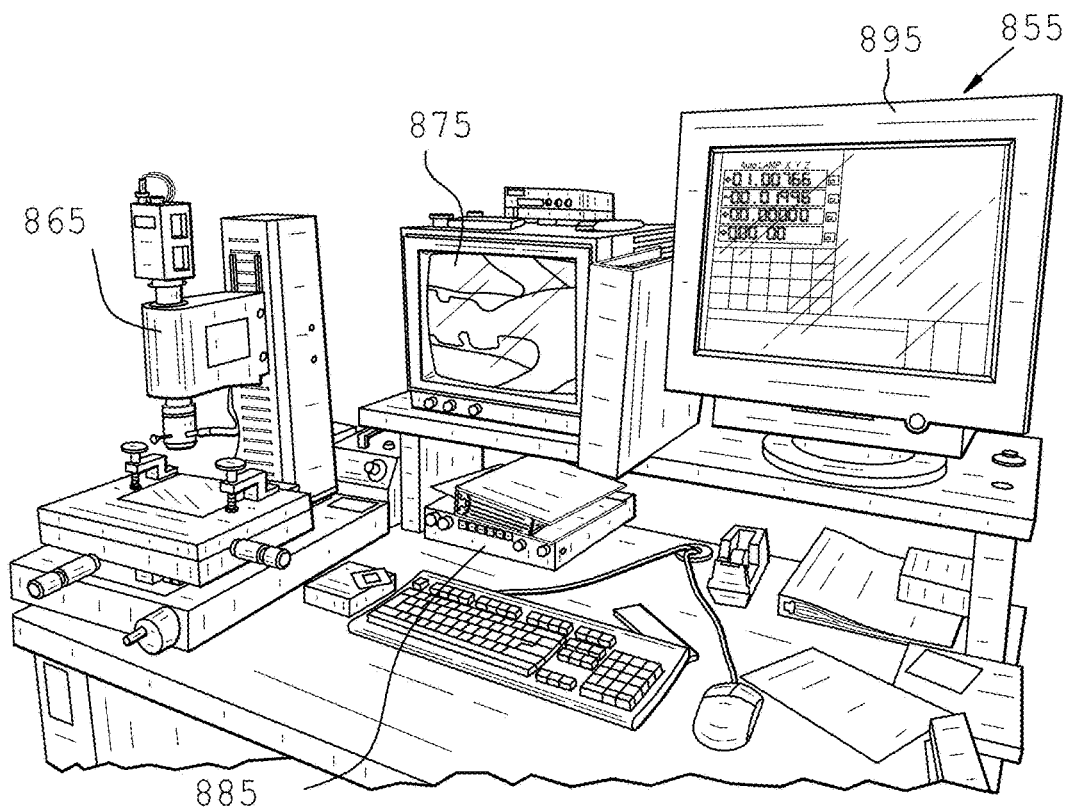
FIG. 20 is a perspective view of a system for counting picks on braided sheaths of braided barbed sutures, in accordance with one embodiment of the present patent application.

Referring to FIG. 20, in one embodiment, a pick counting system 855 may be used for inspecting a braided barbed suture 860 (FIG. 19) to determine the picks per inch (PPI) of the braided sheath 862. In one embodiment, the pick counting system 855 preferably includes a microscope 865 for viewing the braided sheath, a video display screen 875 for viewing an image of the braided sheath captured by the microscope 865, a digital crosshair generator 885 that generates a visual crosshair on the braided sheath that is shown on the video display screen 875, and a computer 895 that operates one or more software programs (i.e., the PPI software) that are configured for assisting operators in counting the picks per inch (PPI) on the braided sheath 862 of the braided barbed suture 860 (FIG. 19).

Figure 21:
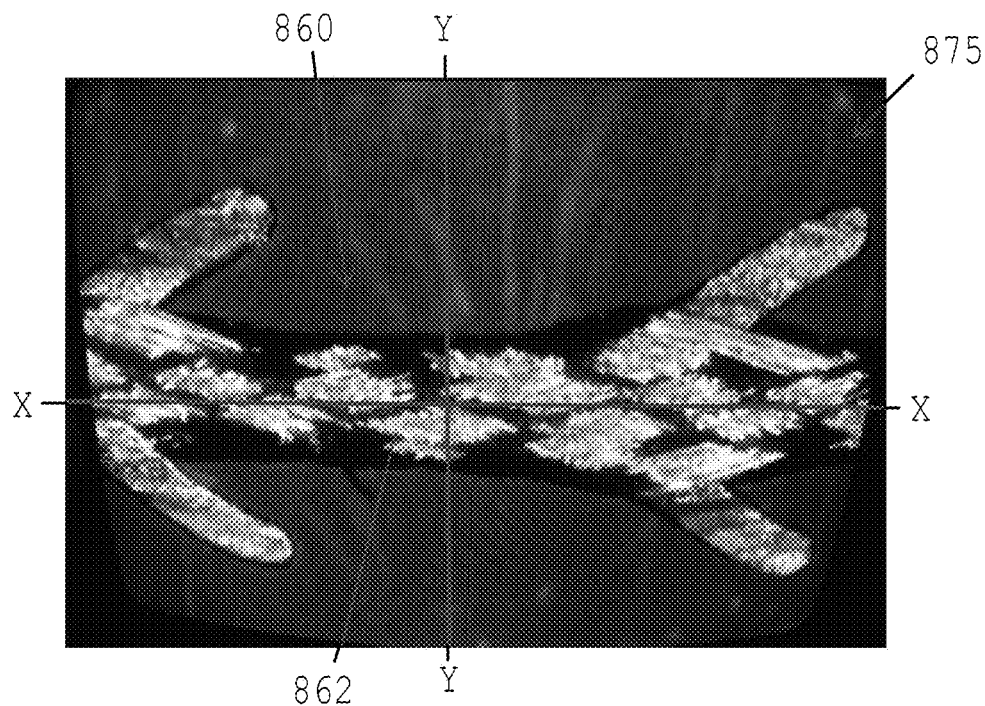
FIG. 21 illustrates a first stage of a method of counting picks on braided sheaths of braided barbed sutures, in accordance with one embodiment of the present patent application.

Referring to FIGS. 20 and 21, in one embodiment, the PPI software is opened for displaying, inter alia, distance measurements on the video display monitor 875. The braided barbed suture 860 may be placed on a microscope plate that is within the field of view of the microscope 895. In one embodiment, the braided barbed suture 860 may be held stationary by a securing component (e.g., adhesive tape, a clamp). In one embodiment, with the braided barbed suture 860 under the microscope 865 and the braided sheath 862 being visible within the video display monitor 875, the digital crosshair generator preferably aligns crosshairs with the start of a first pick of the braided sheath. In FIG. 21, the crosshairs include a Y axis and an X axis that intersect at a location that indicates the start of the first pick of the braided sheath 862. The crosshairs are displayed on the video display monitor 875.

Figure 22:
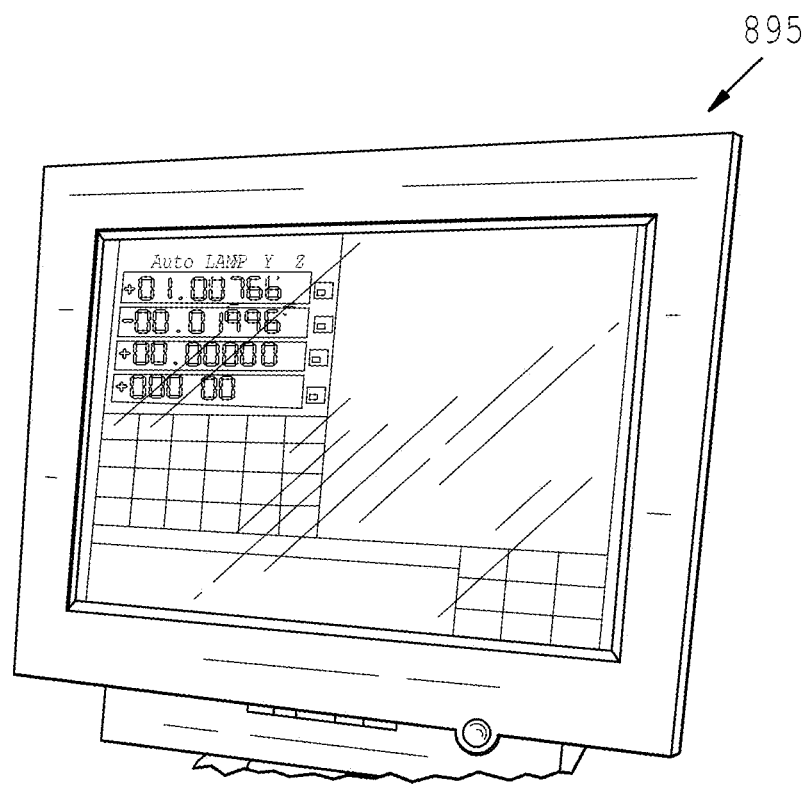
FIG. 22 illustrates a second stage of a method of counting picks on braided sheaths of braided barbed sutures, in accordance with one embodiment of the present patent application.
Figure 23:
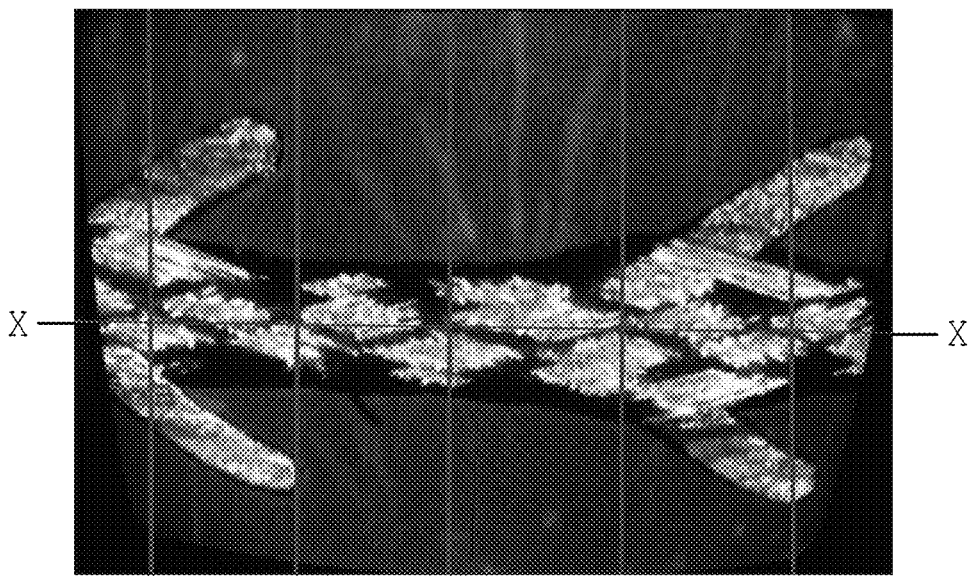
FIG. 23 illustrates a third stage of a method of counting picks on braided sheaths of braided barbed sutures, in accordance with one embodiment of the present patent application.

Referring to FIGS. 22 and 23, in one embodiment, the computer 895 of the pick counting system counts the number of picks that are located along the X axis (FIG. 21) until 1.00 inch is measured along the X axis of the braided sheath 862. In FIG. 23, starting and ending locations of four picks are highlighted. In the embodiment shown in FIG. 23, the four picks have an aggregate length that is greater than 1.00 inches.

Figure 24:
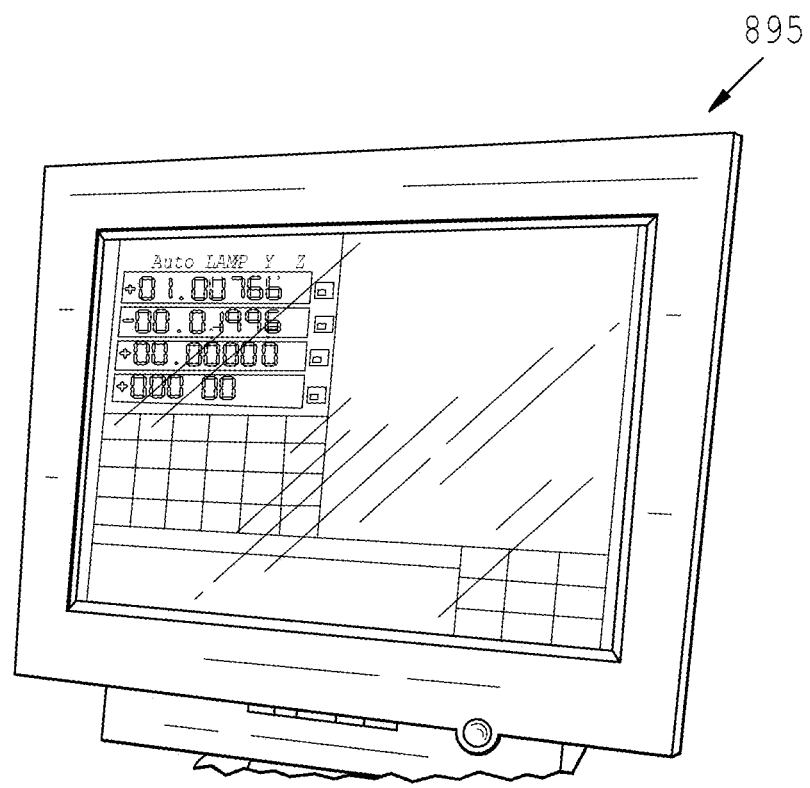
FIG. 24 illustrates a fourth stage of a method of counting picks on braided sheaths of braided barbed sutures, in accordance with one embodiment of the present patent application.

Referring to FIG. 24, in one embodiment, the total number of picks that are counted over the distance of one inch is calculated and the picks per inch (PPI) value is displayed on the display screen of the computer 895.

Referring to FIG. 19, in one embodiment, the braided barbed suture 860 has pairs of barbs 828A, 828B that are spaced from one another along the length of the braided barbed suture. The braided sheath 862 extends along the length of the braided barbed suture 860. The distance between the barb pairs, also referred to herein as the DBBP, in approximately 0.075 inches.

Figure 26:
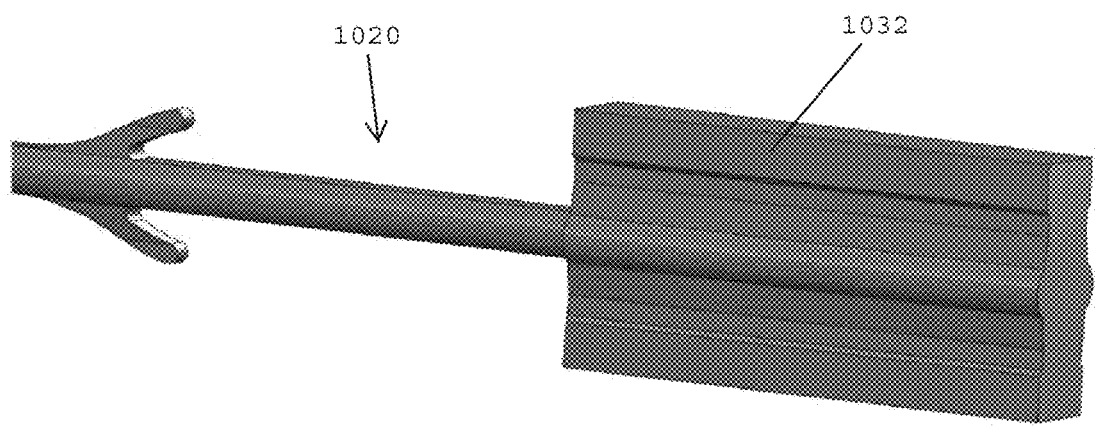
FIG. 26 is a perspective view of a barbed monofilament insert having an end effector, in accordance with one embodiment of the present patent application.

Referring to FIGS. 18, 25, and 26, in one embodiment, the over-braiding parameters used by the automated braiding system 700 may be controlled for optimizing the performance of the braided barbed suture 860.

In one embodiment, if the barbed monofilament insert is size 3-0 and the DBBP is 0.075 inches, a braiding configuration that uses 16 shuttle carriers 710, each securing one bobbin 712 that holds 28 Dernier yarn (i.e., 14 filaments), will generate a braided sheath having 55 picks per inch (PPI). The PPI number may be used to calculate as inch per pick (IPP) value of 0.0182, which is the inverse of PPI. The DBBP/IPP ratio will be 0.075/0.0182=4.13.

In one embodiment, if the barbed monofilament insert is size 2-0 and the DBBP is 0.075 inches, a braiding configuration that uses 12 shuttle carriers 710, each securing one bobbin 712 that holds 56 Denier yarn (i.e., 28 filaments), will generate a braided sheath having 50 picks per inch (PPI). The PPI number may be used to calculate as inch per pick (IPP) value of 0.0200, which is the inverse of PPI. The DBBP/IPP ratio will be 0.075/0.0200=3.75.

In one embodiment, if the barbed monofilament insert is size 0 and the DBBP is 0.075 inches, a braiding configuration that uses 16 shuttle carriers 710, each securing one bobbin 712 that holds 56 Denier yarn (i.e., 28 filaments), will generate a braided sheath having 48 picks per inch (PPI). The PPI number may be used to calculate as inch per pick (IPP) value of 0.0208, which is the inverse of PPI. The DBBP/IPP ratio will be 0.075/0.0208=3.60.

In one embodiment, if the barbed monofilament insert is size 1 and the DBBP is 0.075 inches, a braiding configuration that uses 16 shuttle carriers 710, each securing one bobbin 712 that holds 80 Denier yarn (i.e., 40 filaments), will generate a braided sheath having 41 picks per inch (PPI). The PPI number may be used to calculate as inch per pick (IPP) value of 0.0244, which is the inverse of PPI. The DBBP/IPP ratio will be 0.075/0.0244=3.08.

In one embodiment, the DBBP/IPP ratio is an over-braiding parameter that may be optimized to prevent burying barbs underneath the yarn of the braided sheath of the braided barbed suture. If the DBBP/IPP ratio is too low, the yarn will be braided too tightly and is more likely to bury the barbs. In contrast, if the DBBP/IPP ratio is too high, the yarn will be too sparsely over-braided, and the braided barbed suture will not benefit from the improved mechanical properties afforded by its presence.

In one embodiment, a preferred DBBP/IPP ratio is between about 2.75-4.50. Depending upon the suture size of the barbed suture insert, the Denier of the yarn and the number of bobbins that are used may be modified to ensure that the DBBP/IPP ratio is between 2.75-4.50 Denier.

Figure 27:
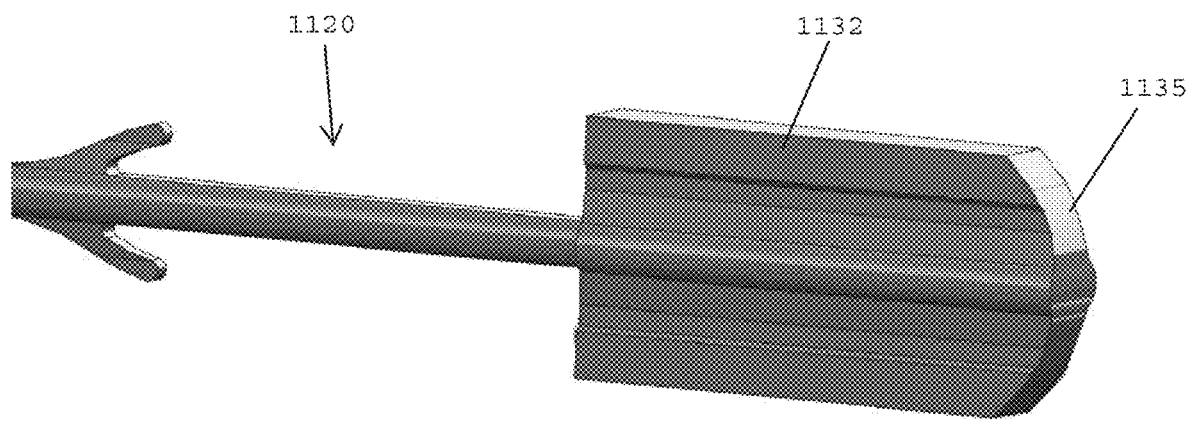
FIG. 27 is a perspective view of a barbed monofilament insert having an end effector, in accordance with one embodiment of the present patent application.
Figure 28:
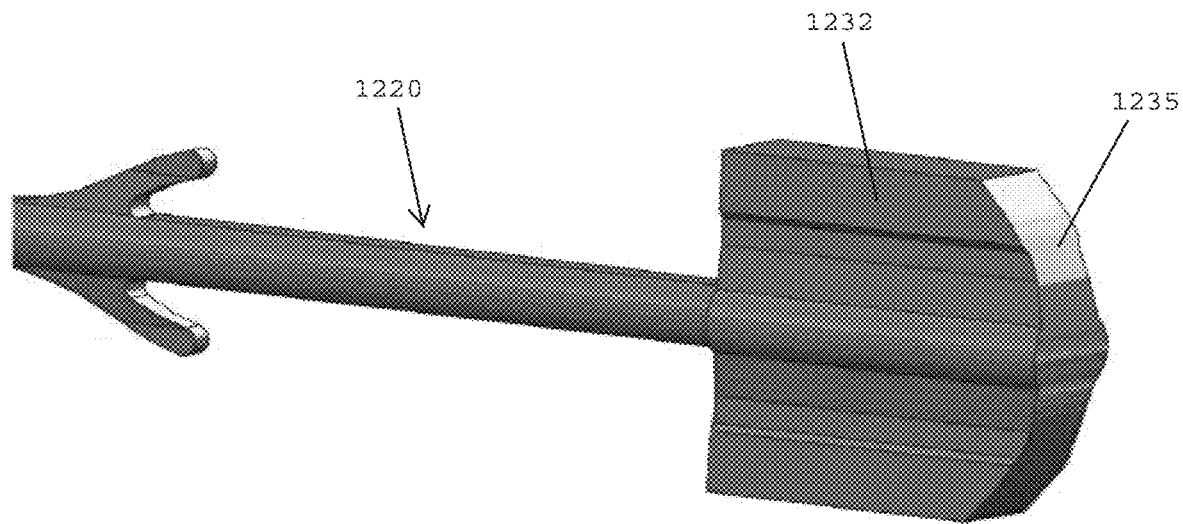
FIG. 28 is a perspective view of a barbed monofilament insert having an end effector, in accordance with one embodiment of the present patent application.

The end effectors of a barbed suture insert may have different geometric shapes (e.g., square, rectangle, circle, ellipse, diamond, half-circle, etc.). The end effectors may also have sloping surfaces for modifying the lateral width of the end effector along the length of the end effector. Referring to FIG. 27, in one embodiment, a barbed suture insert 1020 has an end effector 1032 having a rectangular shape. Referring to FIG. 28, in one embodiment, a barbed suture insert 1120 has an end effector 1132 having a rectangular shape with a proximal end 1135 that defines a curved surface. Referring to FIG. 29, in one embodiment, a barbed suture insert 1220 has an end effector 1232 having a square shape with a proximal end 1235 that defines a curved surface.

The braided end effector of a braided barbed suture may be laminated with or sandwiched by two end attachment pieces that are bonded or welded to the braided end effector. The end attachment pieces are preferably of the same general shape as the end effector (e.g., square, rectangle, circle, ellipse, diamond, half-circle, etc.) and are made of the same material as the barbed suture blank 100/barbed monofilament insert. The end attachment pieces may be secured to the braided end effector in a manner similar to what is disclosed in U.S. Pat. Nos. 10,336,001 and D780,918, the disclosures of which are hereby incorporated by reference herein.

While the foregoing is directed to embodiments of the present invention, other and further embodiments of the invention may be devised without departing from the basic scope thereof, which is only limited by the scope of the claims that follow. For example, the present invention contemplates that any of the features shown in any of the embodiments described herein, or incorporated by reference herein, may be incorporated with any of the features shown in any of the other embodiments described herein, or incorporated by reference herein, and still fall within the scope of the present invention.

What is claimed is:

1. A braided barbed suture comprising:
a barbed monofilament insert including an elongated core having an elongated core thickness and a plurality of barbs projecting outwardly from opposite sides of said elongated core; and
a braided sheath surrounding said elongated core to form a composite core of said braided barbed suture having a composite core thickness, wherein a ratio of the elongated core thickness to the composite core thickness is between about 0.16 to 0.91,
wherein the plurality of barbs project outwardly from the elongated core within a first plane,
wherein the thicknesses of the elongated core and the composite core are measured along an axis that lies within a second plane that is perpendicular to the first plane, and
wherein the barbed monofilament insert comprises:
a first barb projecting outwardly from the elongated core, the first barb including an inner end having a first thickness that is greater than the thickness of the elongated core and an outer end having a second thickness that is less than the first thickness at the inner end of the first barb; and
a transition zone that extends between the elongated core and the inner end of the first barb for connecting the inner end of the first barb with the elongated core.

2. The braided barbed suture as claimed in claim 1, wherein the ratio of the elongated core thickness to the composite core thickness is between about 0.24 to 0.73.

3. The braided barbed suture as claimed in claim 1, wherein said braided sheath envelopes at least a portion of said elongated core, and wherein said elongated core is located in a center of said composite core.

4. The braided barbed suture as claimed in claim 1, wherein said transition zone is thinner adjacent said elongated core and is thicker adjacent the inner end of said first barb, and wherein said transition zone widens from said elongated core to the inner end of said first barb.

5. The braided barbed suture as claimed in claim 4, wherein said braided sheath comprises fibers that are wound around said elongated core and said transition zone of said barbed monofilament insert.

6. The braided barbed suture as claimed in claim 5, wherein said barbs project outwardly beyond an outer perimeter of said braided sheath.

7. The braided barbed suture as claimed in claim 1, wherein the barbed monofilament insert comprises a PDS monofilament core.

8. The braided barbed suture as claimed in claim 1, wherein said elongated core has a convexly curved top surface and a convexly curved bottom surface, and wherein the thickness of said elongated core extends from said convexly curved top surface to said convexly curved bottom surface of said elongated core.

9. The braided barbed suture as claimed in claim 1, wherein said elongated core has a substantially flat top surface and a substantially flat bottom surface, and wherein a diameter of said elongated core extends from said substantially flat top surface to said substantially flat bottom surface of said elongated core.

10. The braided barbed suture as claimed in claim 1, wherein said plurality of barbs define pairs of barbs that define a barb tip-to-tip distance (BTTD), wherein said composite core has a composite core diameter (CCD), and wherein a ratio of said barb tip-to-tip distance (BTTD) to said composite core diameter (CCD) is between about 1.92-4.5.

11. The braided barbed suture as claimed in claim 10, wherein the ratio of said barb tip-to-tip distance (BTTD) to said composite core diameter (CCD) is between about 2.5-3.8.

12. A braided barbed suture comprising:
a barbed monofilament insert including an elongated core having an elongated core thickness and a plurality of barbs projecting outwardly from opposite lateral sides of said elongated core, wherein said plurality of barbs lie within a first plane, and wherein the elongated core thickness of said elongated core is measured along an axis that lies within a second plane that is perpendicular to the first plane; and
a braided sheath surrounding said elongated core to form a composite core of said braided barbed suture in which said elongated core is located in a center of said composite core and said braided sheath envelopes said elongated core, wherein said composite core has a composite core thickness that is measured along the axis that lies within the second plane that is perpendicular to the first plane, and wherein a ratio of the elongated core thickness to the composite core thickness is between about 0.16 to 0.91,
wherein said barbs have inner ends having respective thicknesses that are greater than the elongated core thickness, and
wherein the barbs have inner ends having respective thicknesses that are greater than the elongated core thickness.

13. The braided barbed suture as claimed in claim 12, wherein the elongated core thickness is about 6-8 mil and the composite core thickness is about 13-18 mil.

14. The braided barbed suture as claimed in claim 12, wherein the ratio of the elongated core thickness relative to the composite core thickness is between about 0.24 to 0.73.

15. The braided barbed suture as claimed in claim 12, further comprising:
a first transition zone located between a first lateral side of said elongated core and an inner end of a first barb, wherein said first transition zone widens from the first lateral side of said elongated core to the inner end of said first barb; and
a second transition zone located between a second lateral side of said elongated core and an inner end of a second barb, wherein said second transition zone widens from the second lateral side of said elongated core to the inner end of said second barb.

16. The braided barbed suture as claimed in claim 15, wherein said elongated core and said first and second transition zones defines a first concave profile on a top side of said braided barbed suture and a second concave profile on a bottom side of said braided barbed suture.

17. The braided barbed suture as claimed in claim 12, wherein said braided barbed suture has a single breaking point for both said braided sheath and said barbed monofilament insert.

18. The braided barbed suture as claimed in claim 12, wherein said barbed monofilament insert comprises a PDS monofilament core, and wherein said braided sheath comprises a VICRYL multifilament yarn braided sheath.

19. The braided barbed suture as claimed in claim 12, further comprising:
an end effector coupled with elongated core, wherein said elongated core extends through said end effector, the end effector being a knot-replacement feature where the braided barbed suture is configured to hold tissue in a desired position without the introduction of knots into the suture;
said end effector including a first wing that extends laterally from a first lateral side of said elongated core and a second wind that extends laterally from a second lateral side of said elongated core, wherein said first and second wings are thicker than said elongated core.

20. A braided barbed suture comprising:
a barbed monofilament insert including an elongated core having an elongated core thickness and a plurality of barbs projecting outwardly from opposite sides of said elongated core, wherein said barbs have inner ends that are thicker than the elongated core thickness of said elongated core;
said barbed monofilament insert including at least one transition zone located between said elongated core and the inner ends of said barbs to form a concave profile; and
a braided sheath surrounding said elongated core to form a composite core of said braided barbed suture in which said elongated core is located in a center of said composite core and said braided sheath surrounds said elongated core, wherein said composite core has a thickness that is greater than the elongated core thickness, and wherein a ratio of the elongated core thickness relative to the composite core thickness is between about 0.16 to 0.91.

21. The braided barbed suture as claimed in claim 20, wherein said plurality of barbs lie within a first plane, and wherein the elongated core thickness and the composite core thickness are measured along an axis that lies within a second plane that is perpendicular to the first plane of said plurality of barbs.

22. The braided barbed suture as claimed in claim 20, wherein the ratio of the elongated core thickness relative to the composite core thickness is between about 0.24 to 0.73.

23. The braided barbed suture as claimed in claim 20, wherein said braided barbed suture has a single breaking point for both said braided sheath and said barbed monofilament insert.

24. The braided barbed suture as claimed in claim 20, wherein the transition zone is thinner adjacent to the elongated core and is thicker adjacent to the inner ends of the barbs, and wherein the transition zone widens from the elongated core to the inner ends of the barbs.

25. The braided barbed suture as claimed in claim 24, wherein the braided sheath comprises fibers that are wound around the elongated core and the transition zone of the barbed monofilament insert.

26. The braided barbed suture as claimed in claim 20, wherein the elongated core has a convexly curved top surface and a convexly curved bottom surface, and wherein the thickness of the elongated core extends from the convexly curved top surface to the convexly curved bottom surface of the elongated core.

27. The braided barbed suture as claimed in claim 20, wherein said elongated core has a substantially flat top surface and a substantially flat bottom surface, and wherein a diameter of the elongated core extends from the substantially flat top surface to the substantially flat bottom surface of the elongated core.

28. The braided barbed suture as claimed in claim 20, wherein the plurality of barbs define pairs of barbs that define a barb tip-to-tip distance (BTTD), wherein the composite core has a composite core diameter (CCD), and wherein a ratio of the barb tip-to-tip distance (BTTD) to the composite core diameter (CCD) is between about 1.92-4.5.

29. The braided barbed suture as claimed in claim 20, wherein the barbed monofilament insert comprises a PDS monofilament core, and wherein the braided sheath comprises a VICRYL multifilament yarn braided sheath.

\* \* \* \* \*